US011324774B2

(12) United States Patent
O'Connor et al.

(10) Patent No.: US 11,324,774 B2
(45) Date of Patent: May 10, 2022

(54) COMPOSITIONS OF ORAL ALKALINE SALTS AND METABOLIC ACID INDUCERS AND USES THEREOF

(71) Applicant: Augusta University Research Institute, Inc., Augusta, GA (US)

(72) Inventors: Paul O'Connor, Martinez, GA (US); Ryan Harris, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 16/237,885

(22) Filed: Jan. 2, 2019

(65) Prior Publication Data

US 2019/0231813 A1 Aug. 1, 2019

Related U.S. Application Data

(60) Provisional application No. 62/613,949, filed on Jan. 5, 2018.

(51) Int. Cl.
| | | |
|---|---|---|
| *A61K 33/00* | (2006.01) | |
| *A61K 31/198* | (2006.01) | |
| *A61K 9/08* | (2006.01) | |
| *A61K 9/00* | (2006.01) | |
| *A61P 3/10* | (2006.01) | |
| *A61P 9/12* | (2006.01) | |
| *A61P 9/10* | (2006.01) | |
| *A61P 3/04* | (2006.01) | |
| *A61P 29/00* | (2006.01) | |

(52) U.S. Cl.
CPC ............ *A61K 33/00* (2013.01); *A61K 9/0056* (2013.01); *A61K 9/08* (2013.01); *A61K 31/198* (2013.01); *A61P 3/04* (2018.01); *A61P 3/10* (2018.01); *A61P 9/10* (2018.01); *A61P 9/12* (2018.01); *A61P 29/00* (2018.01); *A61K 9/0095* (2013.01)

(58) Field of Classification Search
CPC ........ A61K 33/00; A61K 9/0056; A61K 9/08; A61K 31/198; A61K 9/0095; A61P 9/10; A61P 3/04; A61P 3/10; A61P 9/12; A61P 29/00

See application file for complete search history.

(56) References Cited

U.S. PATENT DOCUMENTS

| | | | |
|---|---|---|---|
| 6,649,168 B2 * | 11/2003 | Arvinte | A61K 9/0019 424/198.1 |
| 6,930,125 B2 * | 8/2005 | Hunt | A61K 9/0078 514/172 |
| 7,052,694 B2 | 5/2006 | Pease | |
| 7,332,582 B2 | 2/2008 | Hardy | |
| 7,390,888 B2 | 6/2008 | Pease | |
| 7,411,051 B2 | 8/2008 | Rosen | |
| 7,488,802 B2 | 2/2009 | Collins | |
| 7,521,051 B2 | 4/2009 | Collins | |
| 7,524,498 B2 | 4/2009 | Hardy | |
| 7,563,869 B2 | 7/2009 | Honjo | |
| 7,888,385 B2 * | 2/2011 | Hunt | A61K 9/0078 514/172 |
| 7,981,416 B2 | 7/2011 | Hardy | |
| 8,088,905 B2 | 1/2012 | Collins | |
| 8,114,845 B2 | 2/2012 | Langermann | |
| 8,188,238 B2 | 5/2012 | Pease | |
| 8,287,856 B2 | 10/2012 | Li | |
| 8,383,796 B2 | 2/2013 | Korman | |
| 8,580,247 B2 | 11/2013 | Li | |
| 8,609,089 B2 | 12/2013 | Langermann | |
| 8,709,416 B2 | 4/2014 | Langermann | |
| 8,728,474 B2 | 5/2014 | Honjo | |
| 8,779,105 B2 | 7/2014 | Korman | |
| 9,067,999 B1 | 6/2015 | Honjo | |
| 9,073,994 B2 | 7/2015 | Honjo | |
| 9,084,776 B2 | 7/2015 | Korman | |
| 9,102,725 B2 | 8/2015 | Korman | |
| 9,205,148 B2 | 12/2015 | Langermann | |
| 9,238,075 B2 * | 1/2016 | Gorelick | A61K 33/14 |
| 9,255,147 B2 | 2/2016 | Pease | |
| 9,273,135 B2 | 3/2016 | Korman | |
| 9,352,044 B2 * | 5/2016 | Gorelick | A61K 47/10 |
| 9,358,289 B2 | 6/2016 | Korman | |
| 9,387,247 B2 | 7/2016 | Korman | |
| 9,393,301 B2 | 7/2016 | Honjo | |
| 9,487,581 B2 | 11/2016 | Abate | |

(Continued)

OTHER PUBLICATIONS

Li et al., High-Methionine Diet Attenuates Severity of Arthritis and Modulates IGF-I Related Gene Expressions in an Adjuvant Arthritis Rats Model. Mediators of Inflammation (2016), ID 9280529, 6 pages (Year: 2016).*
Young, The Cause and Cure for Rheumatoid Arthritis. Int J Complement Alt Med 2016, 4(3):00116 (Year: 2016).*
Loniewski et al., Bicarbonate therapy for prevention of chronic kidney disease progression. Kidney International (2014) 85:529-535. (Year: 2014).*
Bass, K.K. et al., "Immunopotentiation with Low-Dose Cyclophosphamide in the Active Specific Immunotherapy of Cancer", Cancer Immunol. Immunother., 47:1-12 (1998). (Abstract Only).
Berger, Raanan et al., "Phase I Safety and Pharmacokinetic Study of CT-011, a Humanized Antibody Interacting with PD-1, in Patients with Advanced Hematologic Malignancies", Clin. Cancer Res., 14(10): 3044-3051 (2008).

(Continued)

*Primary Examiner* — Robert A Wax
*Assistant Examiner* — Olga V. Tcherkasskaya
(74) *Attorney, Agent, or Firm* — Smith, Gambrell & Russell; Judy Jarecki-Black

(57) ABSTRACT

Compositions of alkaline salts and metabolic acid inducers and methods of use thereof are provided. The disclosed compositions may be used for stimulating vagal nerve efferent pathways, treating or preventing an inflammatory response or an autoimmune disorder, inhibiting or reducing one or more inflammatory M1 macrophages and/or one or more inflammatory neutrophils in the blood, promoting polarization of macrophages from a pro-inflammatory M1 state to an anti-inflammatory M2 state, and treating or preventing cardiovascular disease or metabolic disorders.

12 Claims, 28 Drawing Sheets

(56) References Cited

U.S. PATENT DOCUMENTS

| | | | |
|---|---|---|---|
| 9,492,539 B2 | 11/2016 | Korman | |
| 9,492,540 B2 | 11/2016 | Korman | |
| 9,534,010 B2* | 1/2017 | Hebert | C07H 19/167 |
| 9,580,507 B2 | 2/2017 | Korman | |
| 2002/0064516 A1* | 5/2002 | Arvinte | A61K 9/0019 |
| | | | 424/85.1 |
| 2002/0119192 A1* | 8/2002 | Vishwanathan | A61K 9/2009 |
| | | | 424/461 |
| 2003/0144244 A1* | 7/2003 | Hebert | A61K 9/0014 |
| | | | 514/45 |
| 2007/0134166 A1* | 6/2007 | Hunt | A61K 9/0078 |
| | | | 424/45 |
| 2008/0317729 A1* | 12/2008 | Kasch | C07C 211/63 |
| | | | 424/94.4 |
| 2009/0054384 A1* | 2/2009 | Hunt | A61K 31/19 |
| | | | 514/174 |
| 2012/0329846 A1* | 12/2012 | Matsumoto | A61K 31/198 |
| | | | 514/400 |

OTHER PUBLICATIONS

Borovikova, Lyudmila V. et al., "Vagus Nerve Stimulation Attenuates the Systemic Inflammatory Response to Endotoxin", Nature, 405: 458-462 (2000).

Brode, S. et al., "Immune-Ootentiating Effects of the Chemotherapeutic Drug Cyclophosphamide", Crit Rev. Immunol., 28:109-126 (2008). (Abstract Only).

Butte, Manish J. et al., "PD-L1 Interacts Specifically with B7-1 to Inhibit T Cell Proliferation", Immunity, 27:111-122 (2007).

Chapleau, Mark W. et al., "Chronic Vagal Nerve Stimulation Prevents High-Salt Diet-Induced Endothelial Dysfunction and Aortic Stiffening in Stroke-Prone Spontaneously Hypertensive Rats", Am. J. Physiol. Heart Circ. Physiol., 311: H276-285 (2016).

Cubillos-Ruiz, Juan R. et al., "Polyethylenimine-Based siRNA Nanocomplexes Reprogram Tumor-Associated Dendritic Cells via TLR5 to Elicit Therapeutic Antitumor Immunity", J. Clin. Invest. 119(8): 2231-2244 (2009).

De Miguel, Carmen et al., "Inflammation and Hypertension: New Understandings and Potential Therapeutic Targets", Curr. Hypertens. Rep., 17:507 (2015).

Erbe, David V. et al., "Small Molecule Ligands Define a Binding Site on the Immune Regulatory Protein B7.1", J. Biol. Chem., 277: 7363-7368 (2002).

Freeman, Gordon J. "Structures of PD-1 with its Ligands: Sideways and Dancing Cheek to Cheek", Proc. Natl. Acad. Sci. U. S. A, 105: 10275-10276 (2008).

Gigliotti, Joseph C. et al., "Ultrasound Prevents Renal Ischemia-Reperfusion Injury by Stimulating the Splenic Cholinergic Anti-Inflammatory Pathway", J. Am. Soc. Nephrol., 24: 1451-1460 (2013).

Hengst, James C.D., et al., "Importance of Timing of Cyclophosphamide Therapy of MOPC-315 Tumor-Bearing Mice", Cancer Res. 40: 2135-2141 (1980).

Hengst, James C.D. et al., "Cooperation Between Cyclophosphamide Tumoricidal Activity and Host Antitumor Immunity in the Cure of Mice Bearing Large MOPC-315 Tumors", Cancer Res. 41: 2163-2167 (1981).

Jin, Chunhua et al., "HV1 Acts as a Sodium Sensor and Promotes Superoxide Production in Medullary Thick Ascending Limb of Dahl Salt-Sensitive Rats", Hypertension 64: 541-550 (2014).

Koopman, Frieda A. et al. "Vagus Nerve Stimulation Inhibits Cytokine Production and Attenuates Disease Severity in Rheumatoid Arthritis", Proc Natl Acad. Sci USA, 113: 8284-8289 (2016).

Kosel, Markus et al., "Chronic Vagus Nerve Stimulation for Treatment-Resistant Depression Increases Regional Cerebral Blood Flow in the Dorsolateral Prefrontal Cortex", Psychiatry Res., 191:153-159 (2011).

Lázár-Molnár, Eszter et al., "Crystal Structure of the Complex Between Programmed Death-1 (PD-1) and its Ligand PD-L2", Pnas, 105: 10483-10488 (2008).

Liang, Jun et al., "Design of New Oxazaphosphorine Anticancer Drugs", Curr. Pharm. Des., 13(9): 963-978. (Review) (2007).

Machiels, Jean-Pascal H. et al., "Cyclophosphamide, Doxorubicin, and Paclitaxel Enhance the Antitumor Immune Response of Granulocyte/Macrophase-Colony Stimuylating Factor-Secreting Whole-Cell Vaccines in HER-2/neu Tolerized Mice", Cancer Res., 61: 3689-3697 (2001).

Malbert Charles-Henri et al., "Obesity-Associated Alterations in Glucose Metabolism are Reversed by Chronic Bilateral Stimulation of the Abdominal Vagus Nerve", Diabetes, 66: 848-857 (2017).

Rosas-Ballina, M. et al. "Cholinergic Control of Inflammation", J. Intern. Med. 265: 663-679 (2009).

Sammartino, Christine et al., "Anti-GBM Disease Following CTLA4 Blockage in a Patient with Metastatic Melanoma", Clinical Kidney Journal, 3(2):135-137 (2010), Published online Dec. 2009.

Serdaroglu, Ayse et al., "Long Term Effect of Vagus Nerve Stimulation in Pediatric Intractable Epilepsy: An Extended Follow-Up", Childs Nerv. Syst., 32: 641-646 (2016).

Taieb, Julien et al., "Chemoimmunotherapy of Tumors: Cyclophosphamide Synergizes with Exosome Based Vaccines", J. J. Immunol., 176: 2722-2729 (2006).

Van Der Most, Robbert G. et al., "Tumor Eradication after Cyclophosphamide Depends on concurrent Depletion of Regulatory T Cells: A Role for Cycling TNFR2-Expressing Effector-Suppressor T Cells in Limiting Effective Chemotherapy", Cancer Immunol. Immunother., 58: 1219-1228 (2009).

* cited by examiner

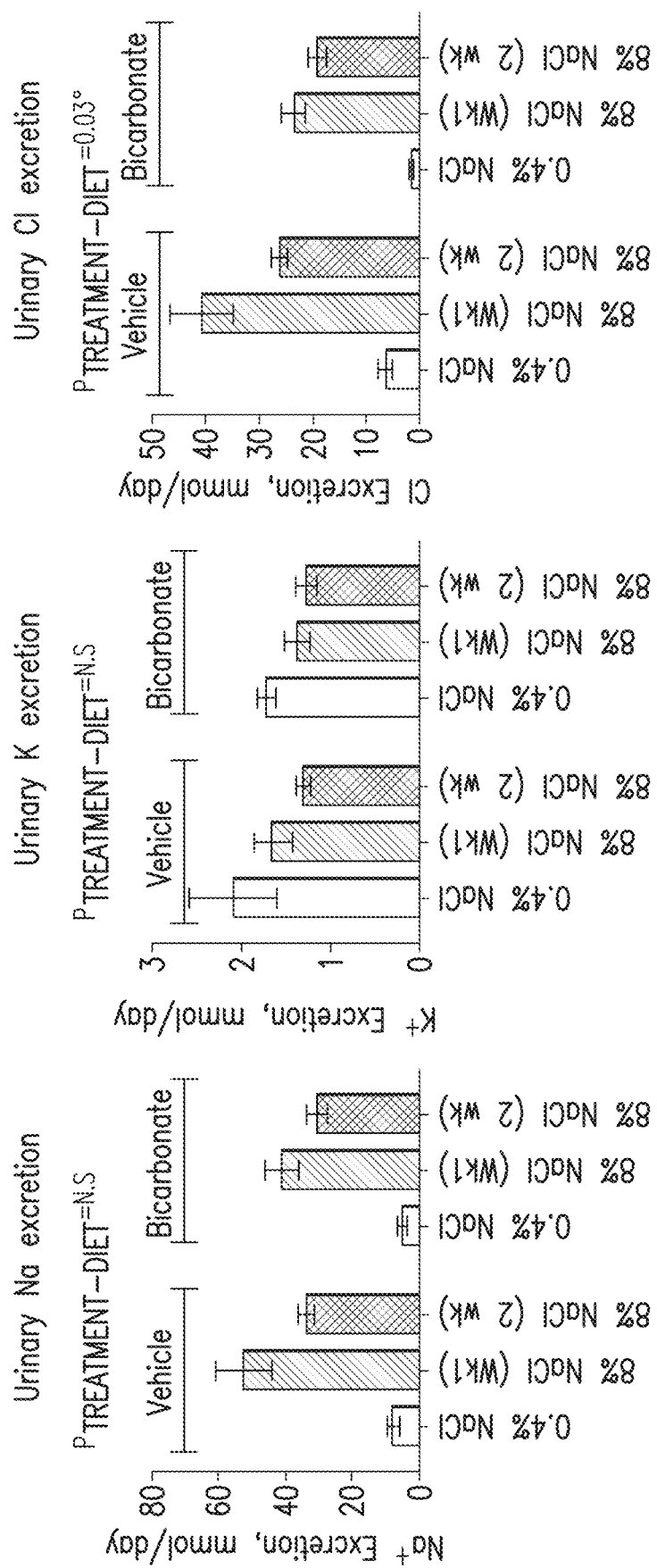

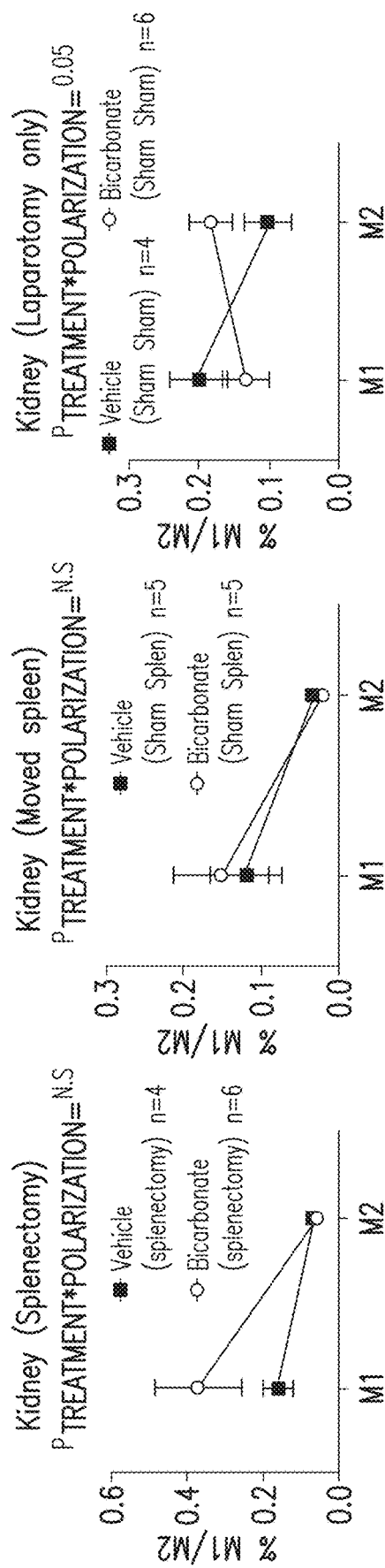

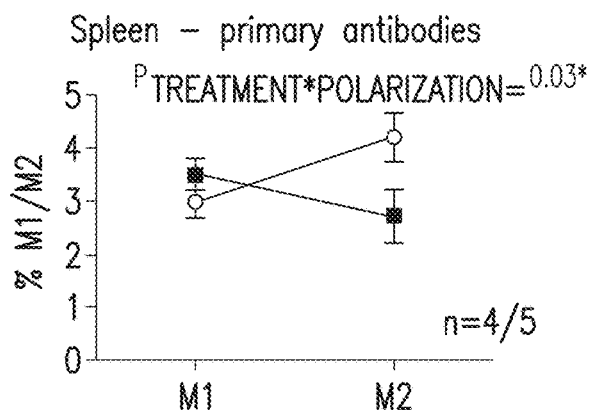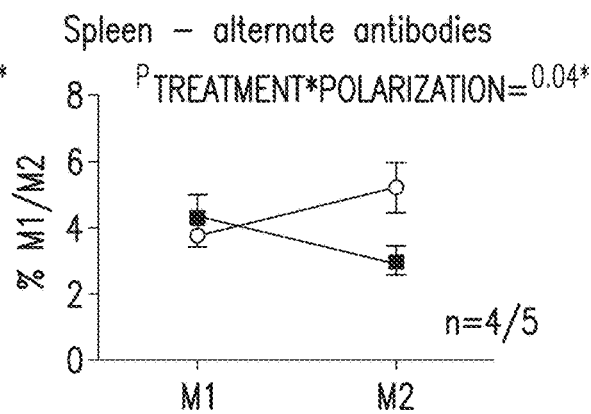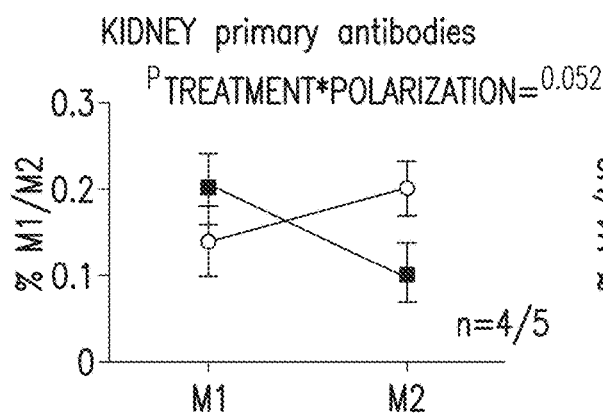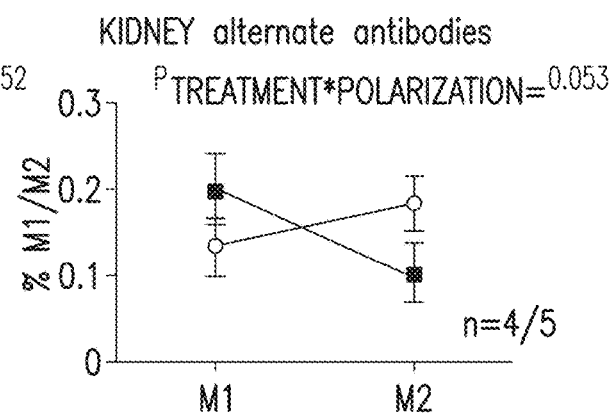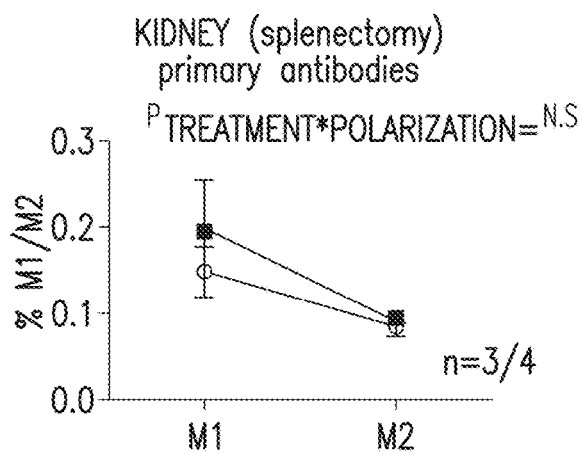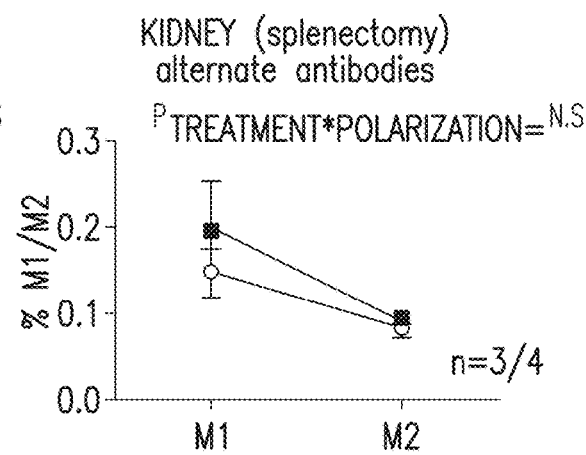

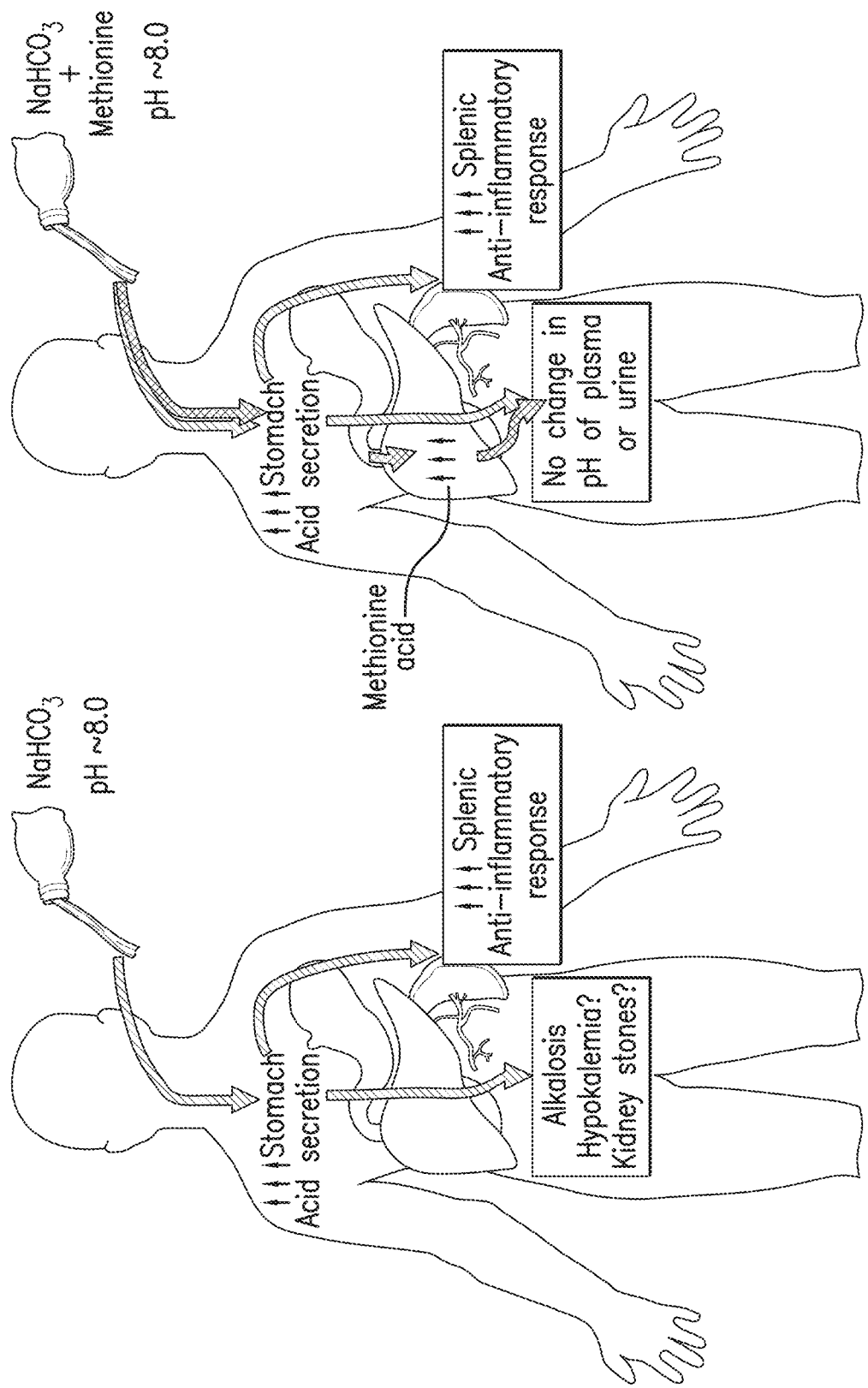

COMPOSITIONS OF ORAL ALKALINE SALTS AND METABOLIC ACID INDUCERS AND USES THEREOF

CROSS-REFERENCE TO RELATED APPLICATIONS

This application claims benefit of and priority to U.S. Provisional Application No. 62/613,949 filed on Jan. 5, 2018, which is incorporated by reference in its entirety.

STATEMENT REGARDING FEDERALLY SPONSORED RESEARCH

This invention was made with government support under DK099548 awarded by the National Institutes of Health. The government has certain rights in the invention.

FIELD OF THE INVENTION

The invention generally relates to compositions of alkaline salts and metabolic acid inducers, and their use to treat or prevent inflammation, cardiovascular disease, and metabolic disorders.

BACKGROUND OF THE INVENTION

Activation of vagal efferent nerves has been shown to demonstrate numerous physiological benefits including, for example, improved glucose control (Malbert C H et al. *Diabetes* 66:848-857 (2017)), improved vascular and endothelial function (Chapleau M W et al. *Am J Physiol Heart Circ Physiol* 311:H276-285 (2016)), treatment of depression (Kosel M et al. *Psychiatry Res* 191:153-159 (2011)), reduction of seizures in epileptic patients (Serdaroglu A et al. *Childs Nerv Syst* 32:641-646 (2016)), and stimulation of the cholinergic anti-inflammatory pathway (Borovikova L V *Nature* 405:458-462 (2000)). Given its therapeutic potential, there is currently much interest in methods to stimulate vagal nerves in vivo, especially the cholinergic anti-inflammatory pathway.

Activation of vagal efferents by non-invasive ultrasound has been demonstrated to reduce kidney injury following ischemia reperfusion (Gigliotti, J. C. et al. *J Am Soc Nephrol* 24:1451-1460). In addition, in humans, efforts to stimulate the cholinergic anti-inflammatory pathway chronically by implanting stimulating electrodes on the vagal nerves have shown promise in patients with rheumatoid arthritis (Koopman et al. *Proc Natl Acad Sci USA* 113:8284-8289 (2016)). However, ultrasound and implantable vagal nerve stimulators require surgery, are expensive, and are not readily available.

While there are a number of classes of anti-inflammatory drugs currently available on the market, each class of drug has limitations regarding their utility to treat inflammatory disease states, particularly chronic disease. For instance, chronic use of non-steroidal anti-inflammatory drugs ("NSAIDS"), which inhibit the synthesis prostaglandins and thromboxanes, results in numerous undesirable side effects including an increased risk of stomach ulcers and heart attacks. Similarly, chronic use of corticosteroids, which also inhibit inflammation and regulate a large range of physiological processes including carbohydrate metabolism, behavior, and electrolytes, lead to serious side effects. Furthermore, disease modifying anti-rheumatic drugs ("DMARDS") and biologics, which disrupt a range of immune signaling system pathways including key proinflammatory cytokines TNF-α, IL-1β, and/or enzymes involved in the production of immune cells, result in down regulation of the immune system and an increased risk of infection and malignancy and often must be administered by injection only.

Moreover, alkaline salts, for example, sodium bicarbonate, have recently been used to treat metabolic (systemic blood) acidosis in patients having chronic kidney disease. Treatment with alkaline salts helps to promote systemic alkalization and prevent the deleterious effects of acidosis (such as bone loss). However, high doses of oral alkaline salts, such as $NaHCO_3$, cause serious side effects related to systemic alkalization (i.e., alkalization of the blood after the alkaline salt has been absorbed from the gut). These side effects include hypercapnia and hypokalemia (both of which can be deadly), increased risk of kidney stones, and sodium retention and high blood pressure. Additionally, systemic alkalization and consequent development of hypokalemia prevent activation of the vagal response required to initiate the anti-inflammatory response.

Other alkaline treatments on the market include alkaline water products, antacids, and proton pump inhibitors. However, there is no evidence that alkaline water products activate the vagal nerve pathway. Alkaline water, while having negligible free $H^+$ and thus a high pH, has only a minute buffering capacity (the ability to take $H^+$ out of fluid) and therefore cannot change stomach pH significantly. Given the acid content of the stomach, such low doses of bicarbonate as those found in alkaline water are ineffective to stimulate the vagal nerve. Similarly, antacids, which act by alkalinizing the stomach pH, promote systemic alkalization and may prevent activation of the anti-inflammatory pathway itself. Due to the risk of ingesting too much $Ca^{2+}$ or $Mg^{2+}$ (which are common salts in antacids), antacids should also not be taken chronically.

Proton pump inhibitors inhibit the secretion of $H^+$ by the stomach. This promotes alkalization of the stomach fluid by preventing secretion of $H^+$. Secretion of $H^+$ into the stomach occurs in response to food in the stomach or an increase in stomach pH. It has been suggested that this secretion may be required to activate the neural pathways that stimulate the anti-inflammatory/vagal response. Thus, by inhibiting $H^+$ secretion, proton pump inhibitors may inhibit, rather than activate, the vagal response. Proton pump inhibitors are also known to increase the risk for chronic kidney disease and cause mortality.

Therefore, it is an object of the invention to provide a safe, effective, and non-invasive method to activate the cholinergic anti-inflammatory pathway while preventing systemic alkalization, which may be of benefit to patients suffering from a multitude of disease states.

SUMMARY OF THE INVENTION

Compositions of alkaline salts and metabolic acid inducers are provided that are useful for, for example, treating or preventing inflammation, an inflammatory response, or an autoimmune disorder, inhibiting or reducing one or more inflammatory M1 macrophages and/or one or more inflammatory neutrophils in the blood, promoting polarization of macrophages from a pro-inflammatory M1 state to an anti-inflammatory M2 state, treating or preventing cardiovascular disease or metabolic disorders, and stimulating vagal nerve efferent pathways.

One embodiment provides a method for treating an inflammatory condition associated with vagal nerve efferent pathways, for example, chronic kidney disease, rheumatoid arthritis, inflammatory bowel disease (IBD), or Crohn's disease, in a subject in need thereof, including administering to the subject an effective amount of at least one alkaline salt and an effective amount of at least one metabolic acid inducer to reduce or inhibit the inflammation. The at least one alkaline salt may be selected from the group consisting of sodium bicarbonate, potassium bicarbonate, and combinations thereof. For example, the at least one alkaline salt is sodium bicarbonate. The at least one metabolic acid inducer is selected from the group consisting of ammonium, methionine, and combinations thereof. In one embodiment, the at least one metabolic acid inducer is ammonium.

In certain embodiments, the at least one alkaline salt and the at least one metabolic acid inducer are administered to the subject orally, for example in pharmaceutical formulation. The pharmaceutical formulation may be a solid or a solution. In this aspect, the at least one alkaline salt is present in the solution in an amount of about 0.01M to about 0.5M. In another embodiment, the at least one alkaline salt and the at least one metabolic acid inducer are present in the solution in equimolar amounts.

In some embodiments, the effective amounts of the at least one alkaline salt and the at least one metabolic acid inducer are effective amounts to inhibit or reduce one or more inflammatory M1 macrophages and/or one or more inflammatory neutrophils in the blood of the subject as well as increasing anti-inflammatory M2 macrophages. In another embodiment, the effective amounts of the at least one alkaline salt and the at least one metabolic acid inducer are effective amounts to inhibit or reduce one or more pro-inflammatory cytokines selected from the group consisting of IL1$\alpha$, IL1$\beta$, IL6, and TNF$\alpha$.

Another embodiment provides a method of stimulating vagal nerve efferent pathways in a subject in need thereof, including administering to the subject an effective amount of at least one alkaline salt and an effective amount of at least one metabolic acid inducer. The effective amounts of the at least one alkaline salt and the at least one metabolic acid inducer are effective amounts to alkalinize the pH of the stomach of the subject. For instance, the effective amounts of the at least one alkaline salt and the at least one metabolic acid inducer are effective amounts to increase the pH of the stomach of the subject to at least a pH of 6-9. In some embodiments, the at least one alkaline salt is selected from the group consisting of sodium bicarbonate, potassium bicarbonate, and combinations thereof. In other embodiments, the at least one metabolic acid inducer is selected from the group consisting of ammonium, methionine, and combinations thereof.

Still another embodiment provides a pharmaceutical composition, including an effective amount of at least one alkaline salt, an effective amount of at least one metabolic acid inducer, and a pharmaceutically acceptable excipient. In one embodiment, the composition is formulated in solution for oral administration. In another embodiment, the composition is formulated as an extended release formulation. In some embodiments, the at least one alkaline salt is selected from the group consisting of sodium bicarbonate, potassium bicarbonate, and combinations thereof. In other embodiments, the at least one metabolic acid inducer is selected from the group consisting of ammonium, methionine, and combinations thereof. In still other embodiments, the effective amounts of the at least one alkaline salt and the at least one metabolic acid inducer are effective amounts to inhibit or reduce one or more inflammatory M1 macrophages and/or one or more inflammatory neutrophils as well as increase anti-inflammatory M2 macrophages, and thereby inhibit or reduce inflammation in a subject.

Yet another embodiment provides a method for treating or preventing a chronic cardiovascular disease or a metabolic disorder, including administering to a subject in need thereof an effective amount of the disclosed compositions. In some embodiments, the cardiovascular disease or metabolic disorder is atherosclerosis, obesity, hypertension, or type 2 diabetes.

BRIEF DESCRIPTION OF THE DRAWINGS

Further features and advantages of the invention can be ascertained from the following detailed description that is provided in connection with the drawings described below:

FIG. 1A is a bar graph showing urinary excretion of sodium in Dahl salt-sensitive rats. FIG. 1B is a bar graph showing urinary excretion of potassium in Dahl salt-sensitive rats. FIG. 1C is a bar graph showing urinary excretion of chlorine in Dahl salt-sensitive rats.

FIG. 4A is a graph showing the percentage of total kidney cells identified as M1 macrophages and M2 macrophages in vehicle and bicarbonate treated rats in which the spleen was removed. FIG. 4B is a graph showing the percentage of total kidney cells identified as M1 macrophages and M2 macrophages in vehicle and bicarbonate treated rats in which the spleen was moved to midline during surgery but not removed (sham splenectomy). FIG. 4C is a graph showing the percentage of total kidney cells identified as M1 macrophages and M2 macrophages in vehicle and bicarbonate treated rats in which the spleen was untouched during surgery (Sham Sham).

FIG. 5A is a graph showing the relative expression of M1 and M2 macrophages expressed as percentage of total spleen cells in vehicle and bicarbonate treated rats fed HS for 14 days prior to tissue harvest. FIG. 5B is a graph showing relative expression of M1 and M2 macrophages expressed as percentage of total spleen cells from vehicle and bicarbonate treated rats fed HS for 14 days prior to tissue harvest. FIG. 5C is a graph showing relative expression of M1 and M2 macrophages expressed as percentage of total kidney cells from vehicle and bicarbonate treated rats fed HS for 14 days prior to tissue harvest. FIG. 5D is a graph showing relative expression of M1 and M2 macrophages expressed as percentage of total kidney cells from vehicle and bicarbonate treated rats fed HS for 14 days prior to tissue harvest. FIG. 5E is a graph showing relative expression of M1 and M2 macrophages expressed as percentage of total kidney cells from vehicle and bicarbonate treated rats in which the spleen was removed prior to 14 days HS treatment. FIG. 5F is a graph showing relative expression of M1 and M2 macrophages expressed as percentage of total kidney cells from vehicle and bicarbonate treated rats in which the spleen was removed prior to 14 days HS treatment.

FIGS. 22A-22B are a schematic illustration of co-administration of metabolic acid inducer with NaHCO3 (FIG. 22B) vs alkali alone (FIG. 22A).

DETAILED DESCRIPTION

I. Definitions

Figure 2C:
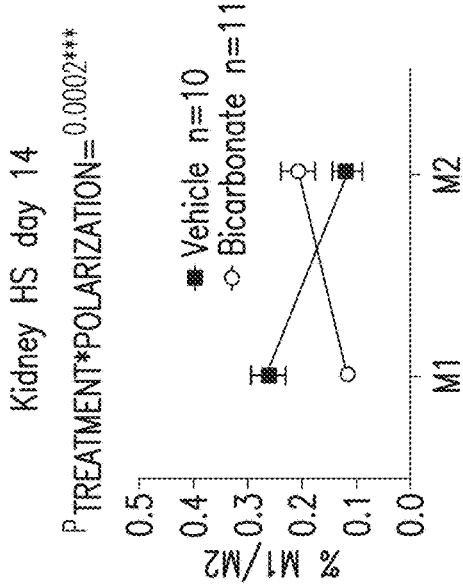
FIG. 2C is a graph showing the relative expression of M1 and M2 macrophages expressed as a percentage of total kidney cells in vehicle and bicarbonate treated rats.

As used herein, the singular forms "a," "an," and "the" include plural referents unless the context clearly dictates otherwise. For example, reference to "the method of treatment" includes reference to equivalent steps and methods known to those skilled in the art, and so forth.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments, the values may range in value either above or below the stated value in a range of approx. +/−5%; in other embodiments, the values may range in value either above or below the stated value in a range of approx. +/−2%; in other embodiments, the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "pharmaceutically-acceptable carrier" refers to one or more compatible solid or liquid fillers, diluents, or encapsulating substances that does not cause significant irritation to a human or other vertebrate animal and does not abrogate the biological activity and properties of the administered compound.

The term "carrier" or "excipient" refers to an organic or inorganic, natural or synthetic inactive ingredient in a formulation, with which one or more active ingredients are combined. In some embodiments, a carrier or an excipient is an inert substance added to a pharmaceutical composition to further facilitate administration of a compound, and/or does not cause significant irritation to an organism and does not abrogate the biological activity and properties of the administered compound.

The terms "individual," "subject," and "patient" are used interchangeably herein, and refer to a mammal, including, but not limited to, humans, rodents, such as mice and rats, and other laboratory animals.

The term "inhibit," "suppress," "decrease," "interfere," and/or "reduce" (and like terms) generally refers to the act of reducing, either directly or indirectly, a function, activity, or behavior relative to the natural, expected, or average or relative to current conditions. It is understood that this is typically in relation to some standard or expected value, in other words it is relative, but that it is not always necessary for the standard or relative value to be referred to.

The term "increase," "enhance," "stimulate," and/or "induce" (and like terms) generally refers to the act of improving or increasing, either directly or indirectly, a function or behavior relative to the natural, expected, or average or relative to current conditions. For instance, something that increases, stimulates, induces or enhances anti-inflammatory effects might induce the production and/or secretion of anti-inflammatory cytokines.

The terms "treat," "treating," or "treatment" refers to alleviating, reducing, or inhibiting one or more symptoms or physiological aspects of a disease, disorder, syndrome, or condition. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

The terms "inflammation," "inflammatory response," and "inflammatory condition" refer to acute or chronic localized or systemic responses to harmful stimuli, such as pathogens, damaged cells, physical injury or irritants, that are mediated in part by the activity of cytokines, chemokines, or inflammatory cells (e.g. macrophages) and is characterized in most instances by pain, redness, swelling, and impairment of tissue function.

II. Compositions

Compositions including an effective amount of one or more alkaline salts and one or more metabolic acid inducers for treating or preventing inflammation and cardiovascular disease are disclosed. The disclosed compositions activate vagal nerve efferent pathways and promote anti-inflammatory and cardiovascular protective effects, while preventing systemic alkalization (i.e., alkalization of the blood) from alkali loading. Without being bound by any particular theory, it has been discovered that, while selective stomach alkalization is sufficient to activate anti-inflammatory pathways, systemic alkalization prevents activation of the vagal response required to initiate the anti-inflammatory response. Through administration of an alkaline salt with a metabolic acid inducer, the disclosed compositions allow for selective alkalization of the pH of the stomach and long term activation of the vagal response in the absence of systemic internal alkalization.

In one embodiment, the disclosed compositions include one or more alkaline salts. Through selective alkalization of the stomach, the alkaline salt has been shown to promote activation of cardiovascular and anti-inflammatory pathways associated with vagal efferent pathways. Examples of alkaline salts contemplated by the present invention include, but are not limited to, sodium bicarbonate ($NaHCO_3$), sodium carbonate ($Na_2CO_3$), potassium bicarbonate ($KHCO_3$), potassium carbonate ($K_2CO_3$), calcium carbonate ($CaCO_3$), and any combination thereof. In some embodiments, the disclosed compositions may include at least one alkaline salt selected from sodium bicarbonate ($NaHCO_3$), potassium bicarbonate ($KHCO_3$), or a combination thereof. In still other embodiments, the disclosed compositions may include sodium bicarbonate ($NaHCO_3$) as the alkaline salt.

In another embodiment, the disclosed compositions include one or more metabolic acid inducer. The metabolic acid inducer is administered with the alkaline salt to prevent systemic alkalization. Metabolic acid inducers do not largely affect stomach pH when taken orally, but when absorbed and metabolized by the liver, their metabolisms require the use of $HCO_3$. Without being bound by any particular theory, it is believed that, by administering the acid inducer in equimolar amounts to $HCO_3$, the $HCO_3$ absorbed in the stomach is utilized in the metabolism of the acid inducers before the $HCO_3$ can enter the blood stream (since all blood from the gut flows to the liver first through the portal circulation). Hence, the combination of the alkaline salt and the metabolic acid inducer allows for selective alkalization of the pH of the stomach and long term activation of the vagal response in the absence of systemic internal alkalization.

In some embodiments, the metabolic acid inducer contemplated by the present invention is an amino acid, ammonium ($NH_4^+$), or any combination thereof. In one embodiment, the metabolic acid inducer includes at least one amino acid. Preferred amino acids include sulfur containing amino acids (cystine, methionine) and cationic amino acids (lysine, arginine, histidine). For example, the metabolic acid inducer may be methionine. In other embodiments, the metabolic acid inducer may be ammonium ($NH_4^+$).

The disclosed compositions also advantageously exhibit improved buffering capacity. The term, "buffering capacity," refers generally to the ability of a liquid to resist changes in pH.

A 0.1M $NaHCO_3$ solution has 10,000 μmoles of $HCO_3$ in 100 mL of solution. If added to the stomach (estimate ~100 mL of pH 2 solution (1000 µmoles of H+)) this would bring stomach pH to close to the pH of the $HCO_3$ solution. The stomach would then have to secrete another 9000 µmoles of $H^+$ to bring stomach pH back to neutral, and another 1000 µmoles to bring it back to pH 2. Because $NaHCO_3$ acts as a buffer, pH would remain in the alkaline range until most of the $HCO_3$ reacts with new acid. This is truer for the stomach where the $HCO_3$ converted to acid ($CO_2$) may be released as gas.

In comparison to alkaline water 1.6 moles of $KHCO_3$ in 100 mL has an initial pH of 8-10, it would not greatly change stomach pH as it would only react with 1.6 of 1000 µmoles of H+ in the stomach and require secretion of 1.6 µmoles of H+ to bring pH back to 2.

Thus, the buffering capacity of the disclosed compositions is a marked improvement over the buffering capacity of alkaline water products. For example, the disclosed compositions exhibit at least 4,000 times more buffering capacity than alkaline water products. In another embodiment, the disclosed compositions exhibit at least 5,000 times, for example, 6,000 times, more buffering capacity than alkaline water products.

A. Pharmaceutical Compositions

Pharmaceutical compositions including one or more alkaline salts and one or more metabolic acid inducers are provided. In general, pharmaceutical compositions are provided including effective amounts of one or more alkaline salts and one or more metabolic acid inducers, and optionally pharmaceutically acceptable diluents, preservatives, solubilizers, emulsifiers, adjuvants, excipients, and/or carriers. Pharmaceutical compositions can be formulated for administration by parenteral (for example, intramuscular, intraperitoneal, intravitreally, intravenous (IV), or subcutaneous injection), enteral, transmucosal (for example, nasal, vaginal, rectal, or sublingual), or transdermal routes of administration or using bioerodible inserts including ocular inserts and can be formulated in dosage forms appropriate for each route of administration.

In some in vivo approaches, the compositions disclosed herein are administered to a subject in a therapeutically effective amount. As used herein, the term "effective amount" or "therapeutically effective amount" means a dosage sufficient to treat, inhibit, or alleviate one or more symptoms of the disease being treated or to otherwise provide a desired pharmacologic and/or physiologic effect. The precise dosage will vary according to a variety of factors such as subject-dependent variables (for example, age, immune system health, etc.).

In this aspect, the selected dosage depends upon the desired therapeutic effect, on the route of administration, and on the duration of the treatment desired. However, for the disclosed compositions, generally dosage levels of about 2 grams are administered to mammals. In some embodiments, the disclosed compositions may be administered to a subject in a dosage level of 0.66 grams delivered three times per day. Generally, for intravenous injection or infusion, the dosage may be lower.

In some embodiments, the compositions disclosed herein are administered in combination with one or more additional active agents, for example, small molecules or mAB. The combination therapies can include administration of the active agents together in the same admixture, or in separate admixtures. Therefore, in some embodiments, the pharmaceutical composition includes two, three, or more active agents. The pharmaceutical compositions can be formulated as a pharmaceutical dosage unit, referred to as a unit dosage form. Such compositions typically include an effective amount of one or more of the disclosed compounds. The different active agents can have the same or different mechanisms of action. In some embodiments, the combination results in an additive effect on the treatment of the disease or disorder. In some embodiments, the combinations result in a more than additive effect on the treatment of the disease or disorder.

In certain embodiments, the disclosed compositions are administered locally, for example, by injection directly into a site to be treated (for example, into a tumor). In other embodiments, the compositions are injected or otherwise administered directly into the vasculature onto vascular tissue at or adjacent to the intended site of treatment (for example, adjacent to a tumor). Typically, the local administration causes an increased localized concentration of the composition which is greater than that which can be achieved by systemic administration.

1. Formulations for Parenteral Administration

In some embodiments, the compositions disclosed herein are formulated for parenteral injection, for example, in an aqueous solution. The formulation may also be in the form of a suspension or emulsion. As discussed above, pharmaceutical compositions are provided including effective amounts of one or more alkaline salts and one or more metabolic acid inducers, and optionally pharmaceutically acceptable diluents, preservatives, solubilizers, emulsifiers, adjuvants, excipients, and/or carriers. Such compositions may optionally include one or more of the following: diluents, sterile water, buffered saline of various buffer content (for example, Tris-HCl, acetate, phosphate), pH and ionic strength, ionic liquids, and HPBβCD; and additives such as detergents and solubilizing agents (for example, TWEEN®20 (polysorbate-20), TWEEN®80 (polysorbate-80)), anti-oxidants (for example, ascorbic acid, sodium metabisulfite), and preservatives (for example, Thimersol, benzyl alcohol) and bulking substances (for example, lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Enteral Administration

In some embodiments, the disclosed compositions are formulated for enteral administration including oral, sublingual, and rectal delivery. In one embodiment, the disclosed compositions are administered in solid dosage form. Suitable solid dosage forms include tablets, capsules, pills, solutions, suspensions, syrups, lozenges, cachets, pellets, powders, or granules or incorporation of the material into particulate preparations of polymeric compounds such as polylactic acid, polyglycolic acid, or into liposomes.

In another embodiment, the disclosed compositions are administered in liquid dosage form. Examples of liquid dosage forms for enteral administration include pharmaceutically acceptable emulsions, solutions, suspensions, and syrups, which may contain other components including inert diluents; preservatives; binders; stabilizers; adjuvants such as wetting agents, emulsifying and suspending agents; and sweetening, flavoring, and perfuming agents. In one embodiment, the disclosed compositions are formulated in a solution. For example, effective amounts of one or more alkaline salts and one or more metabolic acid inducers may be formulated in solution for oral intake.

In this aspect, the alkaline salt should be present in the solution in an effective amount to promote activation of cardiovascular and anti-inflammatory pathways associated with vagal efferent pathways. For example, when the disclosed compositions are formulated in solution, the present invention contemplates a dose of about 0.01M to about 0.5M of the alkaline salt. In another embodiment, when the disclosed compositions are formulated in solution, the present invention contemplates a dose of about 0.05M to about 0.3M of the alkaline salt. In still another embodiment, when the disclosed compositions are formulated in solution, the present invention contemplates a dose of about 0.1M of the alkaline salt.

In some embodiments, the metabolic acid inducer is formulated in solution with the alkaline salt. In this aspect, the metabolic acid inducer and the alkaline salt should be present in the solution in equimolar amounts. As used herein, "equimolar" refers to an equal number of moles or having an equal molar concentration. For example, if the molar concentration of the alkaline salt in the solution is about 0.1M, the molar concentration of the metabolic acid inducer in the solution should also be about 0.1M.

Controlled release oral formulations, for example, delayed release or extended release formulations, may also be desirable. For example, the disclosed compounds may be encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings (for example, delayed release or extended release coatings) prior to incorporation into the finished dosage form. In still another embodiment, the disclosed compounds may be dispersed in a matrix material, which gels or emulsifies upon contact with an aqueous medium. Such matrices may be formulated as tablets or as fill materials for hard and soft capsules.

For enteral formulations, the location of release may be the stomach, the small intestine (the duodenum, the jejunum, or the ileum), or the large intestine. In some embodiments, the release will avoid the deleterious effects of the stomach environment, either by protection of the agent (or derivative) or by release of the agent (or derivative) beyond the stomach environment, such as in the intestine. To ensure full gastric resistance, a coating impermeable to at least pH 5.0 is essential. Examples of common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™ cellulose acetate phthalate (CAP), Eudragit L™, Eudragit S™, and Shellac™. These coatings may be used as mixed films.

III. Methods of Use

The disclosed compositions can be used, for example, to treat or prevent inflammation, an inflammatory response, or an autoimmune disorder, to inhibit or reduce one or more inflammatory M1 macrophages and/or one or more inflammatory neutrophils in the blood, to promote polarization of macrophages from a pro-inflammatory M1 state to an anti-inflammatory M2 state, to treat or prevent cardiovascular disease or metabolic disorders, and to stimulate vagal nerve efferent pathways.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or an average determined from measuring the symptom, pharmacologic, or physiologic indicator in one or more subjects that do not have the disease or condition to be treated (for example, healthy subjects). In some embodiments, the effect of the treatment is compared to a conventional treatment that is known in the art. For example, if the disease to be treated is cancer, the conventional treatment could be a chemotherapeutic agent.

A. Methods of Reducing Inflammation

Methods of using the disclosed compositions to treat or prevent inflammation in a subject are provided. Methods typically include administering a subject in need thereof an effective amount of a composition including one or more alkaline salts and one or more metabolic acid inducers.

In one embodiment, the present invention provides methods of treating an inflammatory response and/or an autoimmune disorder in a subject in need thereof. For example, the disclosed methods can be used to prophylactically or therapeutically inhibit, reduce, alleviate, or permanently reverse inflammation of an inflammatory response or autoimmune disorder. In some embodiments, the disclosed compositions are effective in treating chronic inflammation or chronic inflammatory conditions. The term "chronic inflammation" as used herein refers to constantly recurring inflammation or inflammation that lasts for more than three months. An inflammatory response or autoimmune disorder can be inhibited or reduced in a subject by administering to the subject an effective amount of the disclosed compositions.

In some embodiments, the disclosed compositions may be used to treat or prevent inflammatory conditions associated with vagal nerve efferent pathways. Without being bound by any particular theory, it is believed that the anti-inflammatory effects of the disclosed compositions are likely mediated by activation of the vagal cholinergic anti-inflammatory pathway. The cholinergic anti-inflammatory pathway has been reported to be the efferent arm of the anti-inflammatory reflex (Rosas-Ballina, M. et al. *J Intern Med* 265:663-679 (2009)), which acts via vagal efferents to promote M2 macrophage polarization in the spleen and limit activation of the innate immune system, thereby preventing damage caused by excessive cytokine production. An inflammatory response associated with vagal nerve efferent pathways can be inhibited or reduced in a subject by administering to the subject an effective amount of the disclosed compositions.

Representative inflammatory conditions and autoimmune diseases that can be inhibited or treated by the disclosed compositions include, but are not limited to, rheumatoid arthritis, osteoarthritis, progressive systemic sclerosis, inflammatory bowel disease, idiopathic pulmonary fibrosis, sarcoidosis, hypersensitivity pneumonitis, chronic bronchitis, emphysema, or asthma, pelvic inflammatory disease, Legionella, Lyme disease, Influenza A, Epstein-Barr virus, encephalitis, systemic lupus erythematosus, alopecia areata, anklosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, chronic renal failure, chronic kidney disease, cicatricial pemphigoid, cold agglutinin disease, Crest syndrome, Crohn's disease, cystic fibrosis, Dego's disease, dermatitis dermatomyositis, dermatomyositis juvenile, discoid lupus, essential mixed cryoglobulinemia, fibromyalgia—fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type 1), Type 2 diabetes, juvenile arthritis, Meniere's disease, mixed connective tissue disease, multiple sclerosis, myasthenia gravis, pancreatitis, pemphigus vulgaris, pernicious anemia, polyarteritis nodosa, polychondritis, polyglancular syndromes, polymyalgia rheumatica, polymyositis and dermatomyositis, pneumonia, primary agammaglobulinemia, primary biliary cirrhosis, psoriasis, Raynaud's phenomenon, Reiter's syndrome, rheumatic fever, sarcoidosis, scleroderma, sepsis, septicemia, Sjogren's syndrome, stiff-man syndrome, Takayasu arteritis, temporal arteritis/giant cell arteritis, ulcerative colitis, uveitis, vasculitis, vitiligo, and Wegener's granulomatosis.

In one embodiment, the disclosed compositions can inhibit or treat chronic kidney disease. In another embodiment, the disclosed compositions can inhibit or treat rheumatoid arthritis. In still another embodiment, the disclosed compositions can inhibit or treat inflammatory bowel disease (IBD), Crohn's disease, or ulcerative colitis.

In some embodiments, the present invention provides methods of using the disclosed compositions to inhibit or reduce one or more inflammatory M1 macrophages and one or more inflammatory neutrophils in the blood. The disclosed compositions are administered to a subject in an effective amount to reduce the levels or quantity of the inflammatory M1 macrophages and/or inflammatory neutrophils. In some embodiments, the disclosed compositions lead to direct, and/or indirect reduction of inflammatory M1 macrophages and/or inflammatory neutrophils by 5%, 10%, 20%, 30%, 40%, 50%, 60%, 70%, 80%, 90%, or more than 90%.

In other embodiments, the present invention provides methods of using the disclosed compositions to promote polarization of macrophages from a pro-inflammatory M1 state to an anti-inflammatory M2 state. In other words, the disclosed compositions cause an increase in anti-inflammatory M2 macrophages and a decrease in inflammatory M1 macrophages. This can be indicated by changes in the levels of factors that are associated with M1 and M2 macrophages (for example, levels of TNFα expressing macrophages (M1-polarized macrophages) and IL-10 expressing macrophages (M2-polarized macrophages)). In this aspect, the disclosed compositions are administered to a subject in an effective amount to promote M1 to M2 polarization.

In still other embodiments, the present invention provides methods of using the disclosed compositions to treat or prevent inflammatory conditions caused by one or more pro-inflammatory cytokines. Exemplary pro-inflammatory cytokines include IL1α, IL1β, IL6, and TNFα. In some embodiments, the disclosed compositions are administered to a subject in an effective amount to reduce the expression levels of one or more pro-inflammatory cytokines, reduce the activities of one or more pro-inflammatory cytokines, reduce the secretion of one or more pro-inflammatory cytokines, reduce the ratio of pro-inflammatory cytokines to anti-inflammatory cytokines, or a combination thereof. Typically, the disclosed compositions are effective in reducing the activity and/or quantity of one or more pro-inflammatory cytokines in one or more cell types, for example, in both keratinocytes and macrophages. In some embodiments, the disclosed compositions lead to direct, and/or indirect reduction of one or more pro-inflammatory cytokines by 5%, 10%, 20%, 30%, 40%, 50%, 60%, 70%, 80%, 90%, or more than 90%.

B. Methods of Treating Cardiovascular Disease and Metabolic Disorders

Methods of using the disclosed compositions to treat or prevent cardiovascular disease or metabolic disorders in a subject are provided. For example, in some embodiments, the disclosed compositions can be used to improve vascular endothelial function. Methods typically include administering a subject in need thereof an effective amount of a composition including one or more alkaline salts and one or more metabolic acid inducers.

In one embodiment, the present invention provides methods of treating a cardiovascular disease and/or a metabolic disorder in a subject in need thereof. For example, the disclosed methods can be used to prophylactically or therapeutically alleviate, reduce, or inhibit one or more symptoms or physiological aspects of a cardiovascular disease or metabolic disorder. A cardiovascular disease or metabolic disorder can be inhibited or reduced in a subject by administering to the subject an effective amount of the disclosed compositions.

Representative cardiovascular diseases and metabolic disorders that can be inhibited or treated by the disclosed compositions include, but are not limited to, atherosclerosis, obesity, type 2 diabetes, insulin resistance, endocrine disease, hypertension, and lupus.

In one embodiment, the disclosed compositions can inhibit or treat atherosclerosis. In another embodiment, the disclosed compositions can treat obesity. In still another embodiment, the disclosed compositions can inhibit or treat type 2 diabetes.

C. Methods of Stimulating Vagal Nerve Efferent Pathways

Methods of using the disclosed compositions to stimulate the vagal nerve efferent pathways in a subject are provided. As discussed above, in one embodiment, the disclosed compositions activate vagal nerve efferent pathways and promote anti-inflammatory and cardiovascular protective effects through alkalization of the pH of the stomach. In this aspect, to stimulate or activate the vagal nerve efferent pathways, the disclosed compositions are administered a subject in need thereof in an effective amount to alkalinize the stomach. As known to those of ordinary skill in the art, the pH of the stomach in a human is about 1.5 to 3.5. The term "alkalinize" as used herein refers to making the environment of the stomach more basic, for example, increasing the pH of the environment. In one embodiment, the disclosed compositions increase the pH of the stomach to at least 6-9. In another embodiment, the disclosed compositions increase the pH of the stomach to at least 6-9. Methods typically include administering a subject in need thereof an effective amount of a composition including one or more alkaline salts and one or more metabolic acid inducers.

In some embodiments, the present invention also provides methods of preventing systemic alkalization (i.e., alkalization of the blood) in a subject in need thereof. Typically, the disclosed compositions are effective in preventing and reducing alkalization of the blood upon alkali loading. In other embodiments, the disclosed compositions are effective in preventing and reducing side effects associated with systemic alkalization. For example, the disclosed compositions are effective in preventing and reducing hypercapnia, hypokalemia, kidney stones, and high blood pressure.

D. Co-Therapies

In one embodiment, the disclosed compositions can be administered to a subject in need thereof in combination with: an antimicrobial such as an antibiotic, or an antifungal, or an antiviral, or an antiparasitic, or an essential oil, or a combination thereof.

The disclosed compositions can be administered to a subject in need thereof in combination or alternation with other therapies and therapeutic agents. In some embodiments, the disclosed compositions and the additional therapeutic agent are administered separately, but simultaneously, or in alternation. The disclosed compositions and the additional therapeutic agent can also be administered as part of the same composition. In other embodiments, the disclosed compositions and the second therapeutic agent are administered separately and at different times, but as part of the same treatment regime.

1. Treatment Regimes

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. The disclosed compositions can be the first or the second therapeutic agent.

The disclosed compositions and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary molecules include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the disclosed compositions can be co-administered with one or more additional agents that function to enhance or promote an immune response or reduce or inhibit an immune response.

2. Antimicrobials

One embodiment provides the disclosed compositions and an antimicrobial agent and methods of their use. For example, the disclosed compositions can be used in a preventive or prophylactic role in the treatment and prevention of disease as discussed above.

In some embodiments, the subject is administered the disclosed compositions and/or the antimicrobial at time of admission to the hospital to prevent further bacterial, fungal or viral complications. The antibiotic can target pathogens and the disclosed compositions can stimulate the immune system to provide an enhanced response to treat or prevent further infection or disease.

3. Immunomodulators a. PD-1 Antagonists

In some embodiments, the disclosed compositions are combined with or co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MHC) (see, for example, Freeman, *Proc. Natl. Acad. Sci. U. S. A*, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos: 7,332,582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., Clin. Cancer Res., 14:30443051 (2008).

Exemplary anti-B7-H1 (also referred to as anti-PD-L1) antibodies include, but are not limited to, those described in the following U.S. Pat Nos: 8,383,796, 9,102,725, 9,273,135, 9,393,301, and 9,580,507, all of which are specifically incorporated by reference herein in their entirety.

For anti-B7-DC (also referred to as anti-PD-L2) antibodies see US Pat. Nos.: 7,411,051, 7,052,694, 7,390,888, 8,188,238, and 9,255,147, all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., *Immunity*, Vol. 27, pp. 111-122, (2007)). Such fragments also include the soluble ECD portion of the PD-1 protein that includes mutations, such as the A99L mutation, that increases binding to the natural ligands (Molnar et al., *PNAS*, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

b. CTLA4 Antagonists

In some embodiments, the disclosed compositions are combined with or co-administered with one or more CTLA4 antagonists, for example an antagonistic anti-CTLA4 antibody. An example of an anti-CTLA4 antibody contemplated for use in the methods of the invention includes an antibody as described in U.S. Pat. No. 9,487,581

Dosages for anti-PD-1, anti-B7-H1, and anti-CTLA4 antibody, are known in the art and can be in the range of, for example, 0.1 mg/kg to 100 mg/kg, or with shorter ranges of 1 mg/kg to 50 mg/kg, or 10 mg/kg to 20 mg/kg. An appropriate dose for a human subject can be between 5 mg/kg and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., *Clinical Kidney Journal*, 3(2):135-137 (2010), published online December 2009.

In other embodiments, the antagonist is a small molecule. A series of small organic compounds have been shown to bind to the B7-1 ligand to prevent binding to CTLA4 (see Erbe et al., *J. Biol. Chem.*, 277:7363-7368 (2002). Such small organics could be administered alone or together with an anti-CTLA4 antibody to reduce inhibitory signal transduction of T cells.

c. Potentiating Agents

In some embodiments, the compositions are combined with or administered with a potentiating agent. The potentiating agent acts to increase the efficacy of the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, Huang M, Duan W, Yu XQ, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(-)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke *Crit Rev. Immunol.* 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al. *Cancer Immunol. Immunother.* 58:1219-1228 (2009). A similar result was observed in the HHD2 tumor model: adoptive transfer of CD4+CD25+ Treg after CTX pretreatment eliminated therapeutic response to vaccine (Taieb, J. *J. Immunol.* 176:2722-2729 (2006)).

Numerous human clinical trials have demonstrated that low dose CTX is a safe, well-tolerated, and effective agent for promoting anti-tumor immune responses (Bas, & Mastrangelo *Cancer Immunol. Immunother.* 47:1-12 (1998)).

The optimal dose for CTX to potentiate an anti-tumor immune response, is one that lowers overall T cell counts by lowering Treg levels below the normal range but is sub-therapeutic (see Machiels et al. Cancer Res. 61:3689-3697 (2001)).

In human clinical trials where CTX has been used as an immunopotentiating agent, a dose of 300 mg/m$^2$ has usually been used. For an average male (6 ft, 170 pound (78 kg) with a body surface area of 1.98 m$^2$), 300 mg/m$^2$ is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al. *Cancer Res.* 61:3689-3697 (2001), Hengst et al *Cancer Res.* 41:2163-2167 (1981), Hengst *Cancer Res.* 40:2135-2141 (1980)).

For larger mammals, such as a primate, such as a human, patient, such mg/m$^2$ doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g. Avastin, VEGF-Trap) (see, for example, Li et al., Vascular endothelial growth factor blockade reduces intratumoral regulatory T cells and enhances the efficacy of a GM-CSF-secreting cancer immunotherapy. Clin Cancer Res. 2006 Nov. 15; 12(22):6808-16.), anthracyclines, oxaliplatin, doxorubicin, TLR4 antagonists, and IL-18 antagonists.

d. Anti-Inflammatories

The disclosed compositions may also be administered with one or more anti-inflammatory agents. The anti-inflammatory agent can be non-steroidal, steroidal, or a combination thereof. One embodiment provides oral compositions containing about 1% (w/w) to about 5% (w/w), typically about 2.5% (w/w) of an anti-inflammatory agent. Representative examples of non-steroidal anti-inflammatory agents include, without limitation, oxicams, such as piroxicam, isoxicam, tenoxicam, sudoxicam; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents may also be employed.

Representative examples of steroidal anti-inflammatory drugs include, without limitation, corticosteroids such as hydrocortisone, hydroxyl-triamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

EXAMPLES

Example 1

Oral NaHCO$_3$ Activates a Splenic Cholinergic Anti-Inflammatory Pathway Via Fragile Connections to the Splenic Mesothelium In Example 1, flow cytometry as well as mRNA markers in isolated splenic macrophages were utilized to determine whether oral NaHCO$_3$ intake promotes M2 macrophage polarization in the kidney and spleen in both hypertensive Dahl salt-sensitive (SS) rats, in which significant inflammation is known to be present (De Migual, C. et al. *Curr Hypertens Rep* 17:507 (2014)), as well as normotensive Sprague Dawley rats, in which baseline renal inflammation has been reported to be low. The effect of acute oral NaHCO$_3$ loading on inflammatory cell profiles in the blood of healthy human subjects was also investigated. Further, as it was found that gentle manipulation to visualize the spleen at midline during surgical laparotomy (sham splenectomy) was sufficient to abolish the anti-inflammatory response to oral NaHCO$_3$, the pathways through which vagal efferent signals stimulated by oral NaHCO$_3$ may be transmitted to the splenic parenchyma were investigated.

Methods and Materials

Rat Studies

Animals: Studies used 8-12 week old male Dahl SS or Sprague Dawley rats (Charles River laboratories; 357 Wilmington Mass.). Rats were maintained ad libitum on water and a pellet diet containing low 0.4% NaCl (AIN76A; Dyets Inc; Bethlehem Pa.; (low salt 0.4% NaCl)). Rats were age matched for all protocols. All studies were conducted in accordance with the National Institutes of Health (NIH) Guide for the Care and Use of Laboratory Animals. All of the protocols were approved in advance by the institutional animal care committee at Augusta University.

Sub diaphragmatic transection of the vagal nerves: Rats were anesthetized with isoflurane (2-5%) and a midline incision performed. Using a stereoscope, the vagal nerves were visualized immediately below the diaphragm and transected. Any nervous tissue around the esophagus was also cleared by dissection. When visualizing the esophagus, care was taken to limit any horizontal movement of the stomach and to avoid movement of the spleen. After wound closure animals were allowed to recover for two weeks before tissue was harvested under isoflurane anesthesia. Bloating of the stomach was used to confirm sub diaphragmatic transection of the vagal nerves.

Visualization of the spleen at midline/sham splenectomy: Dahl salt-sensitive rats were anesthetized with isoflurane (2-5%) and a midline incision performed. The spleen was located and gently moved toward the incision site by hand or with cotton tip applicators. The poles of the spleen were visualized and the spleen returned to its original position. Following the surgical procedure rats were allowed to recover for 7 days before entering the high salt protocol described below.

Arterial blood gas measurements: Dahl SS rats were anesthetized (2-5% isoflurane) and the left femoral artery was catheterized. Surgically implanted catheters were then tunneled under the skin and exposed between the shoulder blades. Catheters were protected by a light wire spring attached to a swivel (Instech Laboratories Inc, Plymouth Meeting, Pa.), which allows free 360-degree movement of the animal. Rats were individually housed and allowed to recover for 1 week before beginning experimental measurements. Catheters were filled with heparinized saline (30 U/mL) and connected to an infusion pump (Phd2000, Harvard Apparatus, Holliston, Mass.). Infusions of heparinized saline were maintained at 100 µL/hr over the course of the protocol. 0.2 mL arterial blood samples were taken prior to placing rats on treated water, on day 3 of low salt feeding and on day 7 of high salt feeding by disconnecting the catheter from the infusion pump proximal to emergence of the catheter from the rat and drawing arterial blood into a heparinized 1 mL syringe. Arterial blood gas measurements were performed on a Rapidpoint 4055 Blood gas analyzer (Seimens AG, Munich Germany) within 20 minutes of taking the sample. Arterial blood gas measurements on day 14 of HS feeding were taken at the time of sacrifice by left ventricular puncture in anesthetized (2-5% isoflurane) rats.

Flow cytometry: With the exception of one group of rats (n=5+5), in all HS fed Dah SS rats, blood pressure telemetry devices were implanted prior to beginning the study. All protocols were initiated at least 7 days after surgery to allow time for rats to recover and no significant differences in flow cytometry results were observed between rats that had telemeters implanted compared to rats without prior surgery. No surgical procedures were performed on LS fed Dahl SS rats or Sprague Dawley rats prior to tissue harvest. On the day of tissue harvest rats were anesthetized with isoflurane (2-5%) and a midline incision was performed. The abdominal aorta was catheterized for the collection of ~2mL of arterial blood in a heparinized tube and the left kidney excised and immediately processed for flow cytometry. Antibody markers utilized for flow cytometry as well as references are given in the online methods.

To identify and evaluate immune cells in renal and splenic tissues, we employed a flow cytometry-based assay. Briefly, kidneys were harvested and placed in RPMI (Thermo Fischer laboratories Inc)+10% FBS (Atlanta biologicals, Lawrenceville, Ga.), minced, and single cell suspensions were achieved using a 100 µM cell strainer (BD Biosciences, San Diego, Calif.) followed by centrifugation (1,400 rpm, 5 min) and lysis of erythrocytes by incubation with ACK lysing buffer (3 minutes at room temp; Quality Biological, Gathersburg, Md.). Spleens were harvested and placed in RPMI+ 10% FBS. Spleens were then injected with 1 mL of 100 CD units/ml Collagenase IV (Sigma, St. Louis, Mo.) solution in 3 regions then placed in 1 ml of 400 CD units/ml Collagenase IV, incubated at 37° C. for 30 minutes and minced. Single-cell suspensions were then achieved as described for the kidney and all cells were washed twice (PBS).

In all flow studies, cells were then incubated with antibodies for surface markers for 20 minutes on ice in the dark (all antibodies from Pharmingen-BD-Biosciences, San Jose, Calif.). Cells were then washed with PBS, fixed and permeabilized using FOXP3/Transcription Factor Fix/Perm Buffer (eBiosciences, San Diego, Calif.) for 15 minutes in the dark on ice, and washed once again with PBS before incubation with antibodies for intracellular staining of Foxp3, TNFa, IL-10, and IL-17, on ice in the dark for 20 minutes (BD Biosciences). Cells were then washed and run through a four-color flow cytometer (FACS Calibur, Becton-Dickinson), and data were collected using CellQuest software.

In all flow studies, group identifiers were removed and flow cytometry analysis was performed by an investigator unaware of the hypothesis or the origin of samples. Samples were double-stained with control IgG and cell markers and were used to assess any spillover signal of fluorochromes; proper compensation was set to ensure the median fluorescence intensities of negative and positive cells were identical and were both gated populations. Gating was used to exclude dead cells and debris using forward and side scatterplots. In each analysis, 100,000 total events were collected. As a gating strategy, for each sample, isotype-matched controls were analyzed to set the appropriate gates. For each marker, samples were analyzed in duplicate measurements. To minimize false-positive events, the number of double- positive events detected with the isotype controls was subtracted from the number of double-positive cells stained with corresponding antibodies (not isotype control), respectively. Cells expressing a specific marker were reported as a percentage of the number of gated events.

Verification of macrophage polarization in isolated splenic macrophages: Markers for M1 and M2 macrophages were selected based on previous studies in the rat; however, to confirm the specificity of these markers, in a subset of animals these markers were compared with alternative markers and depletion of kidney cells identified as macrophages was confirmed using clodronate liposomes. In these studies a single dose of clodronate liposomes or liposome controls (Encapsula Nanosciences, Nashville, Tenn.; 20 mg/kg) was injected into the tail vein of rats 24 and 72 hours prior to harvesting the kidneys for flow cytometry. In addition, rat spleen macrophages were isolated from Dahl SS rats treated with either NaCl or $NaHCO_3$ for two weeks and fed a high salt (8%) diet. Splenic macrophages were isolated by centrifugation in a Percoll density gradient and real-time PCR was performed for rat iNOS, arginase and GAPDH to identify macrophage polarization.

Urinary Analysis:

Urine collection: For urine collection rats were placed in rat metabolic cages for 24 hours (Nalgene, Rochester, N.Y.). Urine was collected and weighed for volume determination. Up to 10 mL of urine was stored at −80° C. for later analysis. All urinary data are presented as 24 hour urinary excretion.

Electrolytes: Urinary Na, K and Cl measurements were obtained using an electrolyte analyzer (Easylite; Medica Co, Bedford Mass.). Samples were diluted 1:10, 1 part urine to 9 parts Easylyte Urine Diluent as per the manufactures instructions.

Titratable acids: Urinary titratable acids were determined with titration of 5 mL of urine with NaOH or HCl to pH 7.4.

$NH_4^+$ excretion: Urinary $NH4^+$ concentration was determined using an ammonia ion selective electrode (Orion high performance ammonia ion selective electrode (Thermo Fischer Scientific Inc)). Urine samples were diluted in Orion ionplus Solution Alkaline Reagent immediately before measurement as per the manufacturer's instructions. Measurements were compared to those of a standard curve using serial dilutions of the Thermo Scientific Orion Application Solution 0.1 M $NH_4^+$ Ammonium Standard. Final concentrations were calculated using a log curve (Graphpad Prism 6; Graphpad software Inc, La Jolla, Calif.).

Electron microscopy: Preparation and imaging of tissue by electron microscopy was performed by the Augusta University Histology core facility. Tissue was fixed in 4% paraformaldehyde, 2% glutaraldehyde in 0.1M sodium cacodylate (NaCac) buffer, pH 7.4, postfixed in 2% osmium tetroxide in NaCac, stained en bloc with 2% uranyl acetate, dehydrated with a graded ethanol series and embedded in Epon-Araldite resin. Thin sections of 75 nm thickness were cut with a diamond knife on a Leica EM UC6 ultramicrotome (Leica Microsystems Inc., Bannockburn, Ill.) collected on copper grids and stained with uranyl acetate and lead citrate. Tissue was observed in a JEM 1230 transmission electron microscope (JEOL USA Inc., Peabody, Mass.) at 110 kV and imaged with an UltraScan 4000 CCD camera and First Light Digital Camera Controller (Gatan Inc., Pleasantonm Calif.).

Histological analysis: Tissue harvest and fixation: At the end of the study, rats were anesthetized with isoflurane (2-5%) and tissues excised and placed in 10% formalin solution (Sigma; St Louis, Mo.) for 48 hours before being paraffin embedded, blocked and processed (Augusta University Core facility). Kidneys were paraffin embedded in an automatic tissue processor and 3-μm cut sections mounted on siliconized/charged slides. The slides were deparaffinized and hydrated and antigen retrieval performed using IHC-Tek Epitope retrieval solution at steaming for 40 min (IHC-World, cat# IW-1100). Tissue was blocked with 3% hydrogen peroxide in methanol for 10 minutes. The goat anti-rabbit IgG-HRP conjugated secondary antibody (Santa-cruz Cat#sc-2004, 400 μg/ml, 1:400 at 1 μg/ml) was used for 30 minutes at room temperature. The slides were stained with Betazoid DAB Chromogen Kit (Biocare Medical Cat# BDB2004H). Omitting the first antibody served as a negative control and resulted in no positive staining in tissue. All end-point analysis was blinded to the investigators. For histological scoring all identifiers were removed and slides given a number before being scored by an investigator that was unaware of the hypothesis being tested or source of each slide. Data were then compiled by the primary investigator who had access to the numbering key.

$Ca^{2+}$ imaging: Untreated rats were anesthetized with isoflurane (2-5%) and the spleen excised. The spleen was placed in Hanks Balanced salt-solution with 20 mM HEPES buffer pH 7.40 at room temperature with Fluo4. Imaging acquisition was conducted using the Andor Revolution system (Andor Technology Belfast, UK)(38). A Nikon microscope (Eclipse FN 1, Nikon, Tokyo, Japan) was connected to a laser confocal spinning unit (CSU-X1, Yokogawa, Tokyo, Japan) attached to a Sutter filter wheel and an ultrasensitive EMCCD camera (iXonEM, Andor Technology, Belfast, UK). The microscope chamber was continuously perfused, at a rate of 2-3 ml/min, with Hanks Balanced salt solution pH 7.4 (HBSS) using a peristaltic pump (Miniplus 3, Gilson, Middleton, Wis.). Chamber temperature was maintained at 36±1° C. using a single line solution heater (SH-28B, Warner Instruments, Hamden, Conn.) connected to a DC power supply (1735A, BK Precision, Yorba Linda, Calif.). Calcium imaging experiments were monitored from thick spleen slices incubated at room temperature (RT) in HBSS containing 5 μM Fluo-4 AM and pluronic acid (2.5 μg/ml). Following an hour incubation period, slices were placed in RT HBSS until needed. Fluorescence images were obtained using a krypton/argon laser (488 nm excitation and >495 nm emission). Images were acquired at ~0.7 frames/sec. 40× or 20× Nikon dipping objectives were used to visualize the spleen surface during electrical stimulation.

Rat protocols: Dahl SS rats: All rats were maintained on low salt chow with ad libitum water (tap water). Following 7 days recovery from surgery, on day 1 of the high salt diet (HS) protocol, tap water was replaced with either 0.1M $NaHCO_3$ (n=11; Sigma) or equimolar NaCl (0.1M) made fresh daily also ad libitum (n=10). $NaHCO_3$ or vehicle treated water was then maintained for the remainder of the protocol. Following four days of low salt (LS) feeding, rats were placed on an 8% HS diet (AIN76A 8%; Dyets) for two weeks. 24 hour urine collections were obtained on day 3 of low salt and day 7 and day 14 of high salt feeding if applicable. Following 14 days of HS feeding, rats were anesthetized with isoflurane (2-5%) and tissue harvested for analysis.

Blood gas/electrolytes: In a parallel study, rats were implanted with a femoral arterial catheter to allow arterial blood sampling. Arterial blood samples were taken on day 0, prior to switching of the drinking water to either $NaHCO_3$ (n=9) or NaCl (n=9), day 3 of low salt feeding and at day 7 and 14 of high salt feeding.

Dahl SS rats on the LS protocol were treated identically to the HS protocol above except following 4 days of LS rats were anesthetized and tissue harvested for flow cytometric analysis prior to beginning a HS diet. N=5/5 for NaCl and $NaHCO_3$ treatment respectively.

Sub diaphragmatic transection of the vagal nerves: Following surgical laparotomy and sub diaphragmatic transection of the vagal nerves, 5 surgical sham control rats and 5 rats in which the vagal nerves were transected were allowed to recover for 14 days prior to tissue harvest.

Visualization of the spleen at midline/sham splenectomy: Dahl SS rats in which the spleen was removed (n=5/7 for vehicle and $NaHCO_3$ treatment, respectively) or moved to midline during surgery (sham splenectomy (n=5/5 for vehicle and $NaHCO_3$ treatment, respectively)) were entered into the HS protocol described above prior to tissue sacrifice. An additional sham control group (laparotomy only) was performed to control for movement of the spleen (n=4/5 for vehicle and $NaHCO_3$ treatment, respectively). Tissue collected from animals in this group was utilized to compare antibody sets for identification of macrophage polarization (as shown in panels a-d of FIG. 21).

Dose response studies in Sprague Dawley rats: Rats were maintained on standard laboratory chow (Teklad) and placed on either 0.1M $NaHCO_3$, 0.05M NaCl/0.05M $NaHCO_3$, 0.09M NaCl/0.01 $NaHCO_3$ or 0.1M NaCl for 4 days before prior to tissue harvest (n=3 animals were utilized at each dose).

Human Studies

Participants: To examine the effects of $NaHCO_3$ on acute changes in parasympathetic activity (PSA), 12 healthy participants (6 men, 6 women, age 27±2 y, BMI 25.3±1.2 kg/m$^2$) were provided 2 g of $NaHCO_3$ dissolved in 250 ml of bottled water (treatment [TXT] group). An additional 6 participants (4 men, 2 women, age 25±1, BMI 25.7±2.1 kg/m$^2$) were recruited as controls and were provided 1.39 g of NaCl (equivalent molar load to 2 g of $NaHCO_3$) dissolved in 250 ml of bottled water (control [CON] group).

Serum Electrolytes: Blood samples were collected via an intravenous catheter (Nexiva™ Becton Dickinson, Franklin Lakes, N.J.) at baseline and at 60 minute intervals post-treatment to examine changes in serum electrolyte balance (Na, K, and Cl$^-$).

Analytical flow cytometry: In the $NaHCO_3$ treatment group, 10 of 12 subjects had blood drawn at 3 hours post treatment. Blood was taken at all time points for all control subjects. No data was excluded from the analysis. Flow cytometric analysis of heparinized whole blood was performed as described previously. Briefly, cells were incubated with antibodies for surface markers (15 minutes on ice in dark) before incubation with antibodies against intracellular cytokines and factors (after permeabilization for 15 minutes using fix/Perm cocktail, eBioscience, San Diego USA) including, CD11b, CD68, TNFα (for M1 macrophages), CD11b, CD68, CD206 and IL-10 (for M2 macrophages) (purchased from BD BioSciences) and CD16 and TNFα (for neutrophils, from eBioscience, USA). Cells were then washed and run through a four-color flow cytometer (FACS Calibur, BD Biosciences), and data were collected using CellQuest software. Samples were double-stained with control IgG and cell markers to assess any spillover signal of fluorochromes. Proper compensation was set to ensure the median fluorescence intensities of negative and positive cells were identical and then was used to gate the population. Gating excluded dead cells and debris using forward and side scatter plots. To confirm the specificity of primary antibody binding and rule out nonspecific Fc receptor binding to cells or other cellular protein interactions, negative control experiments were conducted using isotype controls matched to each primary antibody's host species, isotype, and conjugation format. The control antibodies had no specificity for target cells within our studies yet retain all the nonspecific characteristics of the antibodies used in the experiments.

Statistics and Analysis: Data were analyzed using Graphpad Prism (Graphpad Inc) software. All data are expressed as mean±SE. Multiple comparisons were analyzed using 2-way ANOVA. All other parametric comparisons were analyzed via unpaired 2-sided Students t-test. Categorical data was analyzed by Fischer's test. Significance was considered p<0.05. All end point analysis was blinded to the investigators. Flow cytometry gating and analysis was performed by an investigator who was unaware of the hypothesis being tested. For histological analysis, group identifiers were removed from samples before analysis and data compiled by the primary investigator once analysis was complete.

Results

Rat Studies

Electrolytes

Plasma electrolytes were measured in high salt fed (8% NaCl chow) Dahl salt-sensitive ("SS") rats. FIGS. 1A-1C show urinary acid excretion in the Dahl SS rats. FIG. 1A shows urinary sodium (Na), FIG. 1B shows urinary potassium (K), and FIG. 1C shows urinary chlorine (Cl). On the x-axis, the 0.4% NaCl column corresponds to 24 hour urine collection at day 7LS, the 8% NaCl (Wk1) column corresponds to 24 hour urine collection at day 7HS, and the 8% NaCl (Wk2) column corresponds to 24 hour urine collection at day 14HS. As can be seen in FIGS. 1A and 1B, addition of $NaHCO_3$ (0.1M) to the drinking water of Dahl SS rats had no effect on urinary Na or K excretion when compared to vehicle (0.1M NaCl), indicating similar Na and K intake across the course of the study. However, as shown in FIG. 1C, urinary Cl excretion was significantly lower (p=0.03) in rats drinking water with $NaHCO_3$, reflecting a large portion of Na intake in these animals was from $NaHCO_3$.

In addition, Table 1 below shows the data from blood gas analysis of arterial blood from Dahl SS rats drinking either 0.1M $NaHCO_3$ (bicarbonate) or equimolar NaCl (vehicle). The abbreviations of Table 1 are as follows: pH, plasma pH; $pCO_2$, arterial blood $pCO_2$ (partial pressure); pO2, arterial blood pO2 (partial pressure); $HCO_3^-$, arterial blood $[HCO_3^-]$ (mM) standard; Hct, arterial blood hematocrit (%); Na, arterial plasma [Na$^+$](mM); K, arterial plasma [K$^+$]l (mM); Cl, arterial plasma [Cl$^-$](mM); glucose, arterial blood [glucose]mg/dL. P is the result of unpaired Students t-test comparing each antibody between vehicle and bicarbonate treated groups. P<0.05 was considered significant*. As shown in Table 1, there was no significant difference in any markers of plasma acid base status (pH, $pCO_2$, $HCO_3^-$) across the course of the study.

TABLE 1

BLOOD GAS ANALYSIS OF ARTERIAL BLOOD FROM DAHL SS RATS

| | Treatment | pH | pCO2 | pO2 | HCO3– | Hct | Na | K | Cl | Glucose |
|---|---|---|---|---|---|---|---|---|---|---|
| Control | Untreated (n = 5) | 7.46 ± 0.00 | 37.4 ± 1.1 | 96.9 ± 2.0 | 26.1 ± 0.5 | 43 ± 1 | 142 ± 1 | 4.12 ± 0.10 | 107 ± 1 | 115 ± 6 |
| Day 3 LS | Vehicle (n = 6) | 7.44 ± 0.01 | 33.5 ± 1.1 | 89.4 ± 2.4 | 23.5 ± 0.6 | 39 ± 0 | 135 ± 3 | 3.74 ± 0.38 | 106 ± 0 | 184 ± 36 |
| | Bicarbonate (n = 8) | 7.43 ± 0.01 | 38.3 ± 1.1 | 93.5 ± 2.4 | 25.2 ± 0.7 | 40 ± 0 | 137 ± 1 | 3.69 ± 0.10 | 112 ± 2 | 195 ± 25 |
| | P | N.S | 0.01* | N.S | N.S (0.1) | N.S | N.S | N.S | 0.006** | N.S |
| Day 7 HS | Vehicle (n = 7) | 7.42 ± 0.03 | 44.3 ± 2.6 | 90.6 ± 14 | 26.8 ± 1.2 | 41 ± 1 | 141 ± 1 | 3.47 ± 0.11 | 106 ± 2 | 226 ± 29 |
| | Bicarbonate (n = 9) | 7.46 ± 0.02 | 39.4 ± 3.2 | 113 ± 16 | 26.9 ± 0.6 | 39 ± 2 | 142 ± 1 | 3.55 ± 0.13 | 106 ± 1 | 160 ± 16 |
| | P | N.S | N.S | N.S | N.S | N.S | N.S | N.S | N.S | N.S |

TABLE 1-continued

BLOOD GAS ANALYSIS OF ARTERIAL BLOOD FROM DAHL SS RATS

| | Treatment | pH | pCO2 | pO2 | HCO3− | Hct | Na | K | Cl | Glucose |
|---|---|---|---|---|---|---|---|---|---|---|
| Day 14 HS | Vehicle (n = 6) | 7.42 ± 0.03 | 42.2 ± 5.3 | 85.5 ± 4.5 | 25.5 ± 0.9 | 42 ± 1 | 146 ± 1 | 3.94 ± 0.20 | 101 ± 2 | 272.5 ± 42 |
| | Bicarbonate (n = 5) | 7.46 ± 0.03 | 37.4 ± 4.9 | 88.7 ± 8.5 | 26.1 ± 1.0 | 41 ± 2 | 145 ± 1 | 3.90 ± 0.19 | 103 ± 3 | 235.4 ± 35 |
| | p | N.S | N.S | N.S | N.S | N.S | N.S | N.S | N.S | N.S |

Inflammatory Profile

Flow cytometry data from blood, spleen, and whole kidney of rats treated with either vehicle or $NaHCO_3$ after 2 weeks of high salt are presented in Table 2 below. Table 2 shows data from 14 day high salt (HS) and 3 day only low salt (LS) fed animals. P is the result of unpaired Students t-test comparing vehicle and bicarbonate treated groups. For all analyses, P<0.05 was considered significant*. Two studies were pooled for HS kidney analysis. In group 1 (n=5+5) blood and kidney samples were analyzed from Dahl SS rats fed a HS diet for 14 days that did not have prior surgery. In group 2 (n=5+6 for vehicle and bicarbonate, respectively) kidney and spleen were analyzed. Blood pressure (telemetry), urine analysis, and histological measurements of injury were all performed in group 2 animals. CD3, IL-17, IL-10, M1, M2, TNFα and CD11b/c positive cells are all expressed as % of total kidney/spleen cells±SE. CD4, CD44, and CD69 positive cells are expressed as % of CD4 positive cells. FOXP3 positive cells are expressed as % of both CD3/CD4 positive cells.

TABLE 2

FLOW CYTOMETRIC ANALYSES OF BLOOD AND KIDNEYS FROM DAHL SS RATS

14 Days HS

| | CD3 (% total kidney) | CD4 (% of CD3) | CD44 (% of CD3) | CD69 (% of CD3) | FOXP3 (% of CD3/CD4) | IL-17 (% of total kidney) | M1 (% of total kidney) | M2 (% of total kidney) | IL-10 (% of total kidney) | TNFα (% of total kidney) | CD11b/c (% total kidney) |
|---|---|---|---|---|---|---|---|---|---|---|---|
| Blood | | | | | | | | | | | |
| Vehicle (n = 4) | 54 ± 1 | 55 ± 2 | 19 ± 2 | 1.2 ± 0.3 | 2.5 ± 0.3 | 8 ± 1 | | | | | |
| Bicarbonate (n = 5) | 57 ± 2 | 53 ± 2 | 14 ± 2 | 0.9 ± 0.3 | 4.4 ± 0.6 | 6 ± 1 | | | | | |
| P | N.S. | N.S. | N.S. | N.S. | 0.02* | N.S. | | | | | |
| Kidney | | | | | | | | | | | |
| Vehicle (n = 10) | 2.1 ± 0.3 | 57 ± 1 | 47 ± 4 | 1.8 ± 0.4 | 1.7 ± 0.3 | 1.1 ± 0.2 | 0.26 ± 0.03 | 0.12 ± 0.02 | 2.8 ± 0.3 | 3.2 ± 0.4 | 0.29 ± 0.04 |
| Bicarbonate (n = 11) | 1.8 ± 0.3 | 55 ± 2 | 36 ± 5 | 2.8 ± 0.7 | 3.3 ± 0.5 | 0.7 ± 0.1 | 0.12 ± 0.02 | 0.2 ± 0.03 | 4.2 ± 0.3 | 2.0 ± 0.3 | 0.4 ± 0.04 |
| P | N.S. | N.S. | N.S. | N.S. | 0.01* | N.S. | 0.001** | 0.04* | 0.048* | 0.03* | N.S. |

3 days LS

| | CD3 | CD4 | CD44 | CD69 | FOXP3 | IL-17 | M1 | M2 | IL-10 | TNFα | CD11b/c |
|---|---|---|---|---|---|---|---|---|---|---|---|
| Blood | | | | | | | | | | | |
| Vehicle (n = 5) | 57 ± 1 | 54 ± 1 | 15 ± 2 | 2.4 ± 0.7 | 4.8 ± 0.8 | 5.4 ± 0.5 | | | | | |
| Bicarbonate (n = 5) | 57 ± 2 | 55 ± 1 | 18 ± 1 | 1.6 ± 0.5 | 5.8 ± 0.7 | 5.6 ± 1.1 | | | | | |
| P | N.S. | N.S. | N.S. | N.S. | N.S. | N.S. | | | | | |
| Kidney | | | | | | | | | | | |
| Vehicle (n = 5) | 1.1 ± 0.2 | 59 ± 1 | 58 ± 1 | 0.9 ± 0.1 | 1.6 ± 0.2 | 1.3 ± 0.5 | 0.30 ± 0.06 | 0.20 ± 0.05 | 3.0 ± 0.5 | 2.4 ± 0.5 | 0.22 ± 0.06 |
| Bicarbonate (n = 5) | 1.1 ± 0.3 | 54 ± 2 | 52 ± 3 | 0.9 ± 0.3 | 2.6 ± 0.5 | 0.4 ± 0.2 | 0.16 ± 0.04 | 0.36 ± 0.02 | 4.8 ± 0.5 | 1.4 ± 0.2 | 0.24 ± 0.02 |
| P | N.S. | 0.02* | N.S. (0.07) | N.S. | N.S. | N.S. | N.S. (0.1) | 0.03* | 0.04* | N.S. (0.11) | N.S. |

14 Days HS

| Spleen | CD3 | CD4 | CD44 | CD69 | FOXP3 | IL-17 | M1 | M2 | IL-10 | TNFα | CD11b/c |
|---|---|---|---|---|---|---|---|---|---|---|---|
| Vehicle (n = 5) | 15.8 ± 0.8 | 57 ± 1 | 40 ± 2 | 5.2 ± 0.7 | 4.2 ± 0.2 | 4.4 ± 0.5 | 8.6 ± 0.7 | 6.4 ± 0.5 | 5.8 ± 0.8 | 5.8 ± 0.8 | 6 ± 0.4 |

TABLE 2-continued

FLOW CYTOMETRIC ANALYSES OF BLOOD AND KIDNEYS FROM DAHL SS RATS

| Bicarbonate (n = 6) | 15.3 ± 0.8 | 53 ± 1 | 35 ± 2 | 7.2 ± 0.9 | 6 ± 0.5 | 2.8 ± 0.6 | 5.8 ± 0.5 | 8.3 ± 0.5 | 7.5 ± 0.7 | 3 ± 0.5 | 7.3 ± 0.6 |
|---|---|---|---|---|---|---|---|---|---|---|---|
| P | N.S. | N.S. (0.06) | 0.04* | N.S. | 0.015* | N.S. (0.08) | 0.01* | 0.02* | N.S. | 0.01* | N.S. |

Figure 2B:
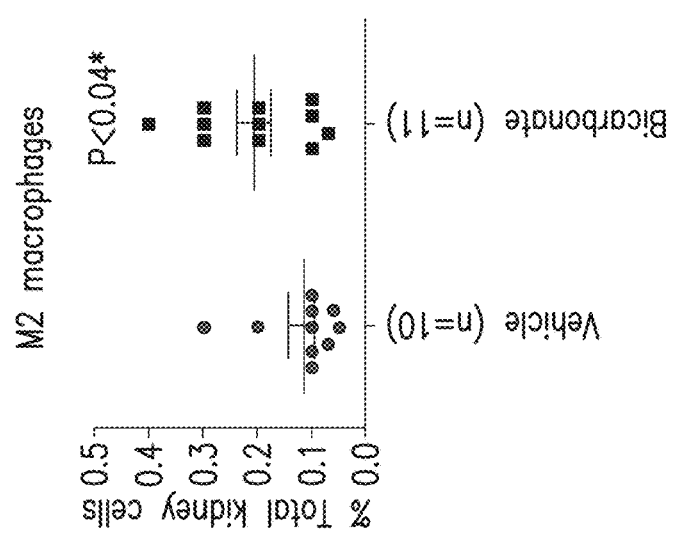
FIG. 2B is a graph showing the percentage of total kidney cells identified as M2 macrophages in vehicle and bicarbonate treated rats.
Figure 2A:
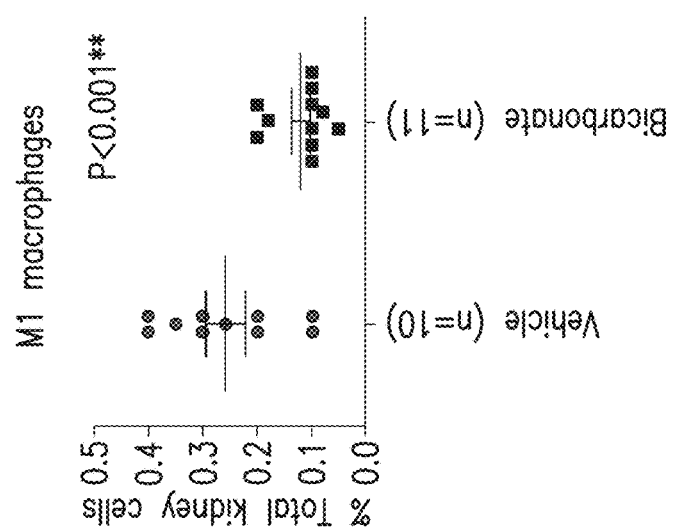
FIG. 2A is a graph showing the percentage of total kidney cells identified as M1 macrophages in vehicle and bicarbonate treated rats.
Figure 2F:
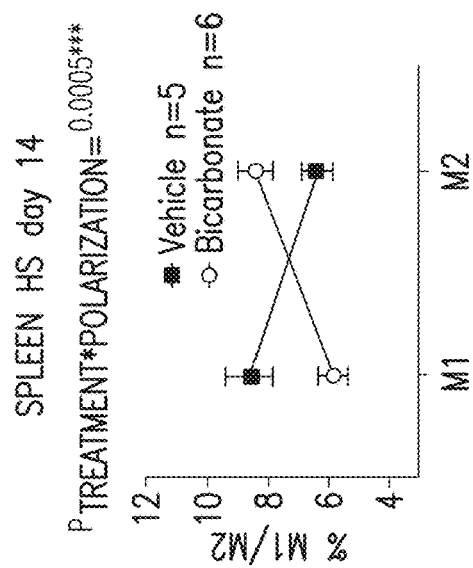
FIG. 2F is a graph showing the relative expression of M1 and M2 macrophages expressed as a percentage of total spleen cells in vehicle and bicarbonate treated rats.
Figure 2E:
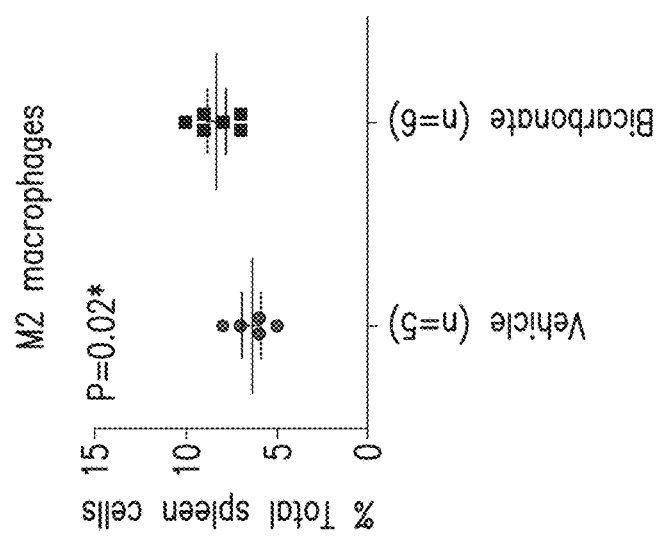
FIG. 2E is a graph showing the percentage of total spleen cells identified as M2 macrophages in vehicle and bicarbonate treated rats.
Figure 2D:
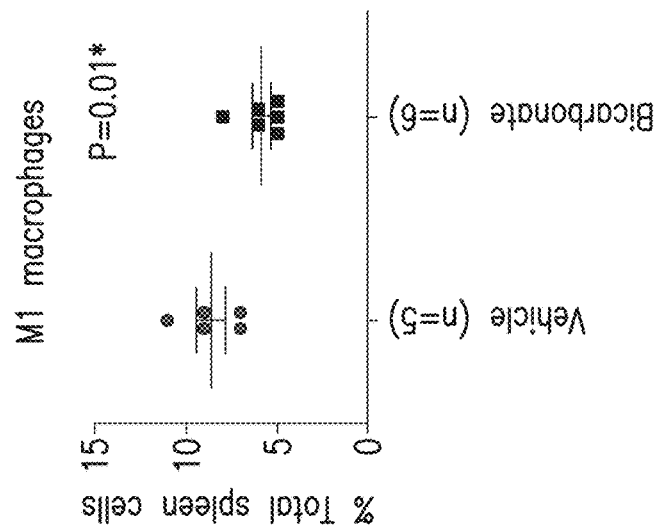
FIG. 2D is a graph showing the percentage of total spleen cells identified as M1 macrophages in vehicle and bicarbonate treated rats.
Figure 2G:
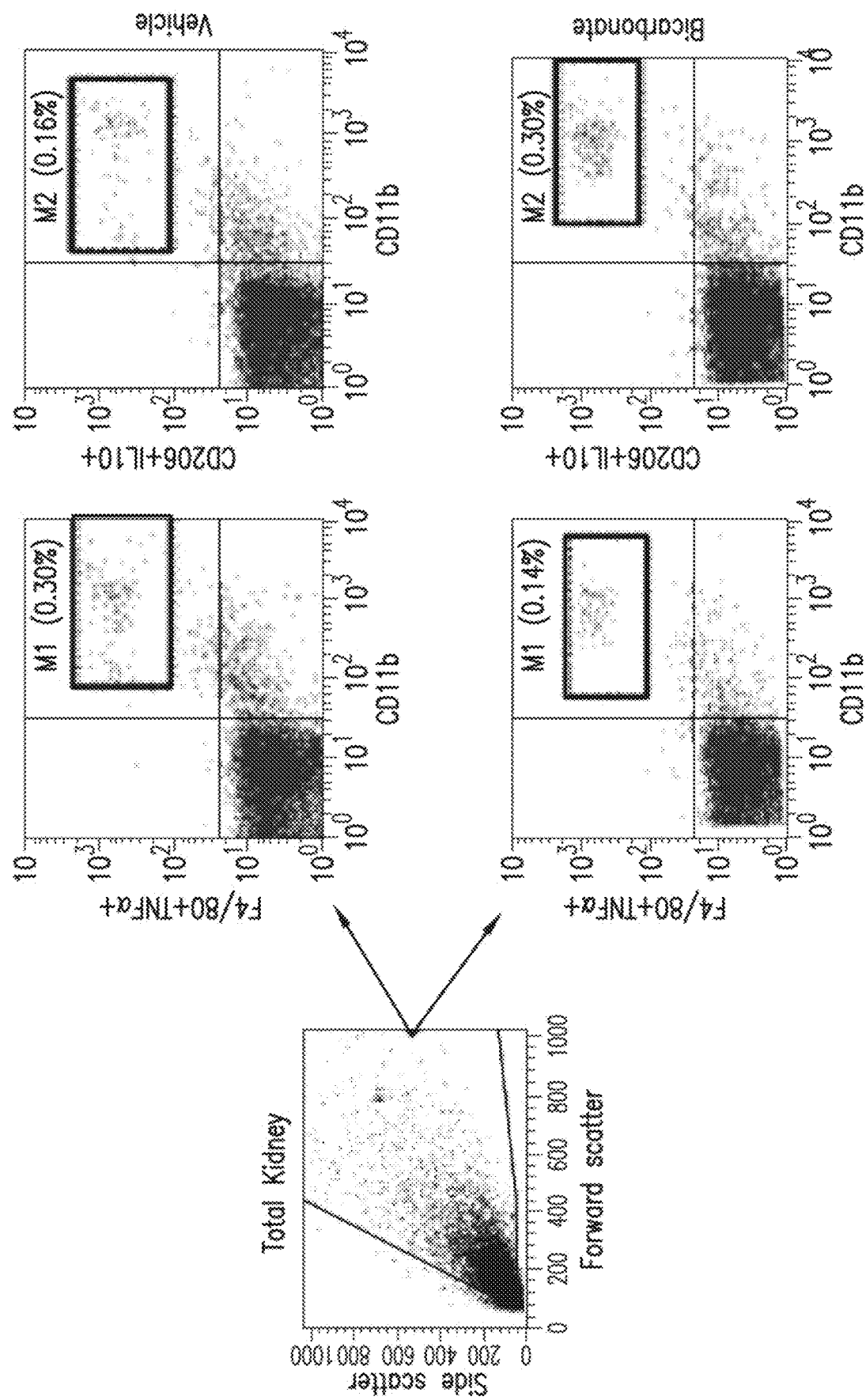
FIG. 2G shows representative gating images from kidneys of high salt (HS) treated rats.

In addition, FIGS. 2A-2G show data from flow cytometric analysis of macrophage polarization (M1/M2) from kidneys and spleen from male Dahl SS rats drinking 0.1M NaHCO$_3$ (bicarbonate) or equimolar NaCl (vehicle). All data are from rats placed on treated water (vehicle or bicarbonate) for 3 days before being switched to a HS diet for 14 days prior to tissue harvest. FIG. 2A shows the percentage of total kidney cells identified as M1 macrophages (F4/80$^+$/TNFα$^+$cells) in vehicle (n=10; filled circles) and bicarbonate (n=11; filled squares) treated rats. FIG. 2B shows the percentage of total kidney cells identified as M2 macrophages (CD206$^+$/IL10$^+$ cells) in vehicle (n=10; filled circles) and bicarbonate (n=11; filled squares) treated rats. FIG. 2C shows the relative expression of M1 and M2 macrophages expressed as a % of total kidney cells in vehicle (filled squares) and bicarbonate (open circles) treated rats. FIG. 2D shows the percentage of total spleen cells identified as M1 macrophages (F4/80$^+$/TNFα$^+$ cells) in vehicle (n=10; filled circles) and bicarbonate (n=11; 706 filled squares) treated rats. FIG. 2E shows the percentage of total spleen cells identified as M2 macrophages (CD206$^+$/IL10$^+$ cells) in vehicle (n=10; filled circles) and bicarbonate (n=11; filled squares) treated rats. FIG. 2F shows the relative expression of M1 and M2 macrophages expressed as % of total spleen cells in vehicle (filled squares) and bicarbonate (open circles) treated rats. FIG. 2G shows representative gating images from kidneys of HS treated rats.

As can be seen from Table 2 and FIGS. 2A-2G, NaHCO$_3$ treatment resulted in a significant (p<0.01) decrease in TNFα expressing macrophages (M1-polarized macrophages) and an increase in IL-10 expressing macrophages (M2-polarized macrophages) in the kidney. A significant (p=0.005) polarization from predominately M1 to M2 macrophage polarization was also observed in splenic tissue of high salt fed Dahl SS rats treated with NaHCO$_3$. Thus, oral NaHCO$_3$ promotes polarization of macrophages from a pro-inflammatory M1 to anti-inflammatory M2 state in the kidney and spleen of rats.

Figure 3A:
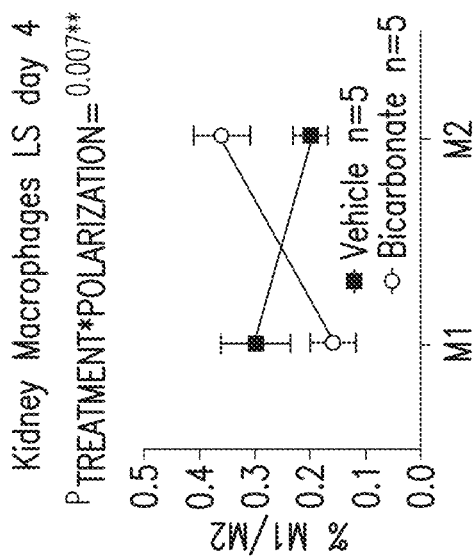
FIG. 3A is a graph showing the percentage of total kidney cells identified as M1 macrophages in vehicle and bicarbonate treated rats.
Figure 3B:
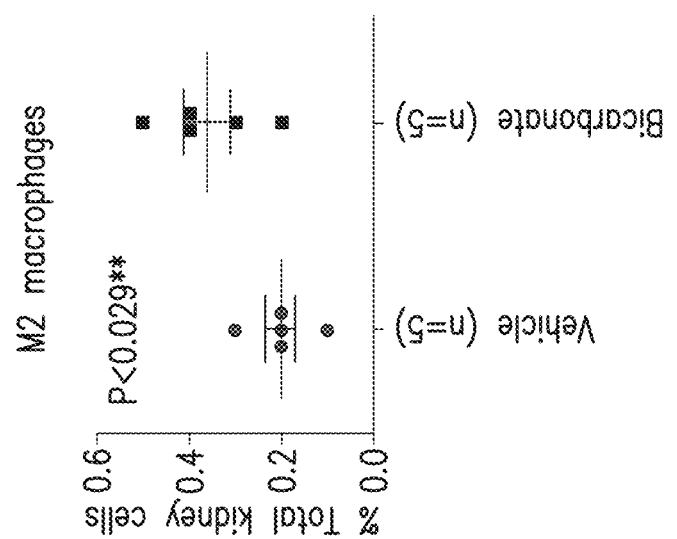
FIG. 3B is a graph showing the percentage of total kidney cells identified as M2 macrophages in vehicle and bicarbonate treated rats.
Figure 3C:
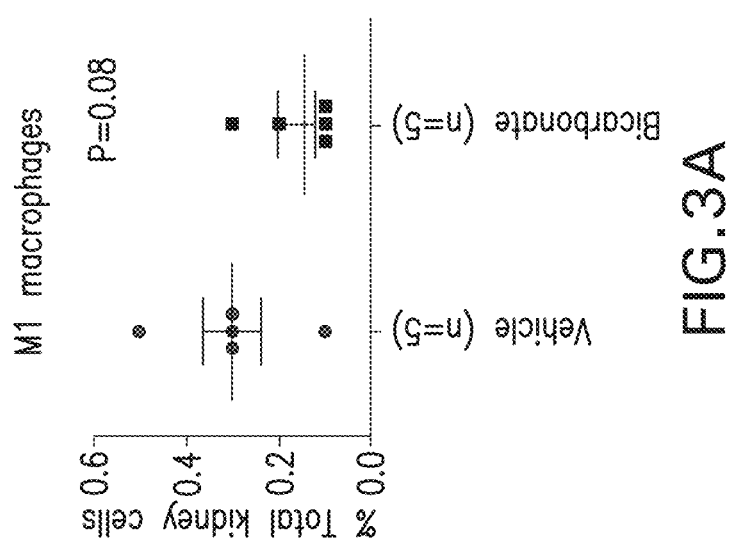
FIG. 3C is a graph showing the relative expression of M1 and M2 macrophages expressed as a percentage of total kidney cells in vehicle and bicarbonate treated rats.

As the Dahl SS rat model develops hypertension and renal injury when fed a high salt diet (Jin, C. et al. *Hypertension* 64:541-550 (2014)), in order to determine whether NaHCO$_3$ promotes macrophage M2 polarization independent of these changes, tissues from low salt fed Dahl rats and normotensive Sprague Dawley rats were examined. FIGS. 3A-3C show the data from flow cytometric analysis of macrophage polarization (M1/M2) from kidneys and spleen from male Dahl SS rats drinking either 0.1M NaHCO$_3$ (bicarbonate) or equimolar NaCl (vehicle). All data were from rats placed on treated water (vehicle or bicarbonate) for 3 days before tissue harvest. FIG. 3A shows the percentage of total kidney cells identified as M1 macrophages (F4/80$^+$/TNFα$^+$ cells) in vehicle (n=5; filled circles) and bicarbonate (n=5; filled squares) treated rats. FIG. 3B shows the percentage of total kidney cells identified as M2 macrophages (CD206$^+$/IL10$^+$ cells) in vehicle (n=5; filled circles) and bicarbonate (n=5; filled squares) treated rats. FIG. 3C shows the relative expression of M1 and M2 macrophages expressed as % total kidney cells in vehicle (filled squares) and bicarbonate (open circles) treated rats.

Figures 3D, 3E, 3F:
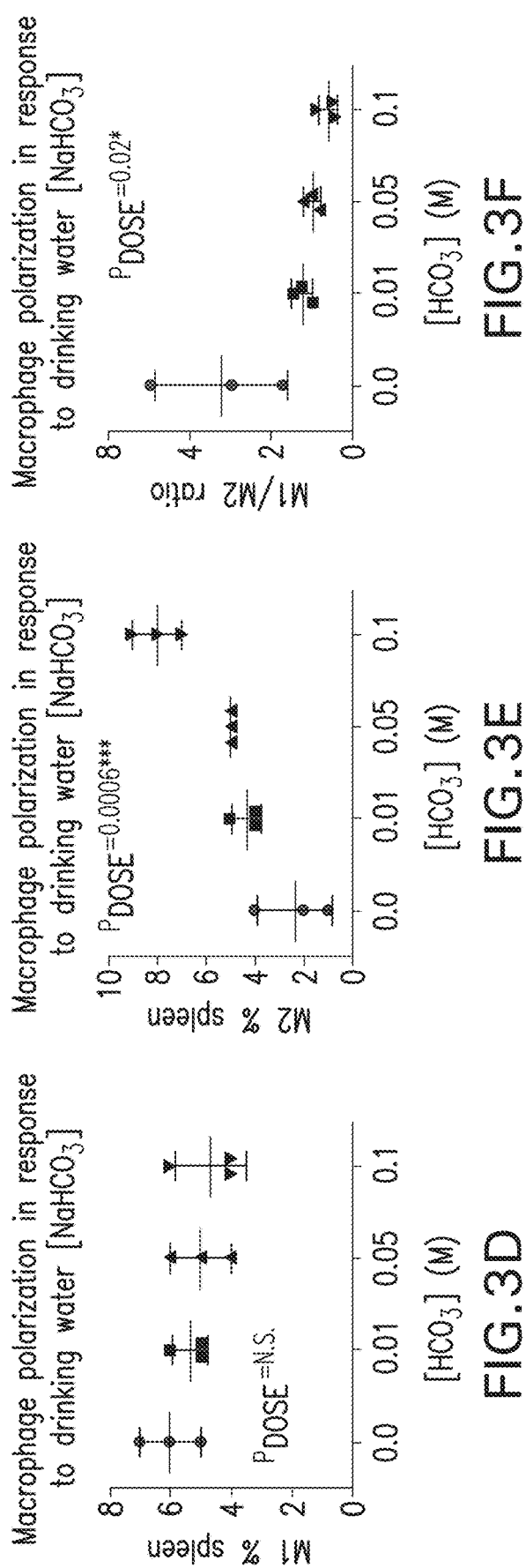
FIG. 3D is a graph showing the percentage of total kidney cells identified as M1 macrophages in response to increasing concentrations of NaHCO$_3$ in drinking water.
FIG. 3E is a graph showing the percentage of total kidney cells identified as M2 macrophages in response to increasing concentrations of NaHCO$_3$ in drinking water.
FIG. 3F is a graph showing the ratio of M1 to M2 macrophages expressed as the percentage of total kidney cells in response to increasing concentrations of NaHCO$_3$ in drinking water.

FIGS. 3D-3F show data from flow cytometric analysis of macrophage polarization (M1/M2) in kidneys of male Sprague Dawley rats (Charles River Laboratories) drinking either 0.1M NaHCO$_3$ (n=3), 0.05M NaHCO$_3$/0.05M NaCl (n=3), 0.01M NaHCO$_3$/0.09M NaCl (n=3) or 0.1M NaCl (n=3) for 4 days prior to tissue harvest. Specifically, FIG. 3D shows the percentage of total kidney cells identified as M1 macrophages (F4/80$^+$/TNFα$^+$ cells) in response to increasing concentrations of NaHCO$_3$ in drinking water (0M on right to 0.1M on left) (all doses were made equimolar with addition of NaCl to the drinking water). FIG. 3E shows the percentage of total kidney cells identified as M2 macrophages (CD206$^+$/IL10$^+$ cells) in response to increasing concentrations of NaHCO$_3$ in drinking water (0M on right to 0.1M on left). FIG. 3F shows the ratio of M1 to M2 macrophages expressed as % of total kidney cells in response to increasing concentrations of NaHCO$_3$ in drinking water.

As shown in FIGS. 3A-3F, in low salt fed Dahl SS rats, a significant (p=0.007) polarization from predominately M1 to M2 macrophage polarization was still observed in kidney tissue. In addition, the effect of NaHCO$_3$ intake to promote M2 polarization in the kidney was also observed in out-bred Sprague Dawley rats. Furthermore, the effect of NaHCO$_3$ was found to be dose dependent, with changes in polarization identified with as little as 0.01M NaHCO$_3$ in the drinking water for only 4 days in rats eating low salt laboratory chow. Interestingly, in C57BL/6 mice, 3 days of oral NaHCO$_3$ (0.1M in drinking water) increased splenic macrophages and had no effect on M2 macrophages (unpublished data).

Figure 4D:
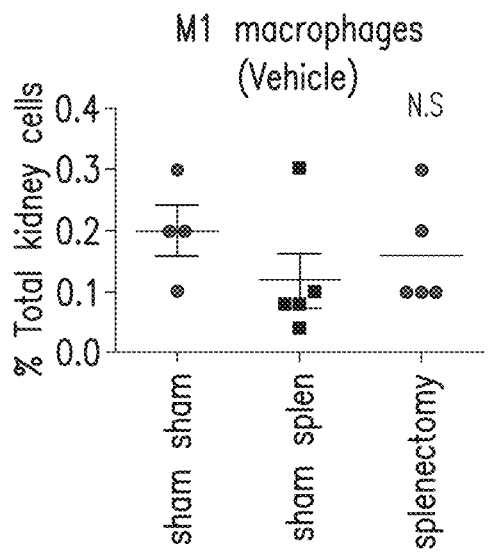
FIG. 4D is a graph showing the percentage of total renal cells identified as M1 macrophages in vehicle treated rats in which the spleen was removed (splenectomy), moved but not removed (sham spleen), and left untouched (Sham Sham) approximately 28 days prior to tissue harvest.

Moreover, FIGS. 4A-4G show data from flow cytometric analysis of macrophage polarization (M1/M2) from kidneys of male Dahl SS rats drinking either 0.1M NaHCO$_3$ (bicarbonate) or equimolar NaCl (vehicle) following removal of the spleen (splenectomy)/sham splenectomy and laparotomy only (spleen not moved during surgery). All data are from rats placed on treated water (vehicle or bicarbonate) for 3 days before being switched to a HS diet for an additional 14 days prior to tissue harvest. More specifically, FIG. 4A shows the percentage of total kidney cells identified as M1 macrophages (F4/80$^+$/TNFα$^+$ cells) and M2 macrophages (CD206$^-$/IL10$^+$ cells) in vehicle (n=4; filled circles) and bicarbonate (n=6; filled squares) treated rats in which the spleen was removed. FIG. 4B shows the percentage of total kidney cells identified as M1 macrophages (F4/80$^+$/TNFα$^+$ cells) and M2 macrophages (CD206$^+$/IL10$^+$ cells) in vehicle (n=5; filled circles) and bicarbonate (n=5; filled squares) treated rats in which the spleen was moved to midline during surgery but not removed (sham splenectomy). FIG. 4C shows the percentage of total kidney cells identified as M1 macrophages (F4/80$^+$/TNFα$^+$ cells) and M2 macrophages (CD206$^+$/IL10$^+$ cells) in vehicle (n=5; filled circles) and bicarbonate (n=5; filled squares) treated rats in which the spleen was untouched during surgery (Sham Sham). FIG.

Figure 4E:
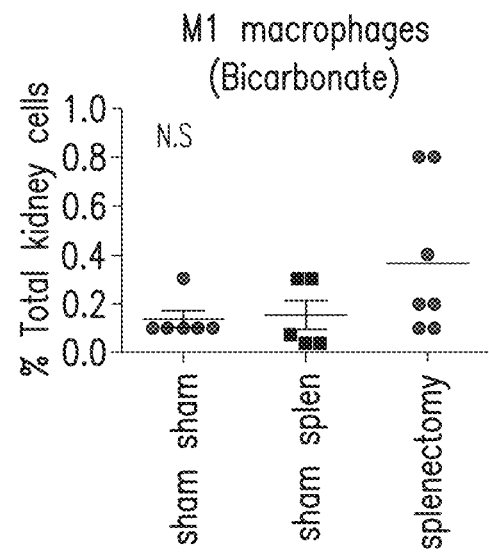
FIG. 4E is a graph showing the percentage of total renal cells identified as M1 macrophages in bicarbonate treated rats in which the spleen was removed (splenectomy), moved but not removed (sham spleen), and left untouched (Sham Sham) approximately 28 days prior to tissue harvest.
Figure 4F:
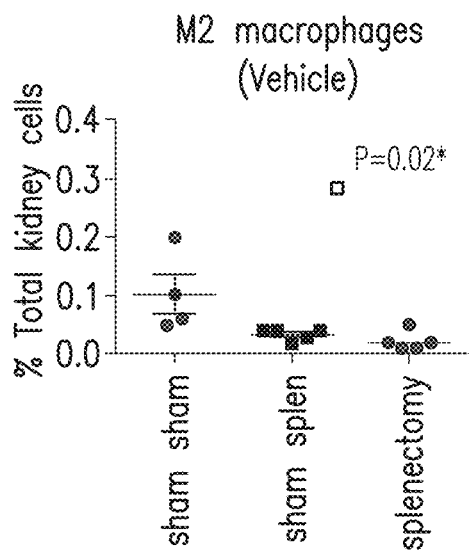
FIG. 4F is a graph showing the percentage of total renal cells identified as M2 macrophages in vehicle treated rats in which the spleen was removed (splenectomy), moved but not removed (sham spleen), and left untouched (Sham Sham) approximately 28 days prior to tissue harvest.
Figure 4G:
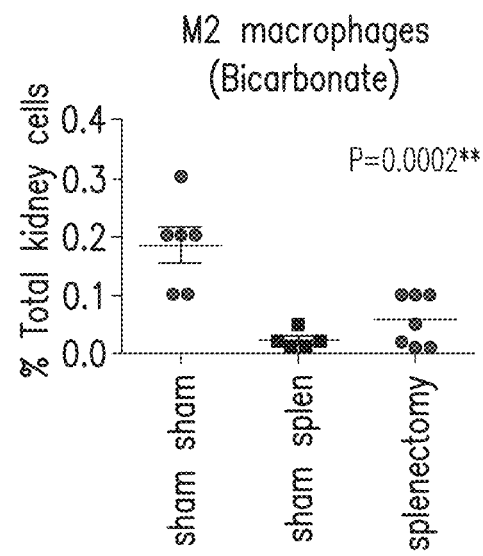
FIG. 4G is a graph showing the percentage of total renal cells identified as M2 macrophages in bicarbonate rats in which the spleen was removed (splenectomy), moved but not removed (sham spleen), and left untouched (Sham Sham) approximately 28 days prior to tissue harvest.

4D shows the percentage of total renal cells identified as M1 macrophages (F4/80−/TNFα+ cells) in vehicle treated rats in which the spleen was removed (splenectomy), moved but not removed (sham spleen) and left untouched (Sham Sham) approximately 28 days prior to tissue harvest. FIG. 4E shows the percentage of total renal cells identified as M1 macrophages (F4/80+/TNFα+ cells) in bicarbonate treated rats in which the spleen was removed (splenectomy), moved but not removed (sham spleen) and left untouched (Sham Sham) approximately 28 days prior to tissue harvest. FIG. 4F shows the percentage of total renal cells identified as M2 macrophages (CD206+/IL10+ cells) in vehicle treated rats in which the spleen was removed (splenectomy), moved but not removed (sham spleen) and left untouched (Sham Sham) approximately 28 days prior to tissue harvest. FIG. 4G shows the percentage of total renal cells identified as M2 macrophages (CD206+/IL10+ cells) in bicarbonate rats in which the spleen was removed (splenectomy), moved but not removed (sham spleen) and left untouched (Sham Sham) approximately 28 days prior to tissue harvest.

As shown in FIGS. 4A-4G, it was found that complete removal of the spleen or simple manipulation of the spleen to midline during surgical laparotomy prior to beginning NaHCO$_3$ or vehicle treatment, completely abolished the effect of NaHCO$_3$ to promote M1 to M2 polarization in the kidney of Dahl SS rats fed a HS diet for 2 weeks. Furthermore, both of these maneuvers resulted in a significant decrease in kidney M2 macrophages when compared to sham laparotomy only (P=0.02 & 0.0002 comparing laparotomy only to sham splenectomy and splenectomy for vehicle and bicarbonate treated groups, respectively).

Figure 5G:
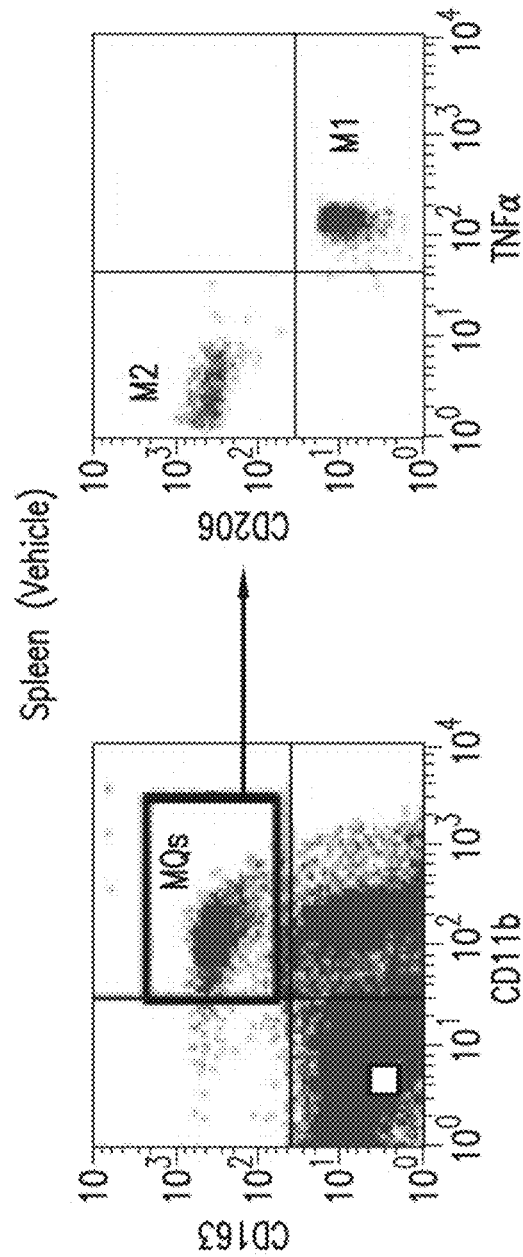
FIGS. 5G-5H show representative gating images from spleens of HS treated rats using the alternative macrophage markers.
Figure 5H:
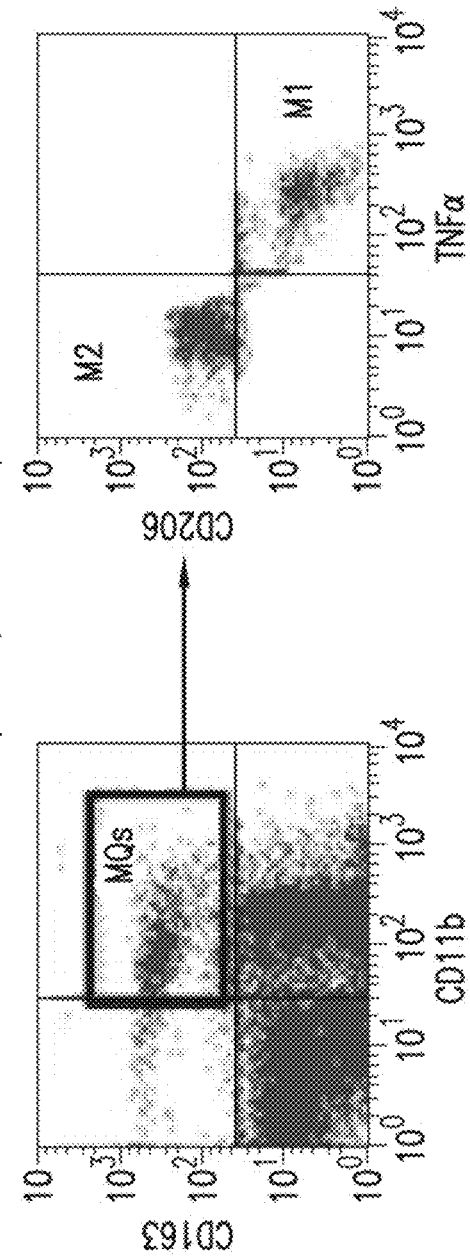
Figure 5I:
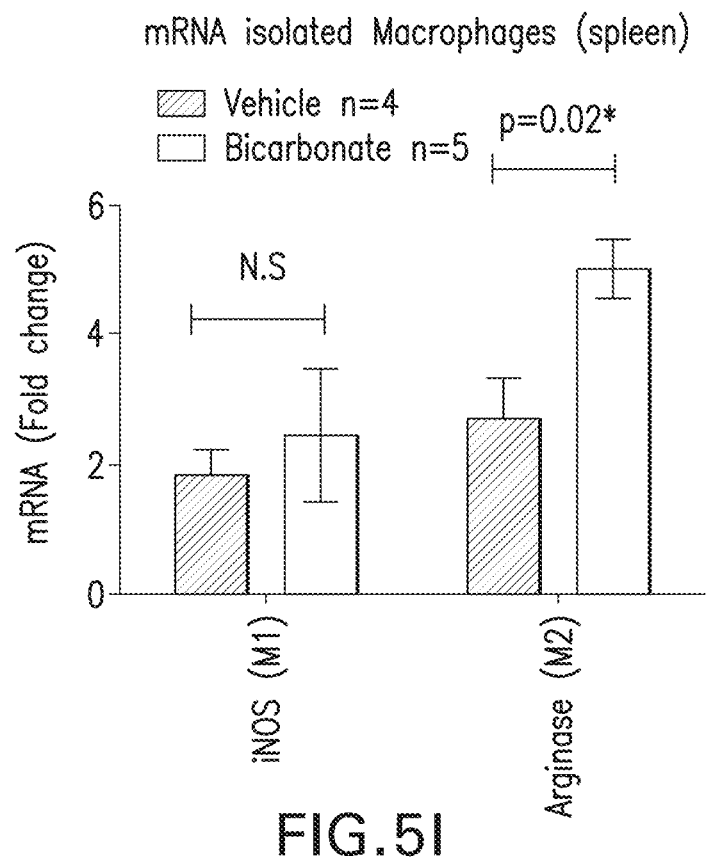
FIG. 5I is a bar graph showing iNOS and arginase mRNA expression in macrophages isolated from the spleen of vehicle and bicarbonate treated rats.

Markers for M1 (CD11b/F4/80/TNFα) and M2 (CD11b/CD206/IL-10) macrophages were selected based on previous studies in the rat; however, to confirm the specificity of these markers, the markers were compared with alternative markers: CD68/CD163/CD206/TNFα for M1 and CD68/CD163/CD206/IL-10 for M2. FIGS. 5A-5I demonstrate the validation of macrophage polarization in response to bicarbonate treatment in spleen and kidney. In particular, the figures show data from flow cytometric analysis of macrophage polarization (M1/M2) of male Dahl SS rats drinking either 0.1M NaHCO$_3$ (bicarbonate; n=4-5) or equimolar NaCl (vehicle; n=3-5) in kidney and spleen. All data are from rats that were placed on a HS diet (8%) for 14 days prior to tissue harvest. FIG. 5A shows the relative expression of M1 and M2 macrophages expressed as percentage of total spleen cells in vehicle (n=4; closed squares) and bicarbonate (n=5; open circles) treated rats fed HS for 14 days prior to tissue harvest. M1 macrophages were defined as CD11b-c+/F4-80+/TNFα+ cells and M2 macrophages were defined as CD11b-c+/CD206+/IL-10+. FIG. 5B shows relative expression of M1 and M2 macrophages expressed as percentage of total spleen cells from vehicle (n=4; closed squares) and bicarbonate (n=5; open circles) treated rats fed HS for 14 days prior to tissue harvest. Alternative M1 makers were CD68+/CD163+/CD206−/TNFα and alternative M2 markers were CD68+/CD163+/CD206+/IL-10+. FIG. 5C shows relative expression of M1 and M2 macrophages expressed as percentage of total kidney cells from vehicle (n=4; closed squares) and bicarbonate (n=5; open circles) treated rats fed HS for 14 days prior to tissue harvest. M1 macrophages were defined as CD11b-c+/F4-80+/TNFα+ cells and M2 macrophages were defined as CD11b-c+/CD206+/IL-10+. FIG. 5D shows relative expression of M1 and M2 macrophages expressed as percentage of total kidney cells from vehicle (n=4; closed squares) and bicarbonate (n=5; open circles) treated rats fed HS for 14 days prior to tissue harvest. Alternative M1 makers were CD68+/CD163+/CD206−/TNFα and alternative M2 markers were CD68+/CD163+/CD206+/IL-10+. FIG. 5E shows relative expression of M1 and M2 macrophages expressed as percentage of total kidney cells from vehicle (n=4; closed squares) and bicarbonate (n=5; open circles) treated rats in which the spleen was removed prior to 14 days HS treatment. M1 macrophages were defined as CD11b-c+/F4-80+/TNFα+ cells and M2 macrophages were defined as CD11b-c+/CD206+/IL-10+. FIG. 5F shows relative expression of M1 and M2 macrophages expressed as percentage of total kidney cells from vehicle (n=4; closed squares) and bicarbonate (n=5; open circles) treated rats in which the spleen was removed prior to 14 days HS treatment. Alternative M1 makers were CD68/CD163/CD206/TNFα and alternative M2 markers were CD68/CD163/CD206/IL-10. FIG. 5G-5H shows representative gating images from spleens of HS treated rats using the alternative macrophage markers (CD68/CD163/CD206/TNFα: for M1 and CD68/CD163/CD206/IL-10: for M2). FIG. 5I shows mRNA expression in macrophages isolated from the spleen of vehicle (n=4; closed columns) and bicarbonate (n=5; open columns) treated rats. iNOS mRNA expression was measured to confirm M1 polarization and Arginase mRNA expression was measured to confirm M2 polarization.

Figure 6:
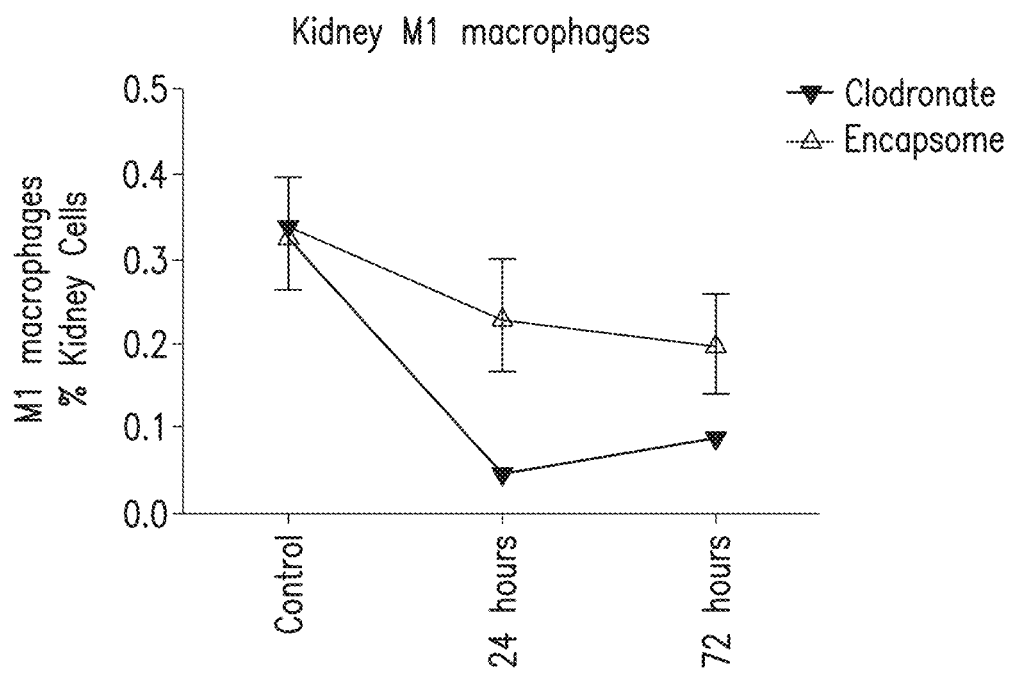
FIG. 6 is a graph showing the percentage of total kidney cells identified as M1 macrophages cells 24 and 72 hours following a single injection of clodronate liposomes or control liposomes (Encapsome).
Figure 7H:
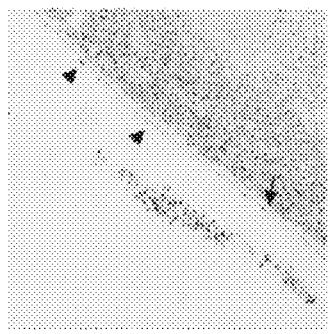
FIG. 7A-7I shows various images of the effect of splenic movement/vagal denervation on the splenic mesothelium.
Figure 7I:
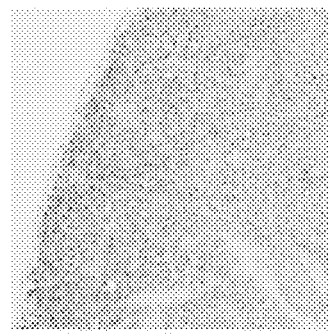
Figure 7F:
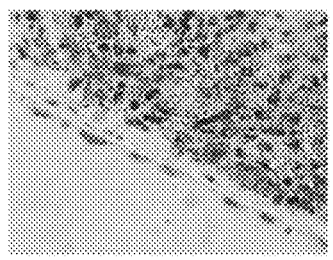
Figure 7G:
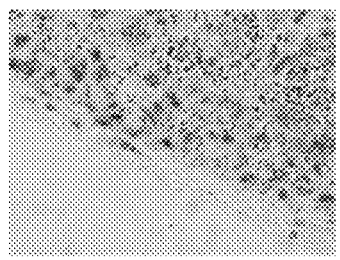
Figure 7D:
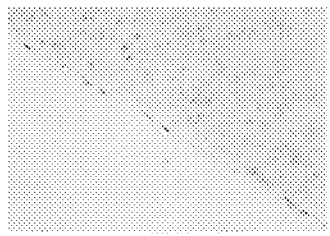
Figure 7E:
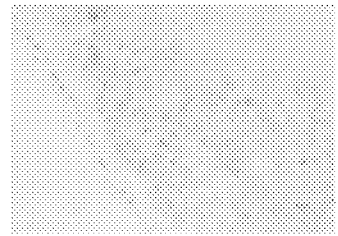
Figure 7A:
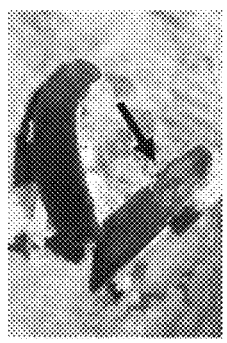
Figure 7B:
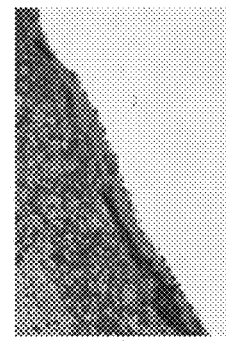
Figure 7C:
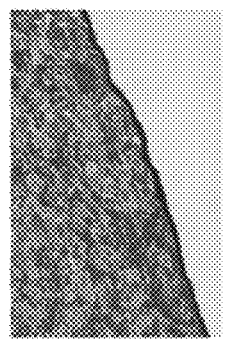
Figure 8A:
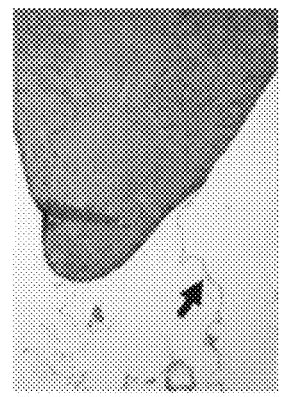
FIG. 8A-8I shows various images demonstrating evidence of neuronal connections to the splenic mesothelium.
Figure 8B:
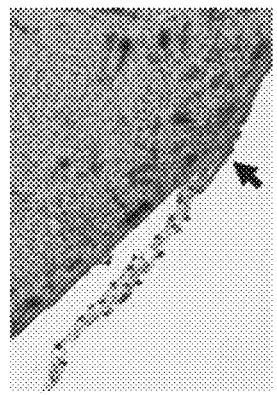
Figure 8C:
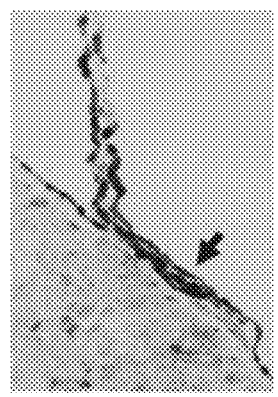
Figure 8D:
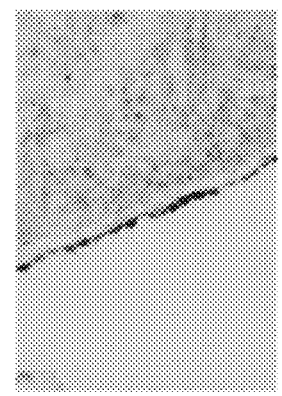
Figure 8E:
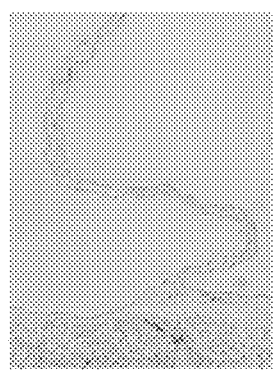
Figure 8F:
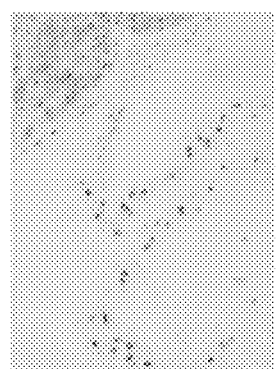
Figure 8G:
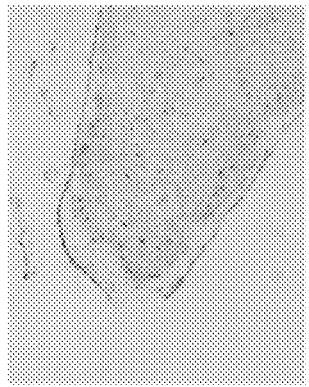
Figure 8H:
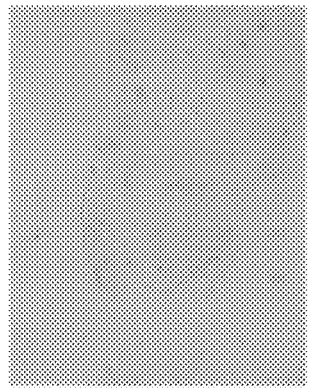
Figure 8I:
Figure 9C:
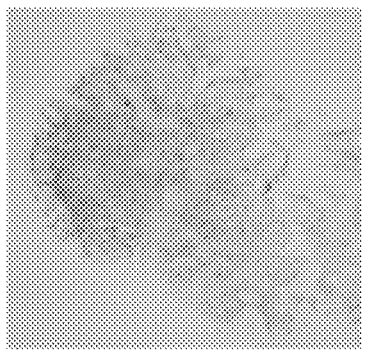
FIG. 9A-9I shows various images of a dense network of acetylcholine esterase positive nerves immediately below the splenic capsule.
Figure 9F:
Figure 9I:
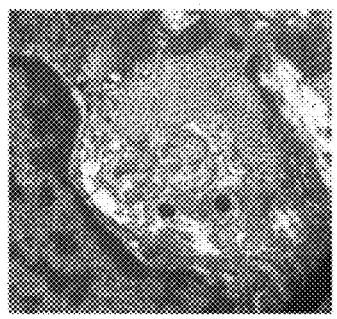
Figure 9B:
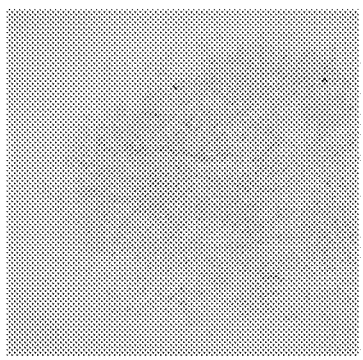
Figure 9E:
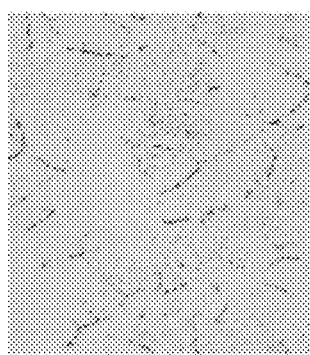
Figure 9H:
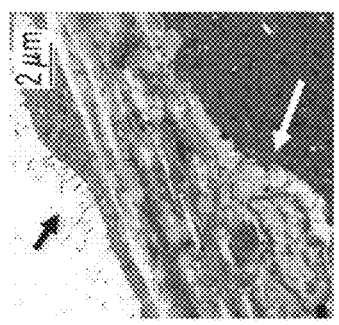
Figure 9A:
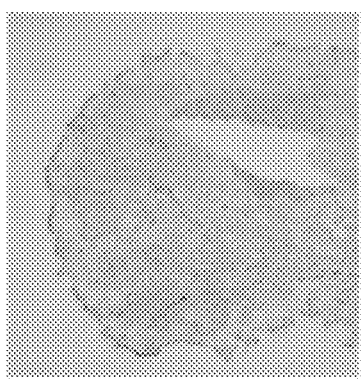
Figure 9D:
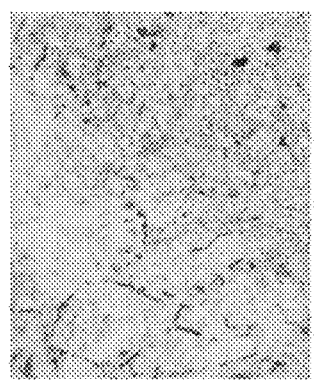
Figure 9G:
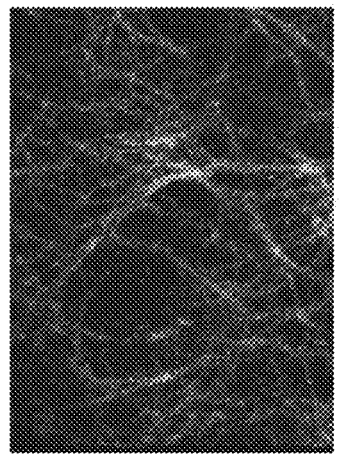

The results using both markers sets (as shown in FIGS. 5A-5I) were highly consistent and confirmed observations of M1 to M2 polarization in the spleen and kidney of NaHCO$_3$ treated rats as well as the effect of splenectomy to abolish this response. In addition, FIG. 6 shows the percentage of total kidney cells identified as M1 macrophages cells 24 and 72 hours following a single injection of clodronate liposomes (20 mg/kg/i.v) or control liposomes (Encapsome). As demonstrated by FIG. 6, the identity of renal cells identified as macrophages by specific depletion with clodronate liposomes was confirmed.

As it was found that light manipulation to visualize the spleen at midline during surgical laparotomy (sham splenectomy) was sufficient to abolish the anti-inflammatory response to oral NaHCO$_3$, the pathways through which vagal efferent signals stimulated by oral NaHCO$_3$ may be transmitted to the splenic parenchyma were investigated. FIG. 7 shows the effect of splenic movement/vagal denervation on the splenic mesothelium. Panel A of FIG. 7 shows a spleen harvested from a surgical control rat (top; laparotomy only) and rat in which the spleen was moved to midline during surgery. Surgery was performed on both rats 28 days prior to tissue harvest. Fibrosis of parts of the splenic capsule (represented by the arrow) can be observed in spleens harvested from rats in which the spleen was manipulated to midline during surgery. Panel B of FIG. 7 shows a trichrome stained image of the splenic capsule (original magnification 20×) demonstrating thickening on the capsule (blue staining) and mesothelial cell hypertrophy and hyperplasia (pink on capsule) typical of a spleen that has been manipulated to midline during surgical laparotomy. Panel C of FIG. 7 shows a normal capsule histology (original magnification 20×) in a surgical sham rat in which the spleen was not moved (trichrome staining). Panel D of FIG. 7 shows acetylcholinesterase staining of capsular mesothelial cells in a surgical sham rat. As shown in panel D, there is a flattened appearance of the mesothelial cells and strong positive staining for acetylcholinesterase (original image magnification 20×). Panel E of FIG. 7 shows acetylcholinesterase staining of capsular mesothelial cells in a rat in which the spleen had been moved to midline during surgery. There is a thickened capsular layer and hypertrophied appearance of the mesothelial cells. Positive staining for acetylcholinesterase is present but markedly less than that observed in control tissue (original image magnification 20×). Panel F of FIG. 7 shows acetylcholinesterase staining of capsular mesothelial cells in a surgical sham rat in which the esophagus was visualized but the vagal nerves left untouched without moving the spleen. There is a flattened appearance of the mesothelial cells and strong positive staining for acetylcholinesterase (original image magnification 40×). Panel G of FIG. 7 shows acetylcholinesterase staining of capsular mesothelial cells in a rat in which the vagal nerves were transected below the diaphragm without moving the spleen 14 days prior to tissue harvest. There is an absence of positive staining for acetylcholinesterase specifically in the surface mesothelial layer (original image magnification 40×). Panel H of FIG. 7 shows a low power image of spleen described in panel F. Mesothelial cells staining positive for acetylcholinesterase can be observed as a necklace like appearance along the splenic capsule (indicated by arrows) (original magnification 10×). Panel I of FIG. 7 shows a low power image of spleen described in panel G. There is a lack of positive stained mesothelial cells on the splenic capsule. Acetylcholine esterase staining remains similar to control tissue in all other regions of the splenic parenchyma. Cells within and immediately below the capsule continue to stain positive for acetylcholinesterase (original magnification 10×).

Based on the data in FIG. 7, while, outside of the splenic hilum, only light connective tissue was observed to be attached to the spleen in rodents, it was found that gentle splenic manipulation during surgery resulted in marked fibrosis of the splenic capsule and hypertrophy/hyperplasia of the capsular mesothelial cell layer following 2+ weeks of recovery.

In addition, FIG. 8 shows evidence of neuronal connections to the splenic mesothelium. In Panel A of FIG. 8, thin connections to the splenic capsule can be observed in trichrome stained rat spleens at low power (original magnification 5×) that are not observed by the naked eye (arrow). The origin of these connections is uncertain but they appear to be common at the splenic poles and along the inferior edge of the spleen surface. Panel B of FIG. 8 shows a connection at higher magnification (original magnification 40×). Trichrome stained tissue connects on the capsular surface often forming a "raised nodule" which protrudes from the capsule more than the surrounding mesothelial layer. In Panel C of FIG. 8, these connections stain strongly positive for the pan neuronal marker PGP9.5. There is shown a connection from a control rat stained for PGP9.5. There is also positive staining on the surrounding mesothelial layer. This was present only on the inferior axis of the spleen and was most evident in areas where connections such as this were observed (original magnification 40×). Panel D of FIG. 8 shows PGP9.5 staining of capsular mesothelial cells in a surgical sham rat. There is a flattened appearance of the mesothelial cells and strong positive staining for PGP9.5 (original image magnification 40×). Panel E of FIG. 8 shows that these connections stain negative positive for the sympathetic neuronal marker tyrosine hydroxylase. Strong positive staining was observed around blood vessels in the splenic parenchyma (one can be observed directly below the intersection point of this connection) (original image magnification 20×). Panel F of FIG. 8 shows acetylcholinesterase staining within a connection to the splenic capsule in a control rat. There is punctate positive staining for acetylcholinesterase throughout the connection. Positive staining for acetylcholinesterase can also be observed in the surrounding capsular mesothelial cells and underlying splenic parenchyma (original image magnification 40×). Panel G of FIG. 8 shows PGP9.5 staining at the inferior edge of the spleen. Mesothelial cells in this region stain strongly positive for the pan neuronal marker PGP9.5 (original image magnification 5×). Panel H of FIG. 8 shows tyrosine hydroxylase staining at the inferior edge of the spleen. Mesothelial cells in this region stain negative for the sympathetic neuronal marker tyrosine hydroxylase (ariginal image magnification 5×). Panel I of FIG. 8 shows acetylcholinesterase staining at the inferior edge of the spleen. Mesothelial cells in this region stain strongly positive for the para-sympathetic neuronal marker acetylcholine esterase (original image magnification 5×).

As shown in FIG. 8, in histological sections, numerous fragile connections from the surrounding fascia were found to directly connect to the mesothelial layer along the inferior edge of the spleen. Prior to manipulation, both these connections as well as proximal capsular mesothelial cells stained strongly positive for the pan-neuronal marker PGP9.5 as well as acetylcholine esterase, indicating parasympathetic neural function.

Following manipulation of the spleen to midline (presumed denervation by breaking these fragile connections), the splenic capsule fibrosed (this was macroscopically identified in all animals in which spleens were moved to midline during surgery) and a marked hypertrophy/hyperplasia of the mesothelial cells and reduction in acetylcholinesterase staining was observed when compared to sham controls in which a laparotomy was performed but the spleen had not been manipulated. Two weeks following transection of the vagal nerves below the diaphragm, splenic weight was lower in vagotomized animals (0.92±0.05 g) than in surgical control animals (1.29±0.04 g; p<0.0001), with spleens accounting for 0.28±0.01% and 0.35±0.01% (P<0.01) of total body weight in vagal denervated and control animals, respectively. While PGP9.5 staining did not appear to be altered with vagotomy, acetylcholinesterase staining within mesothelial cell bodies on the splenic capsule was abolished with prior vagotomy with 5 of 5 surgical control animals being found positive for mesothelial acetylcholine esterase and 4 out of 4 animals in which complete sub-diaphragmatic vagotomy was confirmed, being found negative for mesothelial acetylcholinesterase staining by an observer unaware of the origin of the sections.

To further investigate how mesothelial cells may signal the splenic parenchyma, the relationship between surface mesothelial cells and the splenic parenchyma immediately below the collagen layer of the splenic capsule was examined. FIG. 9 shows the dense network of acetylcholinesterase positive nerves immediately below the splenic capsule. Panels A and D of FIG. 9 show thin (5 mm) sections through the frontal plane of the splenic capsule indicating strong and diffuse positive staining for the pan neuronal marker PGP9.5 in the capsular layer (panel A, original magnification 5×; panel d, original magnification 20×). Panels B and E of FIG. 9 show thin (5 mm) sections through the frontal plane of the splenic capsule indicating strong positive staining for the sympathetic neuronal marker tyrosine hydroxylase in the capsular layer with tyrosine hydroxylase positive tissue forming a loose web of interconnected nerves (panel b, original magnification 5×; panel e, original magnification 20×). Panels C and F of FIG. 9 show thin (5 mm) sections through the frontal plane of the splenic capsule indicating strong and diffuse positive staining for the parasympathetic neuronal marker acetylcholinesterase in the capsular layer (panel c, original magnification 5×; panel f, original magnification 20×). Panel H of FIG. 9 shows the splenic capsule viewed at 40× on a confocal microscope. Tissue was loaded with the $Ca^{2+}$ sensitive indicator fluo-4. There is a dense layer of nerve tissue that can be observed directly below the mesothelial cell layer across the entire splenic capsule. The density of this neural web is much greater than that observed in panels B and E in tissue stained positive for tyrosine hydroxylase, indicating additional nerve tissue is present. Activation of these nerves can be stimulated by electrical field stimulation. In Panel I of FIG. 9, transmission electron microscopy indicates that nerves sit directly below the splenic capsule. Black arrow indicates capsular mesothelial cell. White arrow indicates nerve closely associated with the splenic capsule. In Panel J of FIG. 9, nerves are identified by the presence of intracellular vesicles typical of synaptic junctions.

Figure 20:
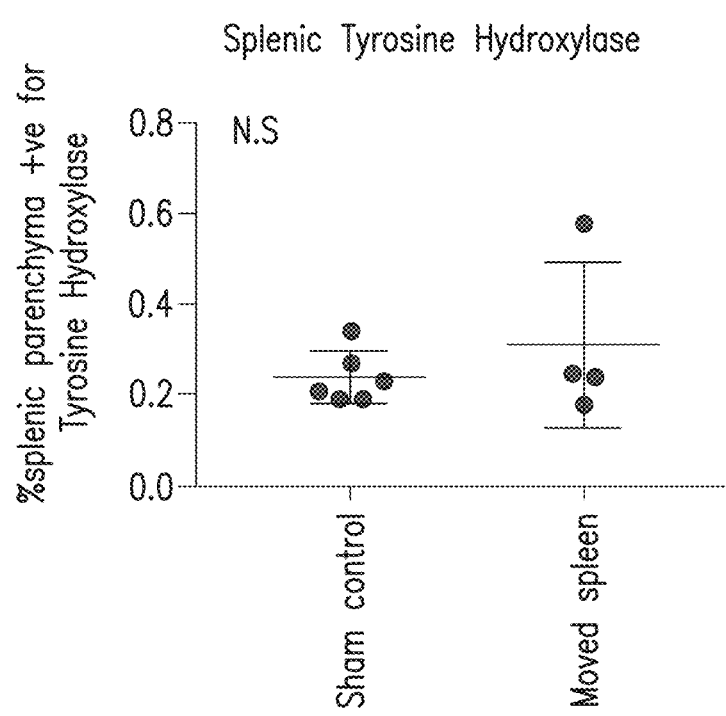
FIG. 20 is a graph showing splenic tyrosine hydroxylase.
Figure 21A:
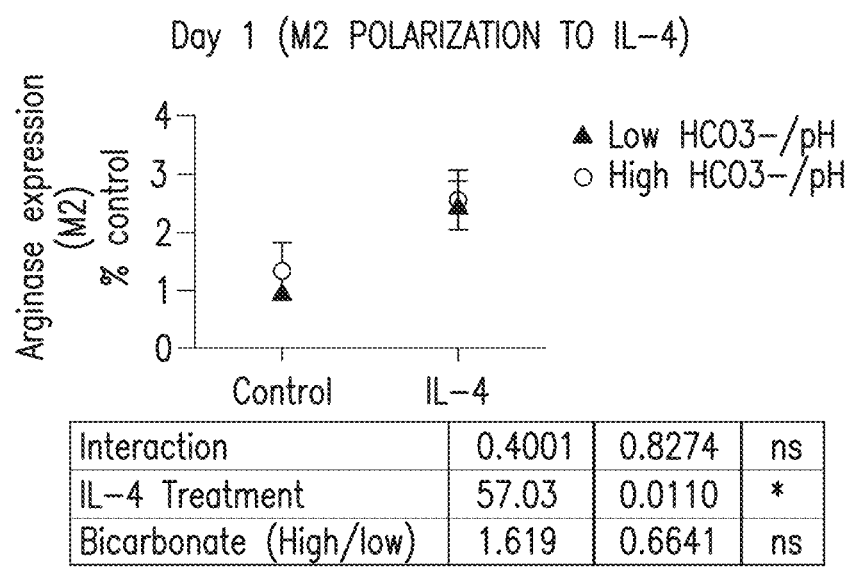
FIG. 21A-21D shows M2 polarization to IL-4 at days 1 (FIG. 21A) and 3 (FIG. 21B) and M1 polarization to INFγ at days 1 (FIG. 21C) and 3 (FIG. 21D).
Figure 21B:
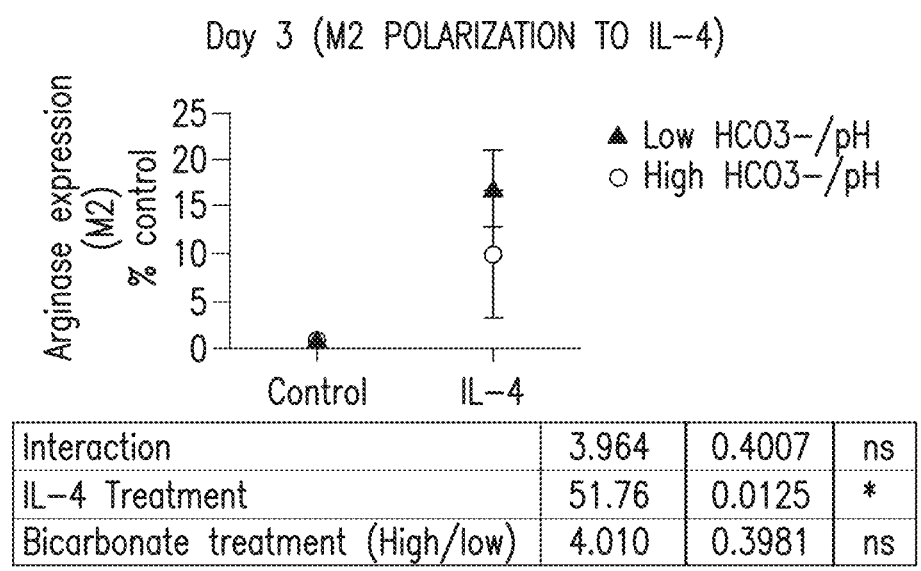
Figure 21C:
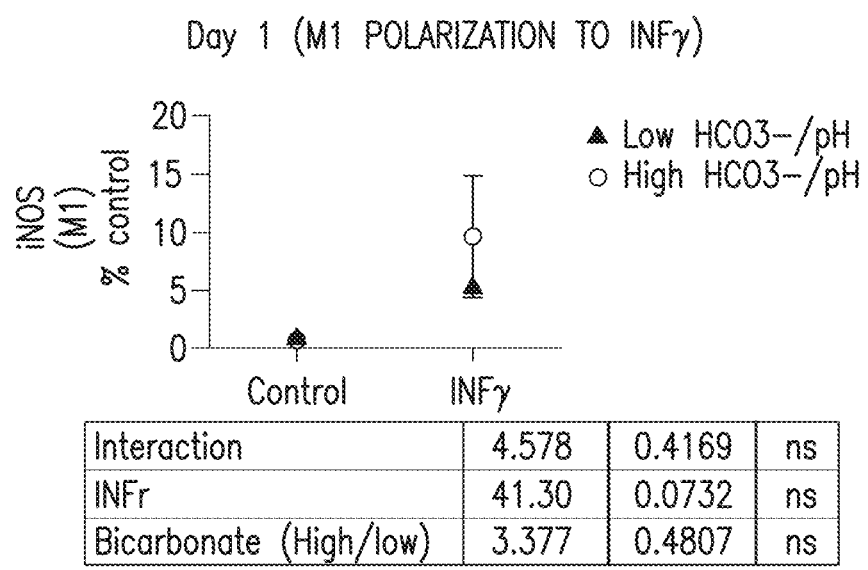
Figure 21D:
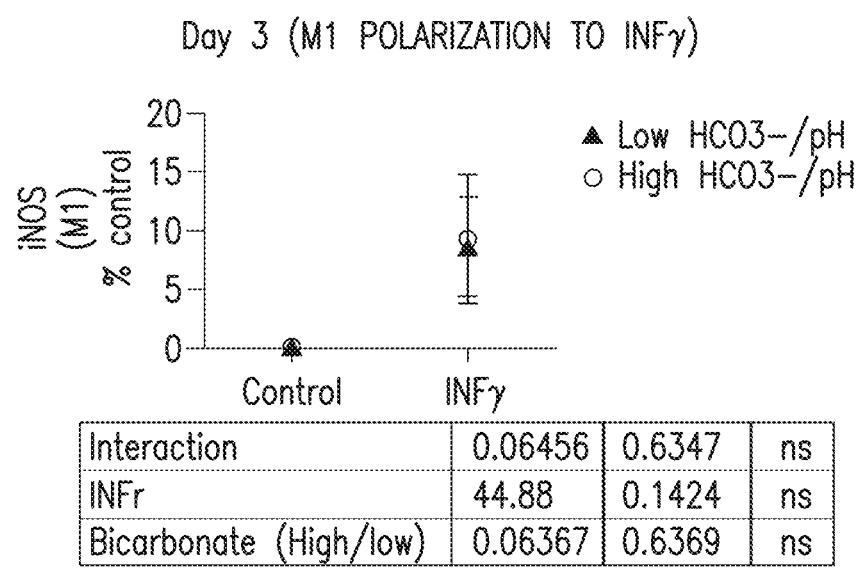
Figure 23A:
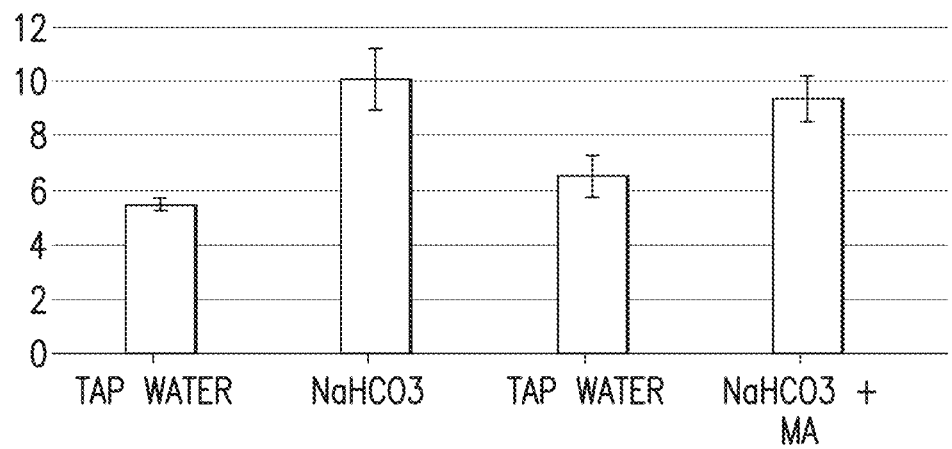
FIGS. 23A-23B are bar graphs showing the percentage of anti-inflammatory (T Regs, FIG. 23A) and pro-inflammatory (Th17, FIG. 23B) cells in total white blood cells in mice treated with tap water, NaHCO$_3$, or NaHCO$_3$+ metabolic acid.
Figure 23B:
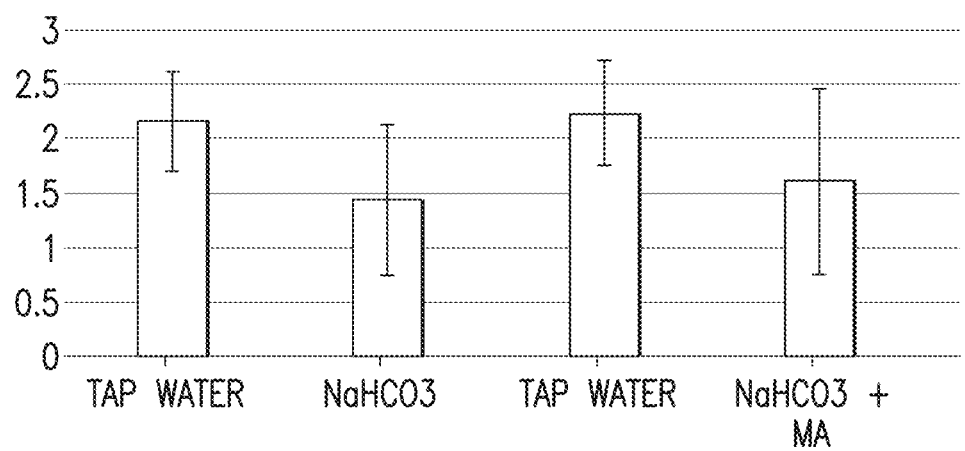
Figure 24:
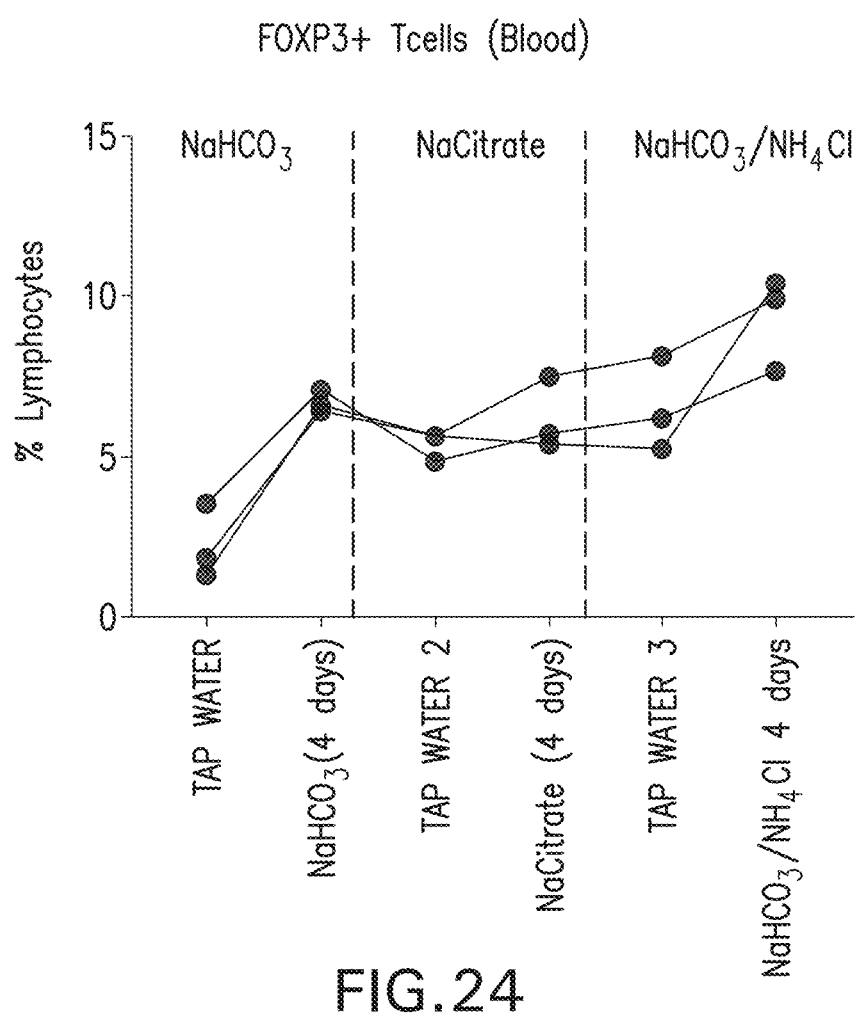
FIG. 24 is a line graph showing percentage of circulating anti-inflammatory T cells (FOXP3+ T-regs) over time in rats treated with NaHCO$_3$.

Based on the data in FIG. 9, when loaded with the $Ca^{2+}$ sensitive dye Fluo-4, a dense plexus of nerves immediately below the collagen layer of the splenic capsule was observed (in which activation could be stimulated by electrical field stimulation). Immunohistochemical analysis of transverse sections through the splenic capsule revealed that the majority of these nerves stained only lightly positive for PGP9.5 and acetylcholine esterase but were negative for tyrosine hydroxylase. Moreover, as shown in FIG. 20, there was no evidence that manipulation of the spleen altered sympathetic innervation of the spleen, as indicated by tyrosine hydroxylase staining.

Human Studies

To determine whether oral $NaHCO_3$ had a similar anti-inflammatory action in humans as found in rats, blood samples were evaluated at baseline and 1, 2 and 3 hours following ingestion of a single dose (2 g) of $NaHCO_3$ (n=11) or equimolar NaCl (n=6), each dissolved in 250 mL of bottled water. Pre- and post-treatment values of serum electrolytes are presented in Table 3 below.

TABLE 3

CHANGES IN SERUM ELECTROLYTES, GLUCOSE, AND CARBON DIOXIDE FOLLOWING AN ACUTE DOSE OF $NAHCO_3$

|  | Pre-treatment | | Post-treatment | |
| --- | --- | --- | --- | --- |
|  | CON | TXT | CON | TXT |
| Na (mmol/L) | 140.4 ± 0.9 | 141.1 ± 0.8 | 141.2 ± 0.4 | 140.8 ± 0.5 |
| K (mmol/L)† | 4.1 ± 0.1 | 4.3 ± 0.1 | 4.3 ± 0.1* | 3.9 ± 0.1* |
| Cl⁻ (mmol/L) | 100.2 ± 0.9 | 100.9 ± 0.9 | 102.4 ± 0.4 | 102.3 ± 0.8 |

CON, control group (NaCl ingestion); TXT, treatment group ($NaHCO_3$ ingestion), Na, sodium; K, potassium; Cl⁻, chloride.
*significant change versus baseline ($p < 0.05$);
†significant group × time interaction ($p = 0.029$).

As shown in Table 3, there was a significant group by time interaction for changes in serum potassium. Specifically, serum potassium decreased with $NaHCO_3$ treatment, but there was no change with NaCl treatment.

Table 4 below shows the baseline flow cytometry values of all subjects before ingesting $NaHCO_3$ or NaCl in solution. Data represents values obtained on the first day of the protocol following overnight fasting and prior to subjects ingesting either $NaHCO_3$ or NaCl solutions. Body mass index and c-reactive protein (CRP) levels were not significantly different at baseline between either group, indicating a similar baseline inflammatory state. Prior to any treatment, the percent of blood leukocytes that were $TNF\alpha^+$ neutrophils, M1 macrophages, or M2 macrophages were all significantly higher in the $NaHCO_3$ treatment group when compared to baseline values obtained in the NaCl treatment group.

TABLE 4

BASELINE DATA FOR SUBJECTS IN $NAHCO_3$ AND NACL TREATMENT GROUPS

| Variable | Baseline data (week 0) Control subjects (NaCl) n = 6 | Treatment subjects ($NaHCO_3$) n = 12 | P (students t-test) |
| --- | --- | --- | --- |
| Age (years) | 24.8 ± 1.2 | 27.4 ± 2.0 | N.S |
| Height (cm) | 177.0 ± 3.1 | 167.7 ± 3.2 | N.S |
| Weight (kg) | 81.0 ± 7.8 | 71.9 ± 5.3 | N.S |
| BMI (kg/m²) | 25.7 ± 2.1 | 25.3 ± 1.2 | N.S |
| Systolic blood pressure (mmHg) | 118.7 ± 4.7 | 118.6 ± 3.4 | N.S |
| Diastolic blood pressure (mmHg) | 71.8 ± 3.2 | 68.3 ± 2.7 | N.S |
| CRP | 1.06 ± 0.30 | 1.22 ± 0.58 | N.S |
| Hct (%) | 45 ± 1 | 43 ± 2 | N.S |
| Glucose (mg/dL) | 92 ± 4 | 90 ± 2 | N.S |
| BUN (mg/dL) | 12.5 ± 1.0 | 13.3 ± 1.2 | N.S |
| Creatinine (mg/dL) | 0.84 ± 0.06 | 8.85 ± 0.07 | N.S |
| Na (mM) | 141 ± 1 | 140 ± 1 | N.S |
| K (mM) | 4.0 ± 0.1 | 4.3 ± 0.1 | N.S |
| Cl (mM) | 100 ± 1 | 101 ± 1 | N.S |
| $CO_2$ (mM) | 21 ± 0 | 21 ± 1 | N.S |
| Protein (g/dL) | 6.9 ± 0.1 | 6.9 ± 0.1 | N.S |
| Albumin (g/dL) | 4.5 ± 0.1 | 4.4 ± 0.1 | N.S |
| $TNF\alpha^+$ neutrophils (% blood leukocytes) | 55 ± 2.2 | 26 ± 7.3 | 0.0003** |
| M1 macrophages (% blood leukocytes) | 3.3 ± 0.3 | 1.6 ± 0.5 | 0.007** |
| M2 macrophages (% blood leukocytes) | 1.9 ± 0.2 | 1.4 ± 0.2 | N.S |

Figure 10A:
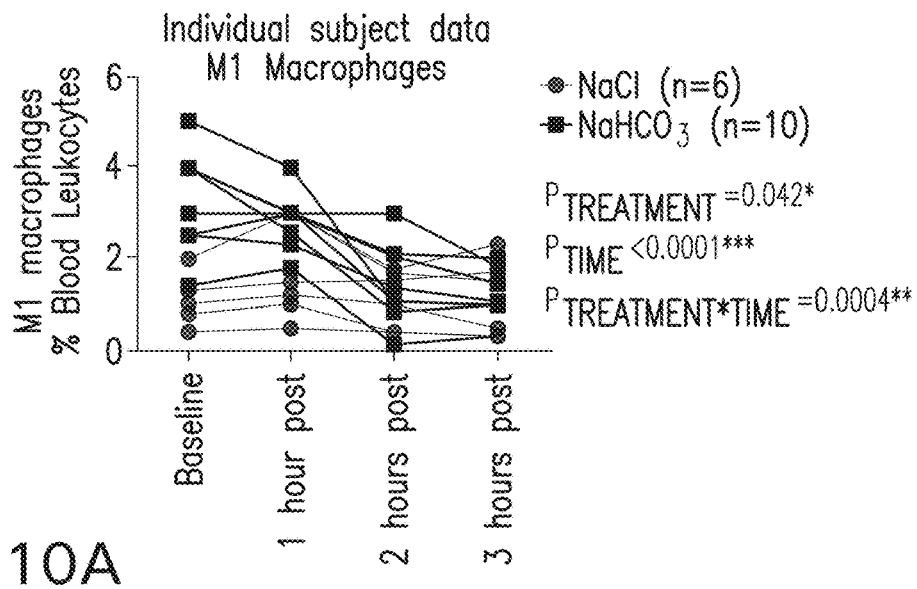
FIG. 10A is a line graph showing the percentage of total blood leukocytes identified as M1 macrophages in vehicle and bicarbonate treated subjects.
Figure 10B:
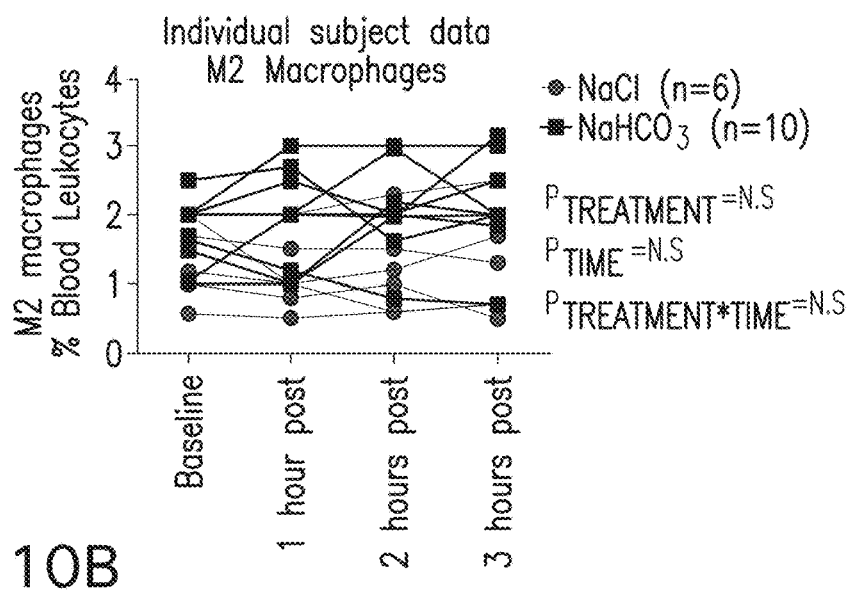
FIG. 10B is a line graph showing the percentage of total blood leukocytes identified as M2 macrophages in vehicle and bicarbonate treated subjects.
Figure 10C:
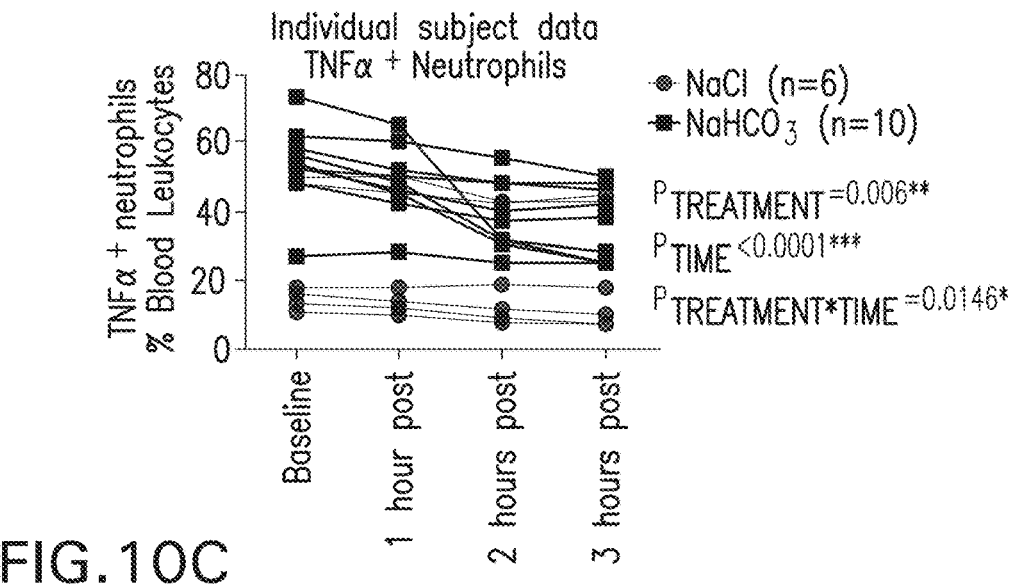
FIG. 10C is a line graph showing the percentage of total blood leukocytes identified as TNFα+ neutrophils in vehicle and bicarbonate treated subjects.

FIGS. 10A-10F show data from flow cytometric analysis of human blood from subjects drinking either $NaHCO_3$ (bicarbonate) or equimolar NaCl (vehicle). FIGS. 10A-10C show individual data for each participant. P-values represent the results of 2-way repeated measures ANOVA. Two subjects were excluded from this analysis as they did not have blood drawn at 3 hours but are included in FIGS. 10D-10F. $P<0.05$ was considered significant. FIG. 10A shows the percentage of total blood leukocytes identified as M1 macrophages ($CD11b^+/CD68^-/TNF\alpha^+$ cells) in vehicle (n=6; red filled squares) and bicarbonate (n=10; black filled circles) treated subjects. FIG. 10B shows the percentage of total blood leukocytes identified as M2 macrophages ($CD11b^+$, $CD68^+$, $CD206^+$ and $IL-10^+$ cells) in vehicle (n=6; red filled squares) and bicarbonate (n=10; black filled circles) treated subjects. FIG. 10C shows the percentage of total blood leukocytes identified as TNFα+ neutrophils (CD16+/TNFα+ cells) in vehicle (n=6; red filled squares) and bicarbonate (n=10; black filled circles) treated subjects.

Figure 10D:
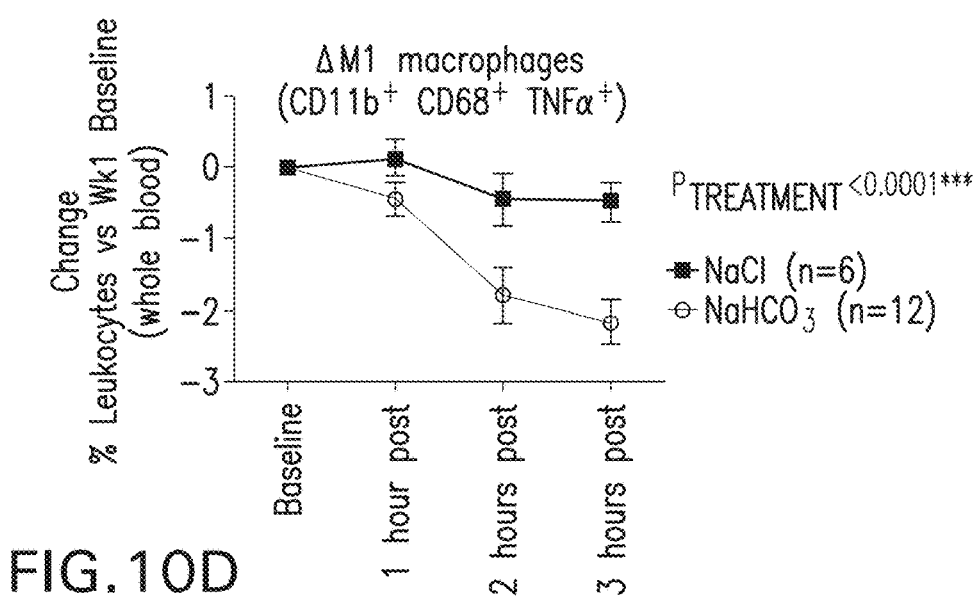
FIG. 10D is a line graph showing the change in percentage of total blood leukocytes identified as M1 macrophages in vehicle and bicarbonate treated subjects as compared to baseline.
Figure 10E:
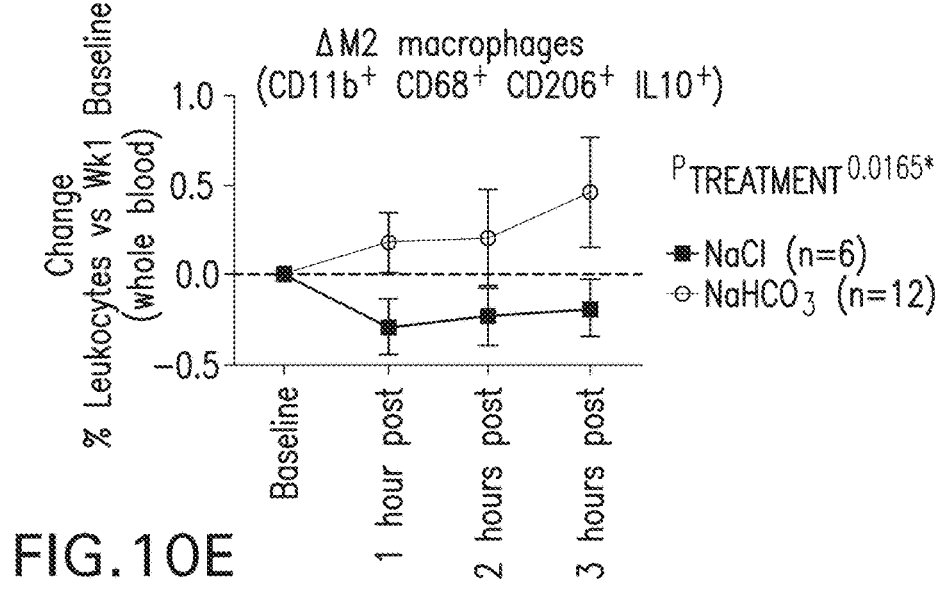
FIG. 10E is a line graph showing the change in the percentage of total blood leukocytes identified as M2 macrophages in vehicle and bicarbonate treated subjects as compared to baseline.
Figure 10F:
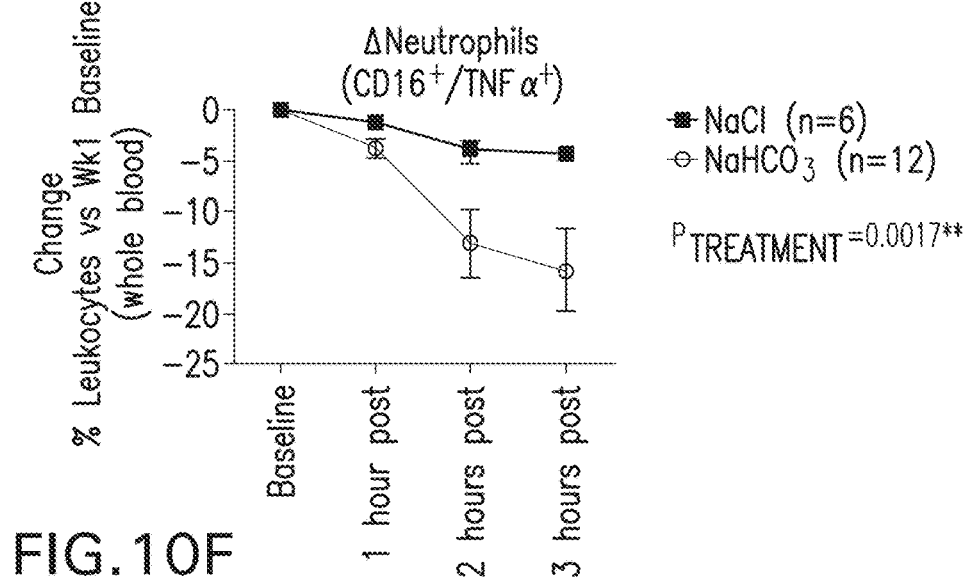
FIG. 10F is a line graph showing the change in the percentage of total blood leukocytes identified as TNFα+ neutrophils in vehicle and bicarbonate treated subjects as compared to baseline.

In FIGS. 10D-10F, on the x-axis, the 1 hour post represents data obtained 1 hour after ingesting 2 g of $NaHCO_3$ (n=12 subjects) or equimolar NaCl (n=6 subjects) solution in 250 mL of bottled water, the 2 hours post represents data obtained 2 hours after ingesting 2 g of $NaHCO_3$ or equimolar NaCl solution in 250 mL of bottled water, and the 3 hours post represents data obtained 3 hours after ingesting 2 g of $NaHCO_3$ or equimolar NaCl solution in 250 mL of bottled water (note not all subjects had blood drawn at 3 hours (n=10 for $NaHCO_3$ at 3 hours)). All data are mean±SE. PTREATMENT is the output of a 2-way ANOVA comparing treatment groups. $P<0.05$ was considered significant. FIG.

10D shows the change in percentage of total blood leukocytes identified as M1 macrophages (CD11b$^+$/CD68$^+$/TNFα$^+$ cells) in vehicle (n=6; filled squares) and bicarbonate (n=12; open circles) treated subjects as compared to baseline. FIG. 10E shows the change in the percentage of total blood leukocytes identified as M2 macrophages (CD11b$^+$, CD68$^+$, CD206$^+$ and IL-10$^+$ cells) in vehicle (n=6; filled squares) and bicarbonate (n=12; open circles) treated subjects as compared to baseline. FIG. 10F shows the change in the percentage of total blood leukocytes identified as TNFα+ neutrophils (CD16$^+$/TNFα$^+$ cells) in vehicle (n=6; filled squares) and bicarbonate (n=12; open circles) treated subjects as compared to baseline.

Based on the data in FIGS. 10A-10F, there was a significant TREATMENT*TIME effect on both M1 macrophages (p=0.0004) and TNFα positive neutrophils (p=0.0146) with the levels of these inflammatory cells in the plasma being reduced to a significantly greater degree following ingestion of NaHCO$_3$ when compared to NaCl. The greatest decreases in blood inflammatory cells were observed at 2 and 3 hours following NaHCO$_3$ ingestion. Similar to our observations in rats, oral NaHCO$_3$ ingestion increased the percentage of blood leukocytes identified by flow cytometry as M2 macrophages (p=0.00165) when comparing changes in percent of M2 macrophages from baseline following ingestion of NaHCO$_3$ when compared to NaCl. Decreases in inflammatory TNFα+ neutrophils and M1 macrophages in the NaHCO$_3$ treatment group did not appear to be related to the differing baseline levels observed between treatment groups. When comparing individual responses between subjects of different groups, subjects with similar baseline levels of blood leukocytes responded differently if they received NaHCO$_3$ compared to NaCl.

Example 2

Ingestion of NaHCO$_3$ Improves Vascular Endothelial Function

Methods and Materials

Flow-mediated dilation ("FMD") is a human assay of nitric oxide bioavailability and functional assessment of endothelial function in humans. The FMD test predicts cardiovascular disease ("CVD") and events. The vasodilator response is controlled for the shear profile.

Results

Figure 11A:
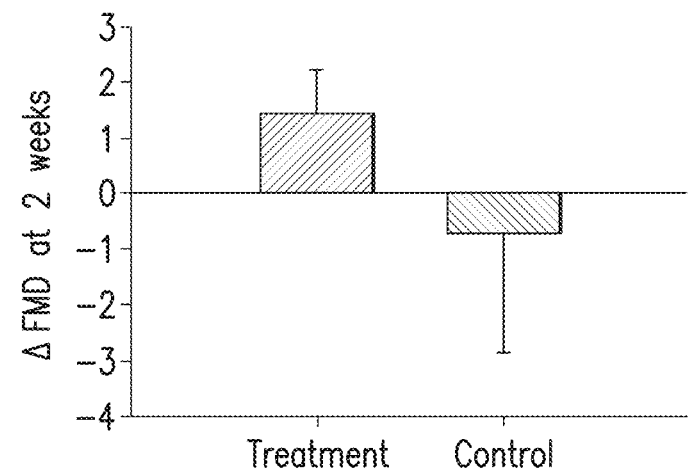
FIG. 11A is a bar graph showing the change in flow-mediated dilation ("FMD") at two weeks.
Figure 11B:
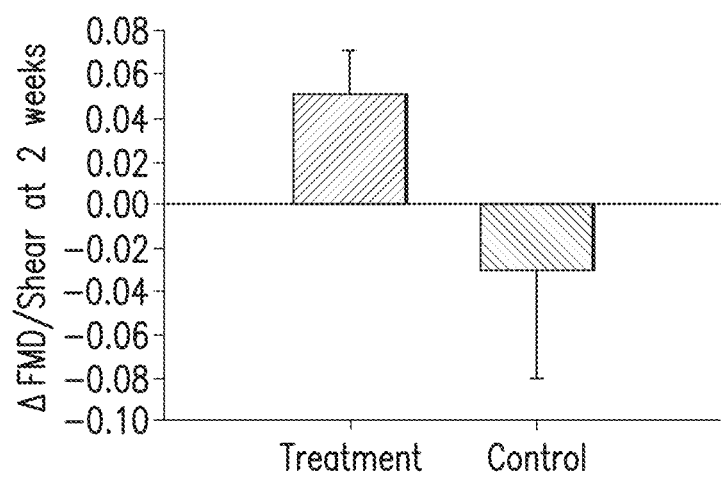
FIG. 11B is a bar graph showing the change in FMD/Shear at two weeks.

FIG. 11A shows the change in FMD at two weeks and FIG. 11B shows the change in FMD/Shear at two weeks. As shown in FIGS. 11A and 11B, two weeks of oral NaHCO$_3$ ingestion improves FMD and FMD/Shear whereas no change, or even a slight decrease, is observed with placebo. The significance is that every 1% increase in FMD has been associated with about a 9% reduction in CVD risk.

Example 3

Ingestion of NaHCO$_3$ Improves Parasympathetic Activity

Methods and Materials

Changes in heart rate (HR) and RR-interval were monitored over the last 5 min of a 15 min period of quiet rest in a supine position to establish baseline values. Time-domain indices of heart rate variability (HRV) including the root mean square differences of successive normal sinus RR intervals (rMSSD) and the percentage of successive normal sinus RR intervals >50 ms (pNN50) were calculated from a 3-lead ECG that was continuously recorded via a Finapres NOVA (Finapres Medical Systems, The Netherlands). Following treatment an additional 5 min segment of data was collected in the same manner and used to calculate post-treatment values of rMSSD and pNN50.

Results

Figure 12A:
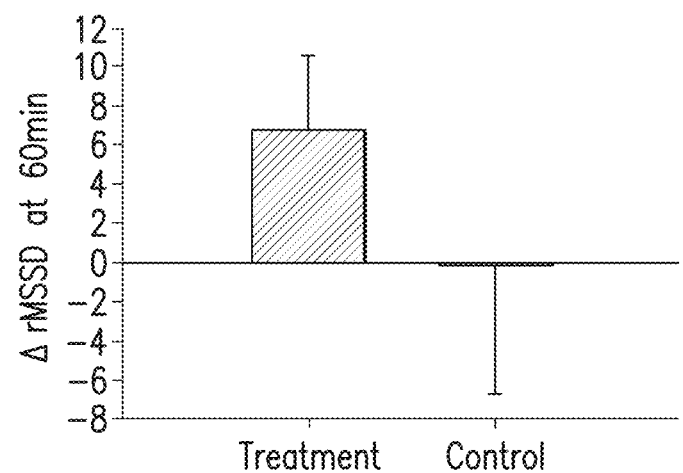
FIG. 12A is a bar graph showing the change in Root Mean Square of the Successive Differences ("rMSSD") at 60 minutes.
Figure 12B:
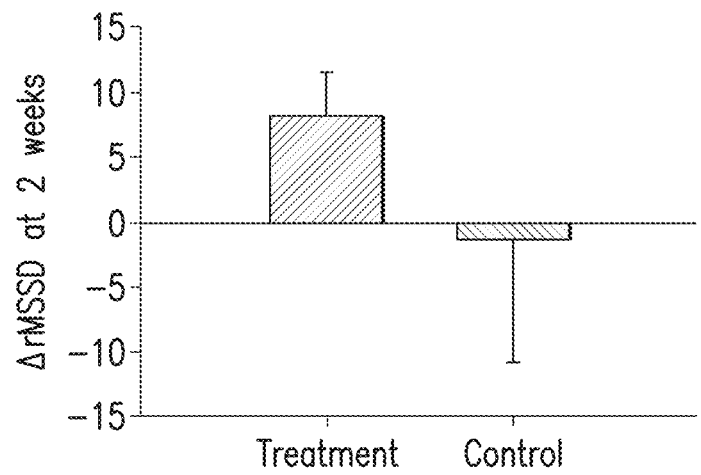
FIG. 12B is a bar graph showing the change in rMSSD at two weeks.

FIG. 12A shows the change in Root Mean Square of the Successive Differences ("rMSSD") at 60 minutes, while FIG. 12B shows the change in rMSSD at 2 weeks. Root Mean Square of the Successive Differences represents a measure of vagus-mediated heart rate variability. The greater the heart rate variability, the more vagal and thus parasympathetic activity. The data in FIGS. 12A and 12B demonstrate that both a single dose of NaHCO$_3$ as well as ingestion of NaHCO$_3$ for 2 weeks improves parasympathetic activity in humans.

Example 4

Ingestion of NaHCO$_3$ Reduces the Pro-Inflammatory Cytokines, IL-6 and TNF-α

Methods and Materials

IL-6 and TNF-α were determined in plasma samples using the microfluidic simple plex cartridge system following manufacturer specifications. Briefly, Simple Plex uses 25 μL of serum for measurement of the four cytokines. The work flow of the Simple Plex assays is: (a) a test cartridge is primed with samples with each sample split into channels (i.e., TNF-α and IL-6 to react with their respective antibodies immobilized on glass nanoreactors; (b) after sample incubation, circuits in the cartridge are cleaned with wash buffer, and biotinylated detection antibody solutions are individually pumped into their respective channels to bind to protein analyte captured on the GNRs; (c) after incubation, unbound detection antibodies are washed away and a detection solution (i.e., streptavidin DyLight 650) is flowed into all channels to conjugate with the biotinylated detection antibodies; (d) the detection solution is washed away; detection fluorophores (i.e., DyLight 650) are excited with a 631 nm laser; and the fluorescence signals are read with a charge-coupled device (CCD) camera. The signals are used for quantification based on master calibrator curves provided by the manufacturer.

Results

Figure 13A:
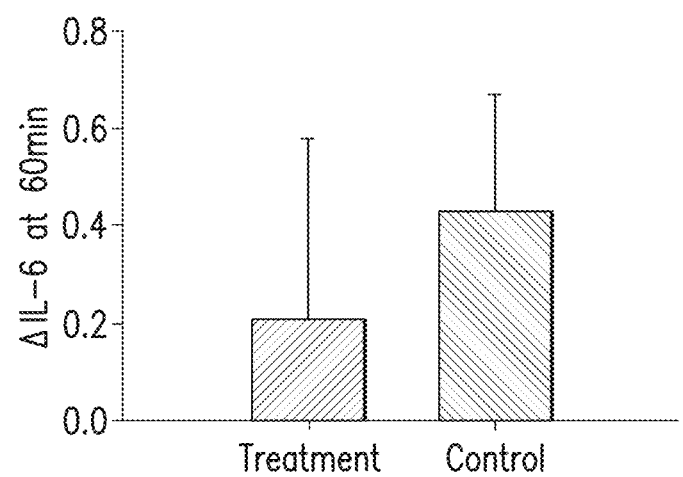
FIG. 13A is a bar graph showing the change in the pro-inflammatory cytokine, IL-6, at 60 minutes.
Figure 13B:
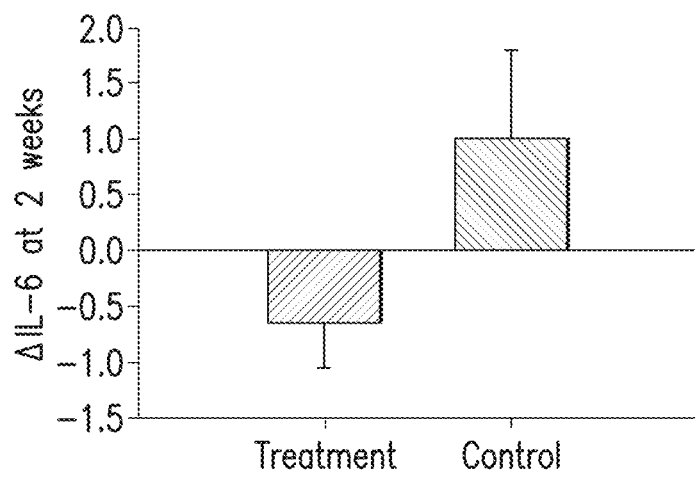
FIG. 13B is a bar graph showing the change in the pro-inflammatory cytokine, IL-6, at two weeks.

FIGS. 13A and 13B show the change in the pro-inflammatory cytokine, IL-6, at 60 minutes and 2 weeks, respectively. The data in FIGS. 13A and 13B show that both a single dose of NaHCO$_3$ as well as ingestion of NaHCO$_3$ for 2 weeks reduces IL-6 in humans.

Figure 14A:
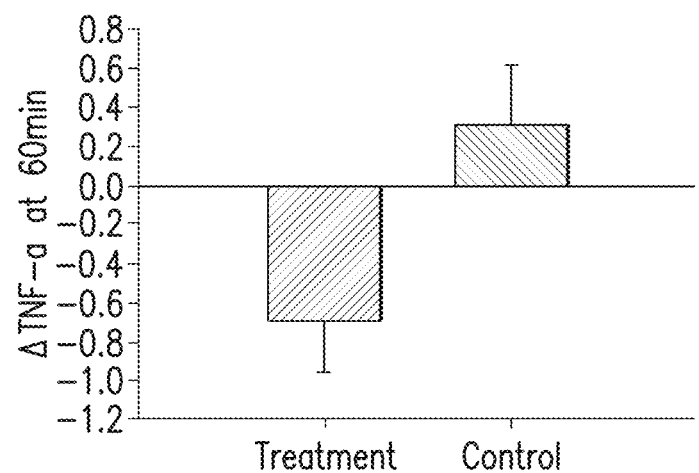
FIG. 14A is a bar graph showing the change in the pro-inflammatory cytokine, TNF-α, at 60 minutes.
Figure 14B:
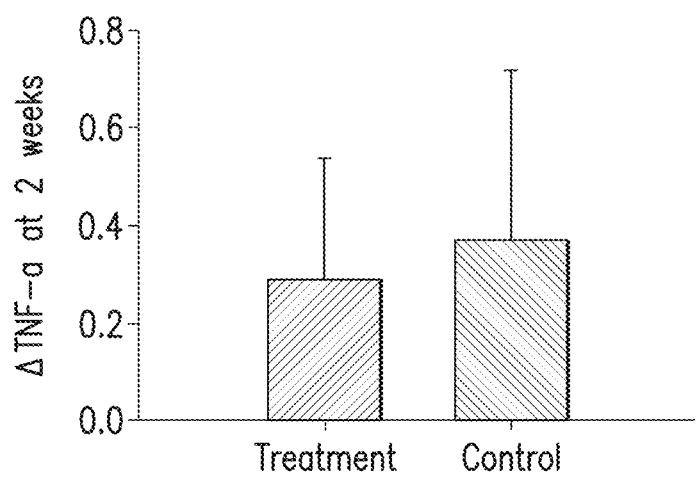
FIG. 14B is a bar graph showing the change in the pro-inflammatory cytokine, TNF-α, at two weeks.

FIGS. 14A and 14B show the change in the pro-inflammatory cytokine, TNF-α, at 60 minutes and 2 weeks, respectively. The data in FIGS. 14A and 14B show that both a single dose of NaHCO$_3$ as well as ingestion of NaHCO$_3$ for 2 weeks reduces TNF-α in humans.

Example 5

Ingestion of NaHCO$_3$ Reduces Systemic Inflammation

Methods and Materials

C-Reactive Protein was determined in plasma using standard clinical laboratory procedures (Labcorp).

Results

Figure 15:
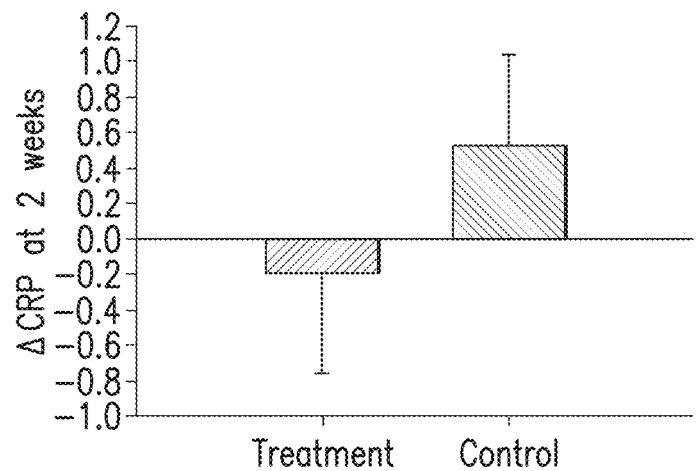
FIG. 15 is a bar graph showing the change in the acute phase reactant C-reactive protein (CRP) at two weeks.

FIG. 15 shows the change in the acute phase reactant C-reactive protein, which is a marker of global systemic inflammation, at two weeks. As shown in FIG. 15, ingestion of NaHCO$_3$ for two weeks reduces the acute phase reactant C-reactive protein.

Example 6

Ingestion of NaHCO$_3$ Demonstrates a Positive Relationship Between the Change in Parasympathetic Activity and Potassium Methods and Materials Parasympathetic activity was determined as described above. Potassium levels were determined using standard clinical laboratory procedures (Labcorp).

Results

Figure 16:
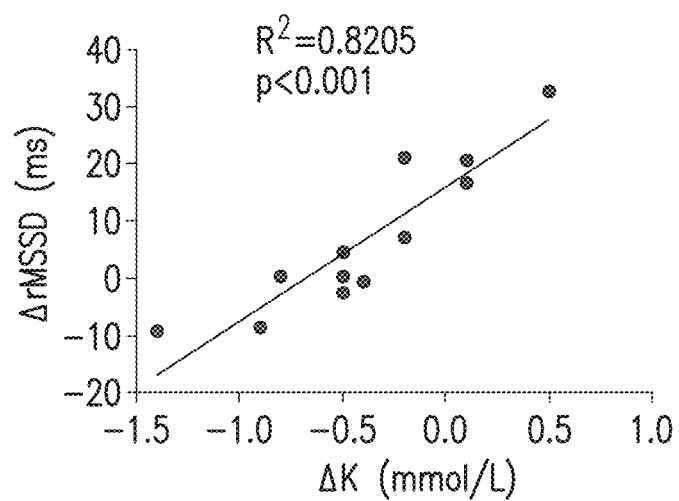
FIG. 16 is a graph showing the relationship between the change in rMSSD (i.e., the parasympathetic activity) and potassium.

FIG. 16 shows the relationship between the change in rMSSD (i.e., the parasympathetic activity) and potassium. The data in FIG. 16 demonstrates that the increase in parasympathetic activity in response to NaHCO$_3$ is about 67% dependent on the change in potassium following NaHCO$_3$. This relationship is remarkable in human physiology.

Example 7

Co-Administration of NaHCO$_3$ and NH$_4^+$ Reduces Inflammation

Methods and Materials

To identify and evaluate immune cells in splenic tissues, a flow cytometry-based assay was employed. Buffering capacity and pH were determined by titration of the solutions with HCl.

Results

Figure 17:
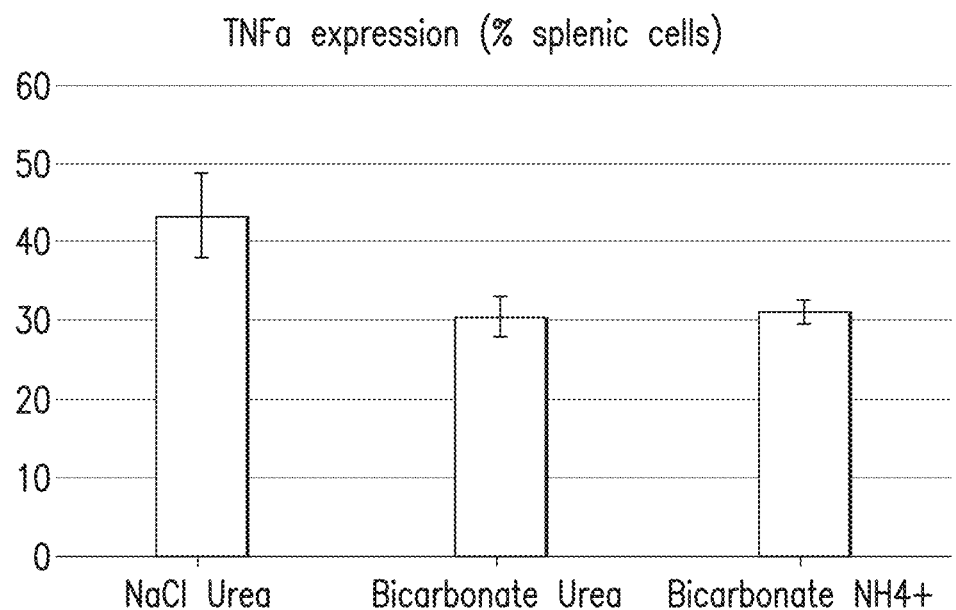
FIG. 17 is a bar graph showing the number of TNF-α (inflammatory) expressing cells.

FIG. 17 shows the number of TNF-α (inflammatory) expressing cells. As discussed above, rats drinking NaHCO$_3$ have significantly reduced numbers of TNF-α (inflammatory) expressing cells due to activation of the cholinergic anti-inflammatory pathway with HCO$_3$. The data in FIG. 17 shows that co-administration of NaHCO$_3$ and the metabolic acid, ammonium (NH$_4^+$), also significantly reduces the number of TNF-α (inflammatory) expressing cells. That is, both solutions are equally effective at reducing TNF-α expressing inflammatory cells in the spleens of rats when given orally. Moreover, co-administration of bicarbonate with the metabolic acid, NH$_4^+$, does not change the pH or buffering capacity of the oral drinking solution significantly. Both HCO$_3$/urea and HCO$_3$/NH$_4^+$ have a pH of about 8. Urea is given as an osmotic control for NH$_4^+$.

Example 8

Co-Administration of NaHCO$_3$ and NH$_4^+$ Prevents Alkalization of Urine

Methods and Materials

For urine collection rats were placed in rat metabolic cages for 24 hours (Nalgene, Rochester, N.Y.). Urine was collected and weighed for volume determination. Urinary titratable acids were determined by titration of 5 mL of urine with NaOH or HCl to pH 7.4. Urinary NH$_4$+ concentration was determined using an ammonia ion selective electrode (Orion high performance ammonia ion selective electrode (Thermo Fischer Scientific Inc)).

Results

Figure 18:
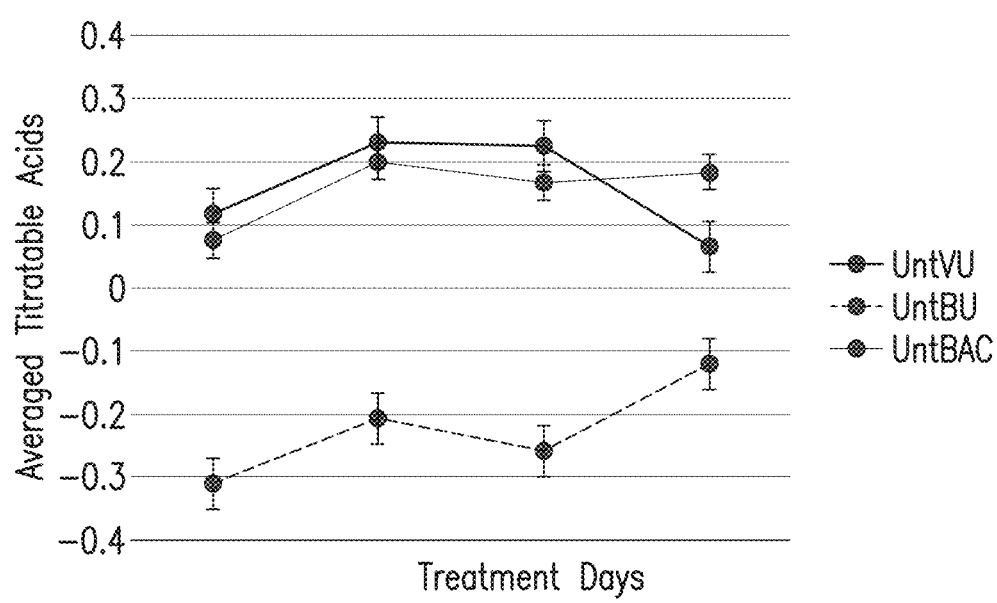
FIG. 18 is a line graph showing four days of treatment in rats as titratable acid excretion.

Despite having no effect on the inflammatory response, co-administration of equimolar NaHCO$_3$ and ammonium (NH$_4^+$) prevents alkalization of the urine. FIG. 18 shows titratable acid excretion in rats treated for four days. As shown in FIG. 18, co-administration of NaHCO$_3$ and ammonium (NH$_4^+$) prevents systemic alkalization but still stimulates an anti-inflammatory response in rats.

Example 9

Co-Administration of Methionine with NaHCO$_3$ Does Not Affect the Anti-Inflammatory Effects of NaHCO$_3$ Methods and Materials To identify and evaluate immune cells in splenic tissues, a flow cytometry-based assay was used.

Results

Figure 19:
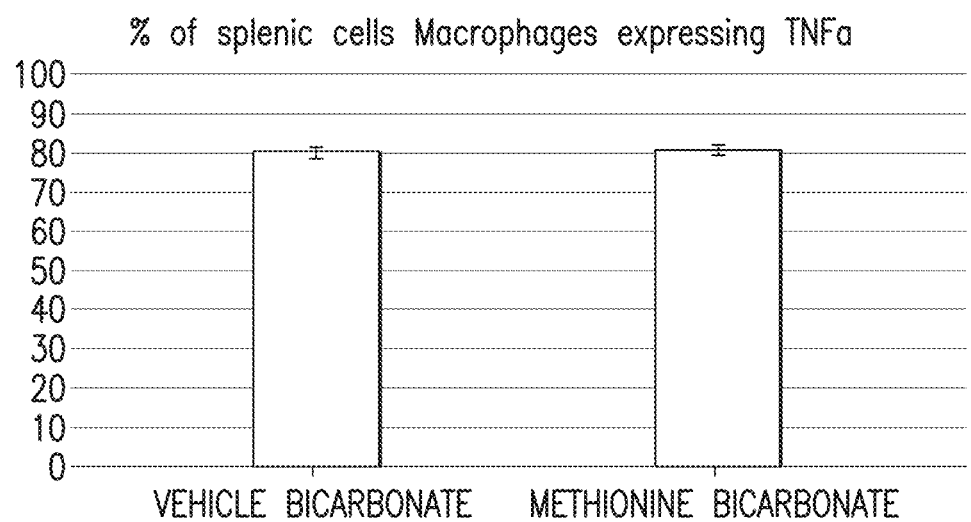
FIG. 19 is a bar graph showing the percentage of splenic macrophage cells expressing TNF-α after three days of vehicle bicarbonate treatment and methionine bicarbonate treatment.

FIG. 19 shows the percentage of splenic macrophage cells expressing TNF-α after three days of vehicle bicarbonate treatment and methionine bicarbonate treatment. As shown in FIG. 19, there is no difference between animals treated with vehicle (urea in saline) bicarbonate, which has been shown to activate the anti-inflammatory response, and bicarbonate with methionine. This indicates that the addition of methionine does not prevent the anti-inflammatory effects of NaHCO$_3$.

Metabolic acid inducers like the amino acid methionine are not strong acids in solution, so do not greatly alter the buffering capacity or pH of a sodium bicarbonate solution. As such, when ingested, a dual solution of NaHCO$_3$+ methionine, stimulates a similar amount of acid secretion by the stomach and promotes a similar splenic anti-inflammatory response to that of ingestion of a solution of sodium bicarbonate alone (FIGS. 22A-22B). Once absorbed and metabolized by the liver however, methionine produces acid (H+) which counteracts the alkalizing effect of the addition of bicarbonate to the body. Thereby promoting a strong acid secretion by the stomach and anti-inflammatory response but causing no net change in systemic acid/base status which can produce deleterious effects such as hypokalemia or kidney stones.

Example 10

The Effect of NaHCO$_3$ Alone or NaHCO$_3$ with a Metabolic Acid (MA) to Promote a Systemic Anti-Inflammatory Response in Rats is Similar Results Data from healthy rats demonstrates that 3 days of drinking either sodium bicarbonate (NaHCO3, 0.1M, n=3) or Sodium bicarbonate+a metabolic acid (0.1M NaHCO3 +MA, n=3) induces robust but identical increases in anti-inflammatory T-regulatory cells and decreases in pro-inflammatory TH17 cells despite NaHCO3+ MA having no net systemic alkalinizing effect (measured by urine net acid excretion (not shown)).

Example 11

Only Alkali that Promote Stomach Acid Secretion, Not Systemic Alkalization Alone, Drive the Anti-Inflammatory Response Results 4 days of drinking NaHCO3 significantly increased the number of circulating anti-inflammatory T cells (FOXP3+ T-regs) in rats (Individual animal data shown n=3, responses connected by solid line). Following a 2 week washout with tap water, rats were given the metabolic alkali NaCitrate in drinking water for 4 days. Na Citrate had no effect to promote anti-inflammatory T-regulatory cells in rats as it does not promote stomach acid secretion as it is only converted to a base once it is absorbed and passes through the liver. Following a further 2 week washout with tap water, rats were given a combination of NaHCO3 with the metabolic acid inducer NH4Cl. NaHCO3+NH4Cl significantly increased circulating anti-inflammatory cells as it drives acid secretion in the stomach despite having no effect on systemic (body) acid base status.

What is claimed is:

1. A method for treating an inflammatory condition associated with vagal nerve efferent pathways in a subject in need thereof, comprising:
orally administering to the subject a solution consisting of equimolar amounts of sodium bicarbonate in an amount of about 0.01 M to about 0.5 M and ammonium ($NH_4^+$) in water in an amount effective to increase the pH of the stomach to at least 6-9 to activate vagal nerve efferent pathways to reduce or inhibit the inflammation,
wherein the solution of the sodium bicarbonate and the ammonium in equimolar amounts provides selective stomach alkalization without systemic alkalization.

2. The method of claim 1, wherein the solution of sodium bicarbonate and the ammonium ($NH_4^+$) is in effective amounts to inhibit or reduce one or more inflammatory M1 macrophages and/or one or more inflammatory neutrophils in the blood of the subject.

3. The method of claim 1, wherein the solution of sodium bicarbonate and the ammonium ($NH_4^+$) is in effective amounts to inhibit or reduce one or more pro-inflammatory cytokines selected from the group consisting of IL1α, IL1β, IL6, and TNFα.

4. The method of claim 1, wherein the inflammatory condition is selected from the group consisting of chronic kidney disease, rheumatoid arthritis, inflammatory bowel disease, and Crohn's disease.

5. A method of stimulating vagal nerve efferent pathways in a subject in need thereof, comprising:
orally administering to the subject a solution consisting of equimolar amounts of sodium bicarbonate in an amount of about 0.01 M to about 0.5 M and ammonium ($NH_4^+$) in water in an amount effective to increase the pH of the stomach to at least 6-9 to stimulate vagal nerve efferent pathways,
wherein the solution of the sodium bicarbonate and the ammonium in equimolar amounts provides selective stomach alkalization without systemic alkalization.

6. The method of claim 5, wherein the solution of the sodium bicarbonate and the ammonium is in effective amounts to alkalinize the pH of the stomach of the subject.

7. A solution,
consisting of equimolar amounts of sodium bicarbonate in an amount of about 0.01 M to about 0.5 M and ammonium ($NH_4^+$) in water in an amount effective to increase the pH of the stomach to at least 6-9,
wherein the solution of the sodium bicarbonate and the ammonium in equimolar amounts provides selective stomach alkalization without systemic alkalization.

8. The solution of claim 7, wherein the solution is formulated for oral administration.

9. The solution of claim 7, wherein the solution is formulated as an extended release formulation.

10. The solution of claim 7, wherein the solution of sodium bicarbonate and the ammonium ($NH_4^+$) is in effective amounts to inhibit or reduce one or more inflammatory M1 macrophages and/or one or more inflammatory neutrophils and thereby inhibit or reduce inflammation in a subject.

11. A method for treating or preventing a cardiovascular disease or a metabolic disorder, comprising:
administering to a subject in need thereof an effective amount of the solution of claim 7.

12. The method of claim 11, wherein the cardiovascular disease or metabolic disorder is selected from the group consisting of atherosclerosis, hypertension, obesity, and type 2 diabetes.

* * * * *